(12) United States Patent
Takemoto et al.

(10) Patent No.: US 8,308,744 B2
(45) Date of Patent: Nov. 13, 2012

(54) ENDOSCOPIC TREATMENT INSTRUMENT

(75) Inventors: Shotaro Takemoto, Tokyo (JP); Tetsuya Yamamoto, Hanno (JP); Tatsutoshi Hashimoto, Tokyo (JP); Kiyotaka Matsuno, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1112 days.

(21) Appl. No.: 11/652,824

(22) Filed: Jan. 12, 2007

(65) Prior Publication Data

US 2007/0270637 A1 Nov. 22, 2007

Related U.S. Application Data

(63) Continuation-in-part of application No. 11/331,962, filed on Jan. 13, 2006.

(51) Int. Cl.
*A61B 17/04* (2006.01)

(52) U.S. Cl. .................................................. 606/144

(58) Field of Classification Search ................ 606/139, 606/144, 145, 148, 205–209, 157, 158
See application file for complete search history.

(56) References Cited

U.S. PATENT DOCUMENTS

| | | | |
|---|---|---|---|
| 3,090,386 A | | 5/1963 | Babcock |
| 4,088,313 A | * | 5/1978 | Pearson ........................... 269/88 |
| 4,935,027 A | | 6/1990 | Yoon |
| 5,470,338 A | | 11/1995 | Whitfield et al. |
| 5,575,800 A | * | 11/1996 | Gordon .......................... 606/144 |
| 5,692,734 A | * | 12/1997 | Aldredge, Sr. ................ 269/166 |
| 5,735,849 A | * | 4/1998 | Baden et al. .................... 606/51 |
| 6,168,601 B1 | * | 1/2001 | Martini .......................... 606/90 |
| 6,315,714 B1 | | 11/2001 | Akiba |

(Continued)

FOREIGN PATENT DOCUMENTS

JP 2002-159499 6/2002

(Continued)

OTHER PUBLICATIONS

US Office Action dated Dec. 18, 2009 in related U.S. Appl. No. 11/331,962.

(Continued)

*Primary Examiner* — Julian Woo
*Assistant Examiner* — Christopher L Templeton
(74) *Attorney, Agent, or Firm* — Scully, Scott, Murphy & Presser, P.C.

(57) ABSTRACT

An endoscopic treatment instrument having a treatment portion having: an input member; a first link disconnectably connected to the input member; a first control plate disposed in a first connecting portion, inserting the input member through the first control plate, and engaging the input member by inclination of the first control plate; a first forceps member opening and closing according to advancing and retracting motions of the first link; a second link disconnectably connected to the input member; a second control plate disposed in a second connecting portion, inserting the input member through the second control plate, and engaging the input member by inclination of the second control plate; and a second forceps member opening and closing according to advancing and retracting motions of the second link, the opening-and-closing angle of the second forceps member being less than that of the first forceps member.

7 Claims, 88 Drawing Sheets

U.S. PATENT DOCUMENTS

| | | |
|---|---|---|
| 6,338,475 B1 * | 1/2002 | Ping ............................ 269/6 |
| 6,988,987 B2 | 1/2006 | Ishikawa et al. |
| 7,338,502 B2 | 3/2008 | Rosenblatt |
| 2002/0116011 A1 | 8/2002 | Chee Chung et al. |
| 2003/0181924 A1 | 9/2003 | Yamamoto et al. |
| 2003/0216613 A1 * | 11/2003 | Suzuki et al. ............. 600/104 |
| 2004/0147941 A1 | 7/2004 | Takemoto et al. |
| 2005/0234297 A1 | 10/2005 | Devierre et al. |
| 2006/0258905 A1 | 11/2006 | Kaji et al. |
| 2006/0282088 A1 | 12/2006 | Ryan |

FOREIGN PATENT DOCUMENTS

| | | |
|---|---|---|
| JP | 2003-225241 | 8/2003 |
| JP | 2005-161050 | 6/2005 |

OTHER PUBLICATIONS

US Office Action dated Jun. 17, 2010 in related U.S. Appl. No. 11/331,962.

* cited by examiner

ENDOSCOPIC TREATMENT INSTRUMENT

This is a Continuation-In-Part application that claims priority on U.S. patent application Ser. No. 11/331,962, filed Jan. 13, 2006, the contents of which are incorporated herein by reference.

BACKGROUND OF THE INVENTION

1. Field of the Invention

The present invention relates to a treatment instrument for an endoscope, and more particularly, to a retaining device placed and retained in the interior of a human body and an applicator used to retain the retaining device therein.

2. Background Art

An abdominal operation in which a medical procedure is performed by largely incising the abdominal wall, a laparoscopic surgery in which a medical procedure is performed by approaching the abdominal cavities through an incision formed in the abdominal wall, or an endoscopic procedure in which a desired treatment is performed by inserting a flexible endoscope into the human body through the mouth or the anus is conventionally known as a method for performing a medical procedure that deals with, for example, internal organs of the human body.

In the medical procedures using these methods, bodily tissues are sutured, tightly bound, or ligated. A retaining device that is placed and retained in a human body is often used when such a treatment is performed. This type of retaining device is attached to an applicator, and is retained in a desired region of the human body by operating the applicator from the interior of the human body.

US Patent Application Publication No. 2003-0181924A1 discloses an example of this type of retaining device and an applicator used to retain the retaining device (hereinafter, a "treatment instrument" is used as a general term for the retaining device and the applicator). The treatment instrument disclosed by this related art has the following structure. A detachable needle attached to a curved needle is inserted into bodily tissues, and then a hook sheath is moved toward the distal end of the instrument. Thereafter, the detachable needle is engaged by a casing engaged with the distal end. The hook sheath is then pulled toward the proximal end of the instrument, and the detachable needle is detached from the curved needle.

SUMMARY OF THE INVENTION

It is an object of the present invention to provide an improved endoscopic treatment instrument having higher operability.

The endoscopic treatment instrument according to a first aspect of the present invention includes an insertion portion having a distal end and a proximal end, the distal end being inserted into a human body; a treatment portion provided at the distal end of the insertion portion; and a control portion provided at the proximal end of the insertion portion, and the treatment portion includes a pair of forceps members; a tip cover which supports a pivot shaft that pivots at least one of the pair of forceps members openably and closably with respect to the other forceps member; a distal end holding portion that is fixed to the distal end of the insertion portion and in which the tip cover is held relatively movably toward the distal end of the insertion portion and toward the proximal end of the insertion portion; a distal end locking member that restrains a relative movement by locking the tip cover onto the distal end holding portion when the pair of forceps members is opened to grasp a specified object; and a distal end release member that is provided on an operational member by which the pair of forceps members is opened and closed and that releases an engagement made by the distal end locking member between the tip cover and the distal end holding portion at least when the pair of forceps members is closed.

The endoscopic treatment instrument according to a second aspect of the present invention includes a casing holding portion that is provided at a distal end of an insertion portion to be inserted into a human body and that holds a casing connected to a tip member by a thread, the casing containing the tip member detachably attached to one of a pair of forceps members after being passed through a tissue in response to a closing motion of the pair of forceps members at least one of which is pivoted openably and closably with respect to the other forceps member; a casing locking member which engages the casing holding portion and the casing together; and a guide member that is provided at the tip cover and that controls an engagement state made by the casing locking member between the casing holding portion and the casing.

The endoscopic treatment instrument according to a third aspect of the present invention includes: a pair of forceps members; a tip cover which supports a pivot shaft that pivots at least one of the pair of forceps members openably and closably with respect to the other forceps member; a receiving portion that detachably holds a side of a distal end of an endoscope to be inserted into a human body; and a regulating member that regulates a position of the distal end of the endoscope at a relative position with respect to the tip cover in order to restrict an amount of projection of the distal end of the endoscope with respect to the receiving portion.

The endoscopic treatment instrument according to a fourth aspect of the present invention includes a first sheath and a second sheath to a distal end of each of which a treatment portion used to perform treatment is connected and to a proximal end of each of which a control portion that operates the treatment portion is connected; a first holder which bundles the first sheath and the second sheath together; a second holder which bundles the first sheath and the second sheath together and that is provided nearer to the distal end than the first holder; a first adjusting member that provides sliding friction to the second sheath with respect to the first holder; and a second adjusting member that provides smaller sliding friction than the first adjusting member to the first sheath with respect to the second holder.

The retaining device according to a fifth aspect of the present invention includes: a string member that has an end and an opposite end; a tip member that is connected to the end of the string member; a thread locking member provided at the string member; a casing that has a space where the tip member and the thread locking member are contained and in which a tip-member locking member that is engaged with the tip member is provided; and a hole that is formed in the casing and into which a device that releases locking of the tip member by the tip-member locking member can be inserted.

The endoscopic treatment instrument according to a sixth aspect of the present invention includes: an insertion portion comprising a distal end and a proximal end, the distal end being inserted into the insertion portion; a treatment portion disposed to the distal end; and a control portion disposed to the proximal end, wherein the treatment portion includes: an extending and retractable input member operated by the control portion; a first link disconnectably connected to the input member through a first connecting portion; a first forceps member capable of opening and closing by the first link; a second link disconnectably connected to the input member through a second connecting portion; and a second forceps member freely opening and closing by the second link, the opening-and-closing angle of the second forceps member being less significant than that of the first forceps member, and the first connecting portion releases the connection between the input member and the first link until the second forceps member is opened by a predetermined degree of openness.

The endoscopic treatment instrument according to a seventh aspect of the present invention includes: an insertion portion including a distal end and a proximal end, the distal end being inserted into a human body; a treatment portion disposed to the distal end; and a control portion disposed to the proximal end, wherein the treatment portion including: an extending and retractable input member operated by the control portion; a first link disconnectably connected to the input member through a first connecting portion; a first forceps member capable of opening and closing by the first link; a second link disconnectably connected to the input member through a second connecting portion; and a second forceps member freely opening and closing by the second link, the opening-and-closing angle of the second forceps member being less significant than that of the first forceps member, and the second connection portion releases the connection between the input member and the second link after the input member is driven by a predetermined length in a direction of closing the fully open second forceps member.

The endoscopic treatment instrument according to a sixth aspect of the present invention includes: an insertion portion comprising a distal end and a proximal end, the distal end being inserted into the insertion portion; a treatment portion disposed to the distal end; and a control portion disposed to the proximal end, wherein the treatment portion includes: an extending and retractable input member operated by the control portion; a first link disconnectably connected to the input member through a first connecting portion; a first forceps member capable of opening and closing by the first link; a second link disconnectably connected to the input member through a second connecting portion; and a second forceps member freely opening and closing by the second link, the opening-and-closing angle of the second forceps member being less significant than that of the first forceps member, and the second connection portion releases the connection between the input member and the second link when the second forceps member is fully open.

The endoscopic treatment instrument according to a ninth aspect of the present invention includes: an insertion portion including a distal end and a proximal end, the distal end being inserted into a human body; a treatment portion disposed to the distal end; and a control portion disposed to the proximal end, wherein the treatment portion including: a pair of forceps members; a tip cover for supporting a pivot shaft for pivoting at least one of the pair of freely opening and closing forceps members relative to the other; a casing holding portion accommodated in the tip cover, the casing holding portion supporting a casing capable of receiving a needle detachably attached to the forceps members; and a supporting member disposed in the casing holding portion, the supporting member having an elastically deformable arm capable of engaging the casing, and wherein in the casing holding portion, the arm is pressed to be elastically deformed in the vicinity of the distal end so that the arm engages the casing, and a space is disposed in the vicinity of the proximal end so that the arm disengaged from the casing is restored to open in the space.

In the attaching device according to a tenth aspect of the present invention in use for attaching a cartridge to a suture instrument, the cartridge is connected to a casing capable of accepting a suture thread put through a detachable thread attached to the suture instrument, the device comprises: a needle-supporting section for supporting the detachable needle, the needle-supporting section being capable of accepting the suture instrument; and a holder for accommodating the casing, the holder being urged in a direction separate from the suture instrument.

DETAILED DESCRIPTION OF THE INVENTION

Figure 1:
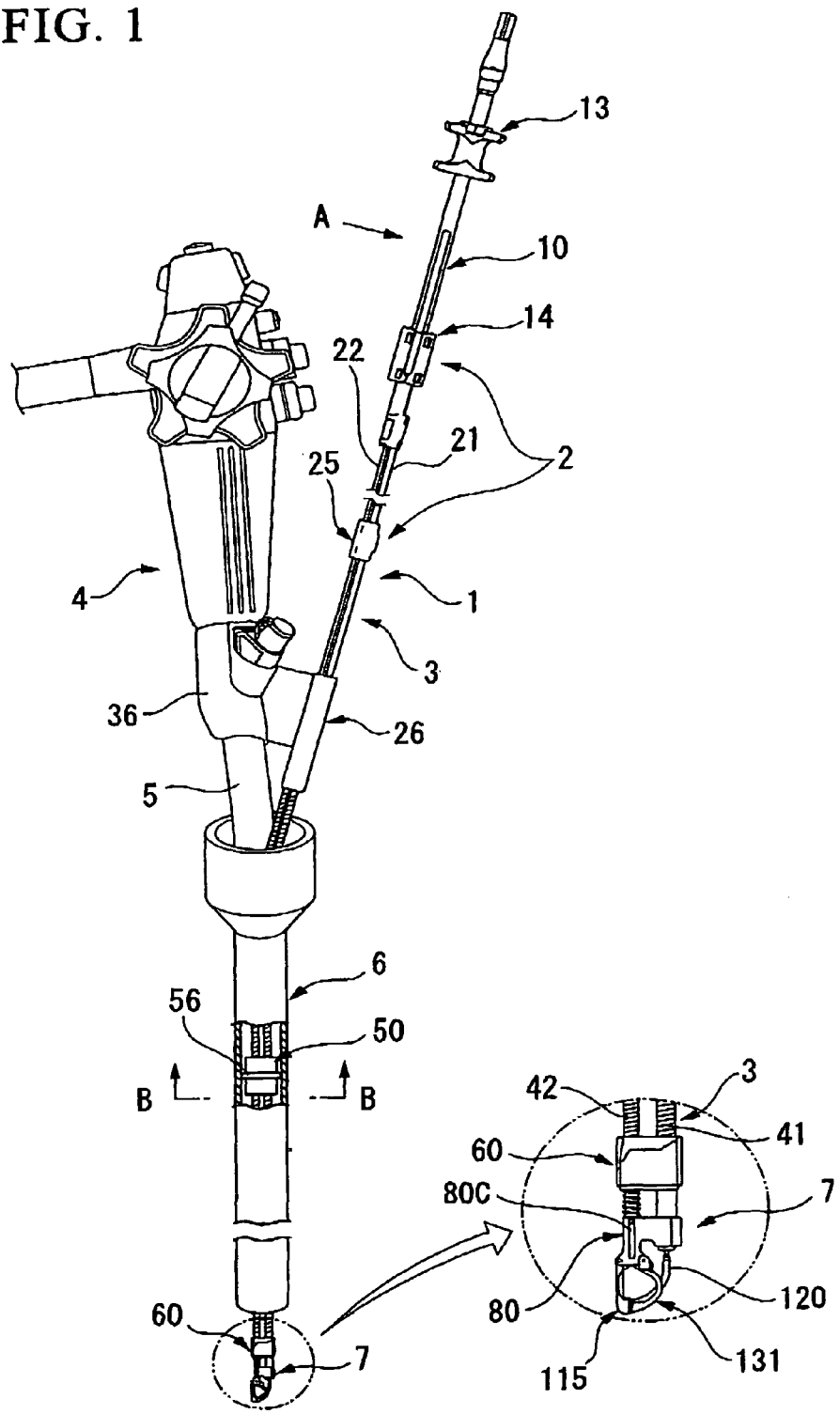
FIG. 1 is a view showing a schematic structure of a suture instrument which is an embodiment of an endoscope and an endoscopic treatment instrument.

Embodiments of the present invention will be hereinafter described in detail with reference to the accompanying drawings. The same reference numerals are added to the same elements as those shown in each embodiments. In addition, overlapping descriptions between the embodiments will be omitted.

First Embodiment

FIG. 1 shows a suture instrument that is an example of an endoscopic treatment instrument. A suture instrument (applicator) 1 has a long insertion portion 3 extended from a control portion 2 that is operated by an operator. The insertion portion 3 is inserted in an overtube 6 together with an endoscope inserting part 5 of an endoscope 4. The tip of the insertion portion 3 projects from the distal end of the overtube 6. A treatment portion 7 is attached to the tip of the insertion portion 3.

Figure 2:
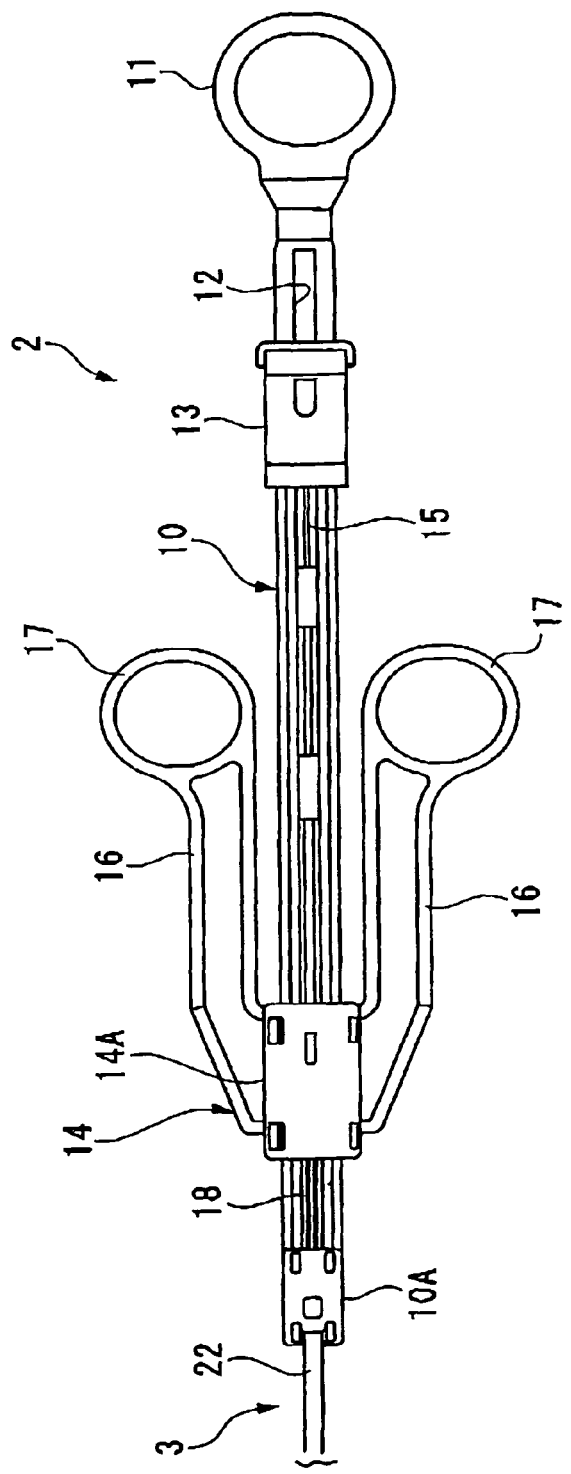
FIG. 2 is a view on arrow A in FIG. 1, showing a structure of a control portion.

As shown in FIG. 2, the control portion 2 has an elongated control body 10 that has a rigid shaft extending in an insertion direction. The insertion portion 3 extends from a distal end 10A of the control body 10. A finger-hook ring 11 is attached to the proximal end of the control body 10. A slit 12 is provided along a length direction of the control body 10 on the side nearer to the distal end than the ring 11. A forceps operating portion 13 and a hook operating portion 14, in order from the side of the ring 11, are attached to the slit 12 independently and slidably in the axial direction of the control body 10. ABS (acrylonitrile butadiene styrene) resin, polycarbonate, polyacetal, polyphenylsulfone, polyphthalamide, or polyether ether ketone can be mentioned as a material of the control portion 2. The instrument can be produced at low cost by making the control portion 2 of ABS resin, polycarbonate, or the like. Since slidability is increased by making the control portion 2 of polyacetal, a physical force required in operating the instrument can be reduced. Additionally, since excellent chemical resistance and excellent heat resistance can be obtained by making the control portion 2 of polyphenylsulfone, polyphthalamide, or polyether ether ketone, a change in quality caused by disinfection or sterilization becomes small.

A forceps operating wire (a forceps operating member, a first wire) 15 is fixed to the forceps operating portion 13. The forceps operating wire 15 is guided to the inside of the insertion portion 3 through the inside of the slit 12. In the hook operating portion 14, a pair of handles 16 extend from a side of a cylinder 14A toward the proximal end, and a finger-hook ring 17 is formed integrally with the base of the handle 16. The interval between the pair of handles 16 is large enough to allow the entry of the forceps operating portion 13. The hook operating portion 14 can have a long stroke by pulling the ring 17 of the handle 16 beyond the forceps operating portion 13. A hook operating wire (a hook operating member, a second wire) 18 is fixed to the hook operating portion 14. The hook operating wire 18 is guided to the inside of the insertion portion 3 through the inside of the slit 12. The number of the handles 16 may be one, or may be more than two.

Each of the control body 10, the forceps operating portion 13, and the hook operating portion 14 is made out of a resinous molded article, and are produced by fixing integrally-molded members in a snap-fit manner. In more detail, the control body 10 is produced by bending a developed member and then fixing this by a snap-fit connection. An independently molded ring 11 is fitted to the proximal end of the control body 10. Each of the forceps operating portion 13 and the hook operating portion 14 is produced by bending a developed member in such a way as to cover the control body 10 and then fixing this by a snap-fit connection.

Figure 3:
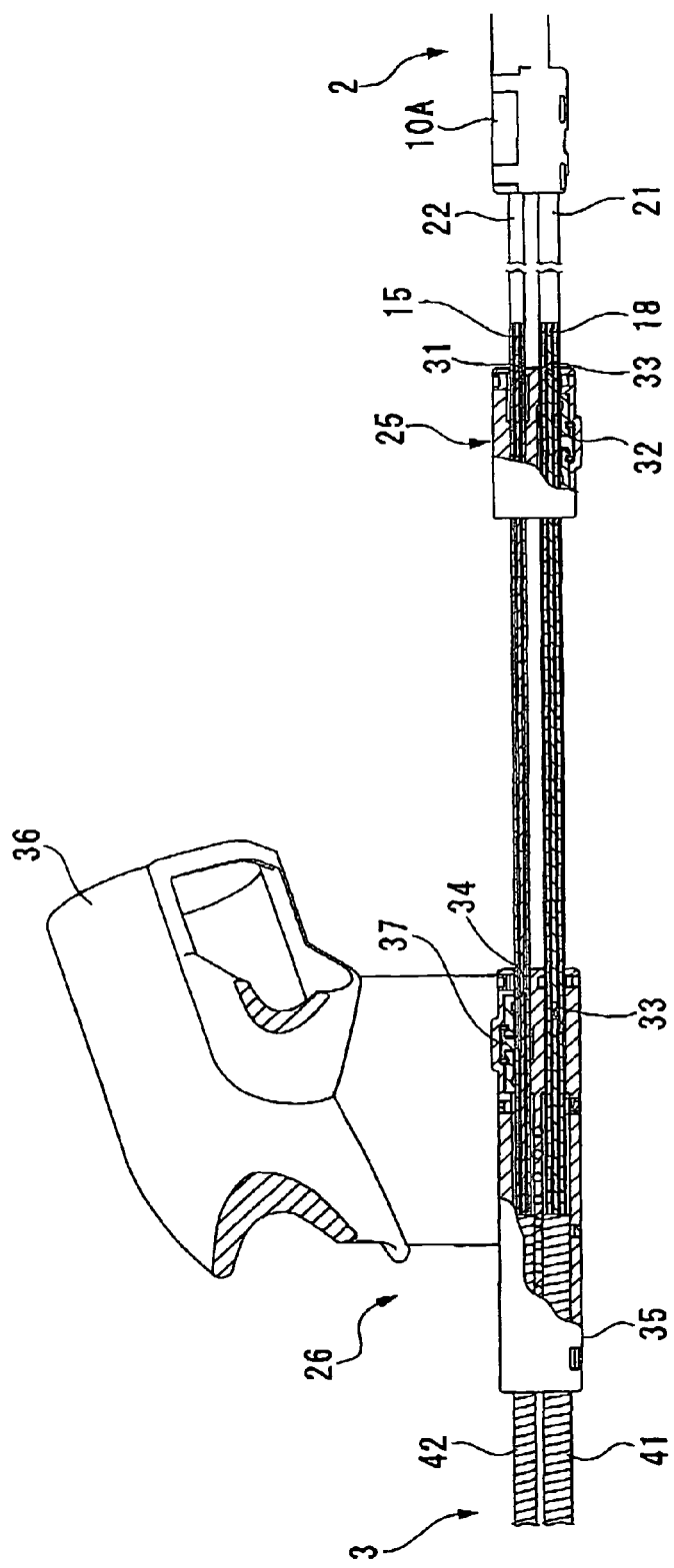
FIG. 3 is a partial sectional view showing a structure of an insertion portion.

As shown in FIG. 3, the insertion portion 3 has a hook sheath 21 extending from the distal end of the control portion 2 and a forceps sheath 22. The hook operating wire 18 is passed movably back and forth through the inside of the hook sheath 21. The forceps operating wire 15 is passed movably back and forth through the inside of the forceps sheath 22.

A movement control portion (a first holder) 25 that is a constituent of the control portion 2 and a scope holder (a second holder) 26 are disposed at the path of the insertion portion 3. The two sheaths 21 and 22 are bundled in parallel with each other by the movement control portion 25 and the scope holder 26. The movement control portion 25 has through-holes 30 and 31 that are formed in parallel with each other and through which the two sheaths 21 and 22 pass, respectively. A first adjusting member 32 is inserted in the through-hole 30 for the hook sheath 21 in such a way that its end projects therefrom. In this embodiment, a screw is used as the first adjusting member 32. The sliding friction of the hook sheath 21 is increased by tightening the first adjusting member 32 so as to come into contact with the hook sheath 21. On the other hand, the forceps sheath 22 is fixed to the movement control portion 25 in a state of being inserted in the through-hole 31.

The scope holder 26 has a holder body 35 having through-holes 33 and 34 that are formed in parallel with each other and through which the two sheaths 21 and 22 pass, respectively. A cylindrical receiving portion 36 through which the endoscope inserting part 5 of the endoscope 4 passes from the holder body 35 is formed integrally therewith. The through-hole 34 is formed in the scope holder 26. The forceps sheath 22 is inserted in the through-hole 34 movably back and forth. A second adjusting member 37 is disposed so as to come into contact with the forceps sheath 22. In this embodiment, a screw is used as the second adjusting member 37. The sliding friction of the forceps sheath 22 is increased by tightening the second adjusting member 37 so as to come into contact with the forceps sheath 22. On the other hand, no adjusting member is disposed at the through-hole 33 of the hook sheath 21 so as to be movable back and forth.

Both sheaths 21 and 22 proceed toward the scope holder 26 either by gripping the sheaths 21 and 22 exposed between the scope holder 26 and the movement control portion 25 or by extending the movement control portion 25. Since the endoscope 4 held by the scope holder 26 does not move, the treatment portion 7 attached to the distal ends of both sheaths 21 and 22 can be extended toward the endoscope 4.

On the other hand, when an operator intends to extend only the hook sheath 21, the hook sheath 21 is gripped to be extended. At this time, the movement control portion 25 is not moved by the first adjusting member 32. The reason is that the sliding friction in the movement control portion 25 of the hook sheath 21 is small, and the sliding friction caused by the second adjusting member 37 in the scope holder 26 of the forceps sheath 22 is great. Therefore, the hook sheath 1121 slides with respect to the movement control portion 25, and only the hook sheath 21 is extended.

Thus, the movement control portion 25 and the scope holder 26 make it possible to properly use the sheaths 21 and 22 so as to extend both of the sheaths 21 and 22 or extend only the hook sheath 21. The sheaths 21 and 22 being operated can be more easily confirmed by making a difference in color between the hook sheath 21 and the forceps sheath 22, by making the surface of one of the sheaths 21 and 22 uneven, or by making a difference in outer diameter between the sheaths 21 and 22, in order to help the operator to operate the instrument.

The sliding friction caused by the first and second adjusting members 32 and 37 can be adjusted by an amount of tightening. According to another aspect, O rings may be used as the first and second adjusting members 32 and 37.

The movement control portion 25 and the scope holder 26 are produced by fixing integrally-molded members with a snap-fit. In more detail, the movement control portion 25 and the scope holder 26 are produced according to the following way. The sheaths 21 and 22 are passed through grooves of developed members, which become the through-holes 30, 31, 33, and 34, and the first adjusting members 32 and 37 are inserted. Thereafter, the developed members are bent and fixed by a snap-fit connection.

The hook sheath 21 is inserted in a coil sheath 41. The forceps sheath 22 is inserted in a coil sheath 42. The two coil sheaths 41 and 42 extend forwardly from the scope holder 26. Each of the coil sheaths 41 and 42 is made out of a flat coil obtained by closely winding a flat metallic plate. From this structure, component cost can be reduced, and the number of assembling steps can be reduced, when compared to a conventional structure in which tubes are used. The outer surface of each of the hook sheath 21 and the forceps sheath 22 is covered with a heat-shrinkable tube made of low density polyethylene, high density polyethylene, or fluorine resin such as FEP or PFA, or the like. If the heat-shrinkable tube is made of low density polyethylene, the sliding friction with the coil sheaths 41 and 42 can be reduced, and, additionally, the heat-shrinkable tube can be produced at low cost. If the heat-shrinkable tube is made of high density polyethylene, the sliding friction can be reduced further. If the heat-shrinkable tube is made of fluorine resin such as FEP or PFA, a change in quality caused by disinfection or sterilization is slight, because the fluorine resin has small sliding friction and is superior in chemical resistance and heat resistance. The instrument can be operated with a small force by allowing each of the above examples to reduce sliding friction.

Figure 4:
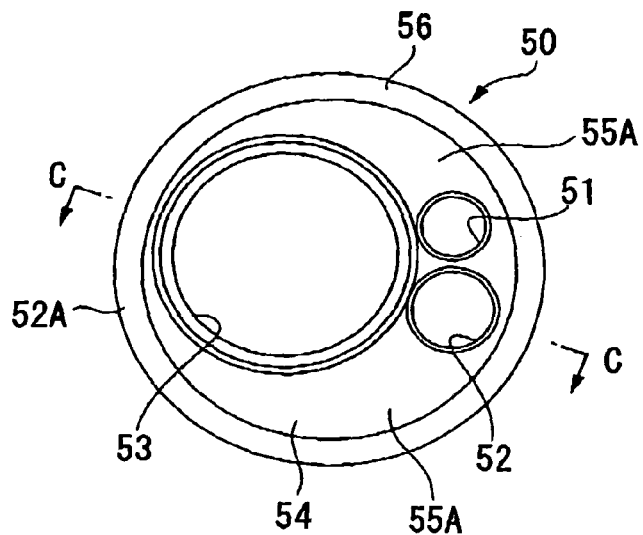
FIG. 4 is a view of a valving element along line B-B in FIG. 1.
Figure 5:
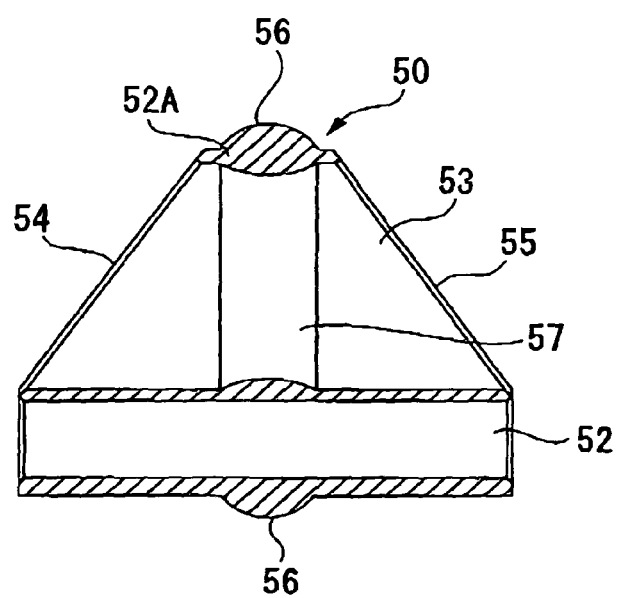
FIG. 5 is a sectional view along line C-C in FIG. 4.

As shown in FIG. 1, a valving element 50 which bundles the two coil sheaths 41 and 42 and the endoscope inserting part 5 of the endoscope 4 together and by which an airtight structure is formed between the valving element 50 and the overtube 6 is disposed midway on the insertion portion 3. Silicone rubber, natural rubber, or isopropylene rubber, or the like can be mentioned as a material of the valving element 50. The valving element 50 is fixed to the coil sheaths 41 and 42, for example, with an adhesive. As shown in FIG. 4 and FIG. 5, the valving element 50 has through-holes 51 and 52 for the sheaths 41 and 42 and a through-hole 53 for the endoscope 4 that are formed in parallel with each other. The valving element 50 has tapered surfaces 54 and 55 formed by slantingly cutting both end surfaces of a cylindrical member. The length in the insertion direction of a part 52A on the opposite side of the through-hole 52 is shortened by the tapered surfaces 54 and 55. A press-fit part 56, whose outer shape is a substantially circular arc when viewed cross-sectionally, is formed on the outer periphery of the valving element 50. A press-fit part 57 having the same shape as the press-fit part 56 is formed on the inner periphery of the through-hole 53 used for the endoscope 4. Since the tapered surfaces 54 and 55 are provided, the valving element 50 is not easily caught by the overtube 6. Since the press-fit part 56 is further provided, the valving element 50 comes into contact with the overtube 6 at only one place in the insertion direction. Therefore, from a decrease in contact area, the sliding friction is expected to be reduced, and it becomes easy to insert the endoscope inserting part 5. Likewise, since the press-fit part 57 makes a contact area with the endoscope inserting part 5 small, it becomes easy to insert the endoscope inserting part 5. Additionally, since the rigidity is improved by making a part 55A thick, the valving element 50 can be prevented from being deformed. Since the opening of each of the through-holes 51 to 53 is tapered to enlarge the outer diameter, the coil sheaths 41 and 42 and the endoscope inserting part 5 can be easily inserted.

Next, the treatment portion 7 will be described.

Figure 6:
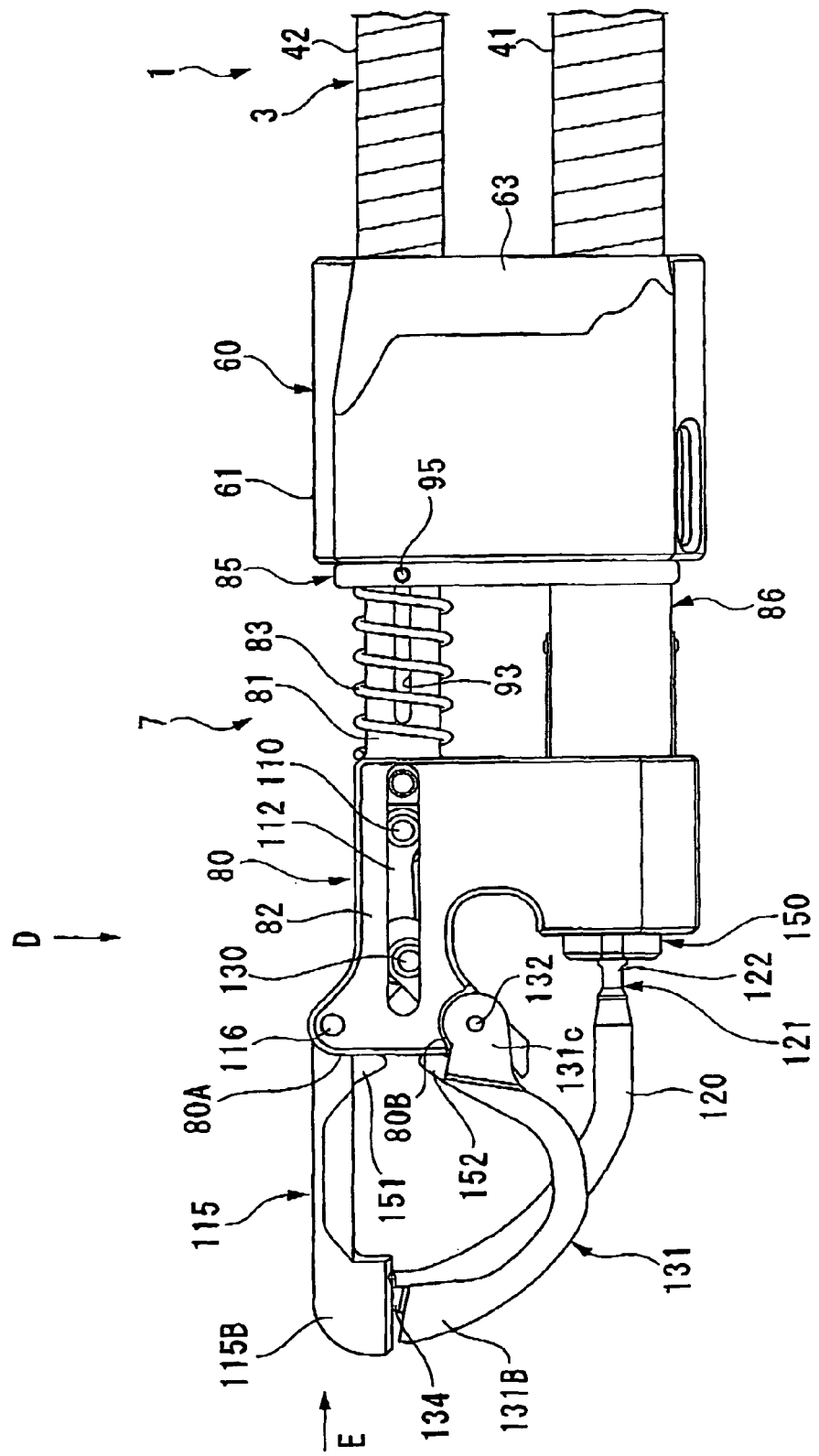
FIG. 6 is an enlarged view of a distal end of the suture instrument.
Figure 7:
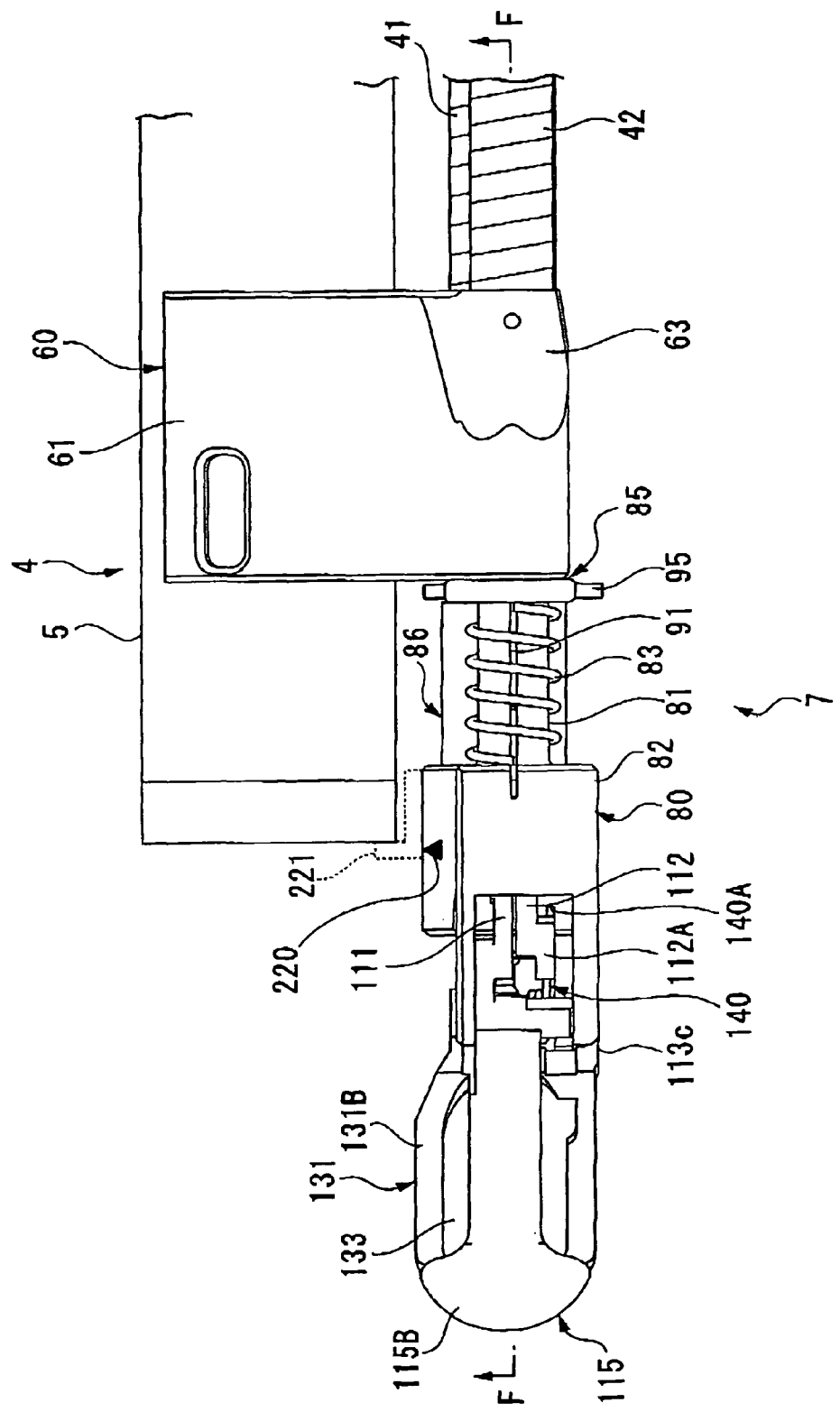
FIG. 7 is a view on arrow D in FIG. 6.
Figure 8:
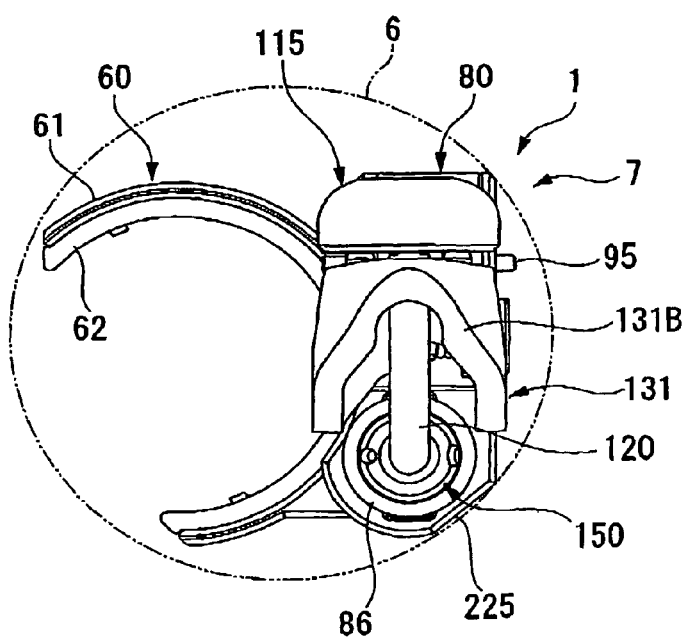
FIG. 8 is a view on arrow E in FIG. 6.

As shown in FIG. 6 to FIG. 8, a receiving portion 60 is fixed to the distal end of the insertion portion 3. As shown in FIG. 8, the receiving portion 60 has a C-shaped base 61 into which the endoscope inserting part 5 of the endoscope 4 can be inserted. Since a part of the base 61 is cut off, an outer shape obtained by combining the endoscope inserting part 5 and the suture instrument 1 together becomes small, and the diameter of the overtube 6 can be reduced. Additionally, a contact area between the receiving portion 60 and the overtube 6 can be reduced. From these, the insertion into the overtube 6 or into body cavities can be easily performed. To secure the connection strength between the base 61 and the endoscope 4, a flexible member 62 is affixed to the inner side of the base 61. The flexible member 62 additionally has a function to prevent the base 61 from damaging the endoscope 4.

As shown in FIG. 6 and FIG. 7, in the receiving portion 60, a taper portion 63 is formed at the proximal end toward which the coil sheaths 41 and 42 are pulled in. The taper portion 63 is formed to reduce the outer diameter of the receiving portion 60 toward the proximal end. As a result, the outer periphery of the base 61 is not caught by the taper portion 63 when the treatment portion 7 drawn out from the overtube 6 is again contained in the overtube 6 during manipulation.

Figure 9:
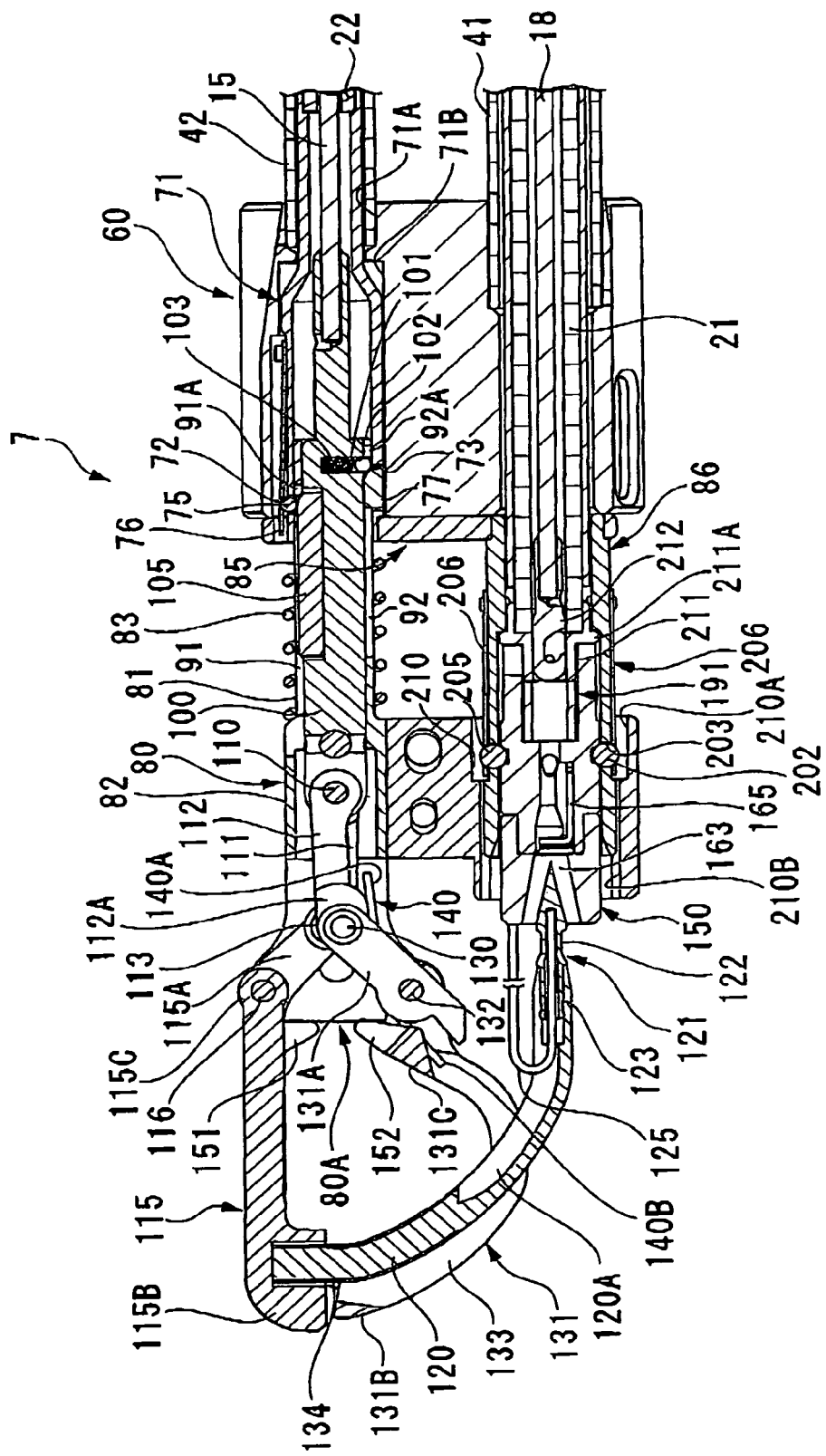
FIG. 9 is a sectional view along line F-F in FIG. 7.

As shown in FIG. 9, a cylindrical hole 71A to which the distal end of the coil sheath 42 is fixed on the outer periphery thereof is disposed in the receiving portion 60. A distal-end supporting member 71 is disposed movably back and forth in a hole 71B. The distal-end supporting member 71 extends along the axial line of the coil sheath 42. The forceps sheath 22 is fixed to the proximal end thereof, and the forceps operating wire 15 is passed through the inside thereof.

A hole 72 and a slit 73 are formed in the distal end of the distal-end supporting portion 71. The hole 72 and the slit 73 are formed on the straight line of the distal-end supporting portion 71, and an end of the slit 73 extends nearer to the proximal end than the hole 72. A pin 75 that is a first locking member (a distal-end locking member) is inserted in the hole 72. A part of the pin 75 projects into the distal-end supporting portion 71 in a state in which the pin 75 is inserted in the hole 72. The pin 75 is attached to the outer periphery of the distal-end supporting portion 71 by a leaf spring 76 serving as an urging member. The leaf spring 76 is urged in a direction in which the pin 75 is contained in the hole 72. On the other hand, an elongated release member 77 is inserted in the slit 73. The release member 77 is a second release member (a forceps release member) fixed to the distal-end supporting portion 71 by, for example, laser welding or by an adhesive. A proximal end of an elongated plate member and the distal-end supporting portion 71 in the direction of the center axis are slantingly cut.

A tube part 81 of a tip cover 80 is inserted in the distal-end supporting portion 71 from the side of the distal opening. The tip cover 80 has the tube part 81 that has the outer diameter substantially equal to the inner diameter of the distal-end supporting portion 71 and a cover body 82 formed integrally at the tip of the tube part 81. A coiled spring 83 is disposed outside the tube part 81. An urging force is applied so as to separate the cover body 82 from a bridge portion 85 fixed to the distal opening of the distal-end supporting portion 71. The bridge portion 85 extends in a direction perpendicular to the insertion direction. The tip of the distal-end supporting portion 71 is fixed to an end of the bridge portion 85, and the proximal end of a cartridge supporting member 86 described later is fixed to an opposite end of the bridge portion 85.

A plurality of slits 91, 92, and 93 are formed in the tube part 81 in the length direction. The slit 91 is formed according to the position at which the hole 72 of the distal-end supporting portion 71 is formed around the axial line of the tube part 81. The slit 91 has a width so as not to allow entry of the pin 75. However, only a base 91A of the slit 91 is increased in width, so that the tip of the pin 75 can enter the slit 91. The slit 92 is formed according to the position at which the slit 73 of the distal-end supporting portion 71 is formed around the axial line. The slit 92 has a width large enough to insert the release member 77. The base of the slit 92 extends nearer to the proximal end than the base 91A of the slit 91.

As shown in FIG. 6, the slit 93 is formed at a position where the other slits 91 and 92 are avoided. A pin 95 fixed to the bridge portion 85 is inserted in the slit 93 so as to be used as a slide guide of the tube part 81.

As shown in FIG. 9, a rod 100 that is a constituent of an opening and closing mechanism is inserted in the tube part 81 movably back and forth. The forceps operating wire 15 is fixed to the proximal end of the rod 100. A concave portion 101 extending in the radial direction is formed at a position near to the proximal end of the rod 100. A ball 102 serving as a second locking member (a forceps locking member) is inserted in the concave portion 101. The ball 102 is urged by a coiled spring 103 outwardly in the radial direction. The ball 102 can enter a large-diameter part 92A provided on the base of the slit 92 of the tube part 81, but cannot enter a more forward part than the large-diameter part 92A.

A release member 105 serving as a first release member (a distal-end release member) is provided at a position that is occupied more forwardly than the ball 102 and that is obtained by the rotation around the axial line by 180 degrees. The release member 105 projects at a position where the release member 105 coincides with the ball 102 around the rotational axis. The base of the release member 105 has a tapered surface by which the pin 75 can easily ride.

An end of each of two link members 111 and 112 is rotatably attached to the tip of the rod 100 via a pin 110. An opposite end of the link member 111 is rotatably attached to an end 115A of a forceps member 115 via a pin 113. The forceps member 115 has a bent part 115C between the end 115A of the forceps member 115 and an opposite end 115B thereof. The bent part 115C is rotatably pivoted on the tip cover 80 by means of a pin (pivot shaft) 116. A curved needle (attaching portion) 120 is fixed to the opposite end 115B of the forceps member 115. A detachable needle 121 is detachably attached to the tip of the curved needle 120. The detachable needle 121 has the pointed end part, a diameter-reduced contracted part 122 next to the pointed end part, and then a proximal end part 123. The proximal end part 123 is fitted to the curved needle 120. An end of a suture thread 125 is drawn in the proximal end part 123, and is fixed there. The contracted part 122 is formed when the suture thread 125 inserted therein is fixed while caulking concave parts formed on the detachable needle 121 from the four directions. According to this structure, the outer diameter of the detachable needle can be made smaller than a conventional detachable needle to which a suture thread is fixed by use of the knot of the suture thread. The suture thread 125 is drawn out through a slit 120A of the curved needle 120.

On the other hand, the opposite end of the other link member 112 is rotatably connected to the proximal end of an intermediate member 131A by means of a pin 130. The distal end of the intermediate member 131A is rotatably supported by the tip cover 80 via a pin 132. A forceps member 131 is rotatably pivoted on the tip cover 80 by means of the pin (pivot shaft) 132 on the side of the proximal end. A tip part 131B of the forceps member 131 is shaped like a ring having an opening 133, and is curved forwardly. A needle 134 that is inserted into tissues is fixed to the forefront of the forceps member 131.

Figure 10:
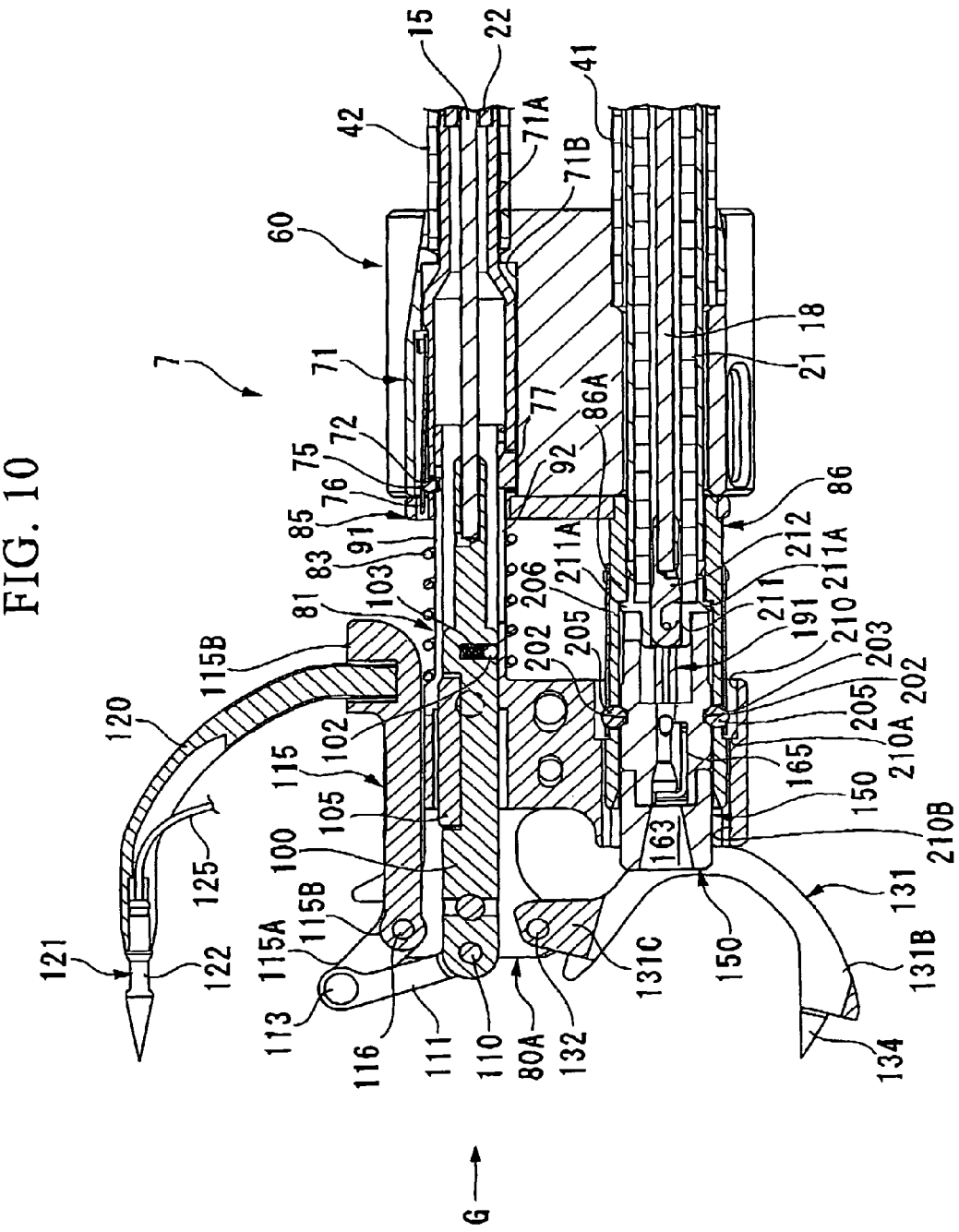
FIG. 10 is a sectional view obtained when a forceps member is opened.

As shown in FIG. 10, when the pair of forceps members 115 and 131 is opened, the tip of the detachable needle 121 attached to the curved needle 120 and the tip of the needle 134 of the forceps member 131 coincide with each other in the insertion direction. Since the needles 121 and 134 are inserted into tissues substantially simultaneously, the needles 121 and 134 do not easily come off from the tissues, and can be reliably inserted thereinto. Additionally, the needles 121 and 134 can be inserted deep thereinto.

As shown in FIG. 6, in the forceps member 131, a part 131C supported by the tip cover 80 via the pin 132 is disposed outside the tip cover 80. The tip cover 80 has a concave part 80B, and the part 131C of the forceps member 131 is supported by the concave portion 80B via the pin 1321. As shown in FIG. 7, a large difference in level does not exist at the boundary between the part 131C of the forceps member 131 and the tip cover 80, and hence the endoscope can be easily inserted into the body cavities, and the operability is improved.

Additionally, since the forceps member 131 is supported outside the tip cover 80, a space used to dispose a charging spring that urges the forceps member 131 so as to be reliably closed is secured in the tip cover 80. As shown in FIG. 7 and FIG. 9, a charging spring 140 is wound like a coil with the pin 132 provided with a clearance. When the pair of forceps members 115 and 134131 is closed, an end 140A of the charging spring 140 comes into contact with the proximal end of the intermediate member 131A. An opposite end 140B of the charging spring 140 comes into contact with the part 131C of the forceps member 131. When the pair of forceps members 115 and 131 is closed, the charging spring 140 applies an urging force so as to completely close the opposite end 131B of the forceps member 131.

Figure 11:
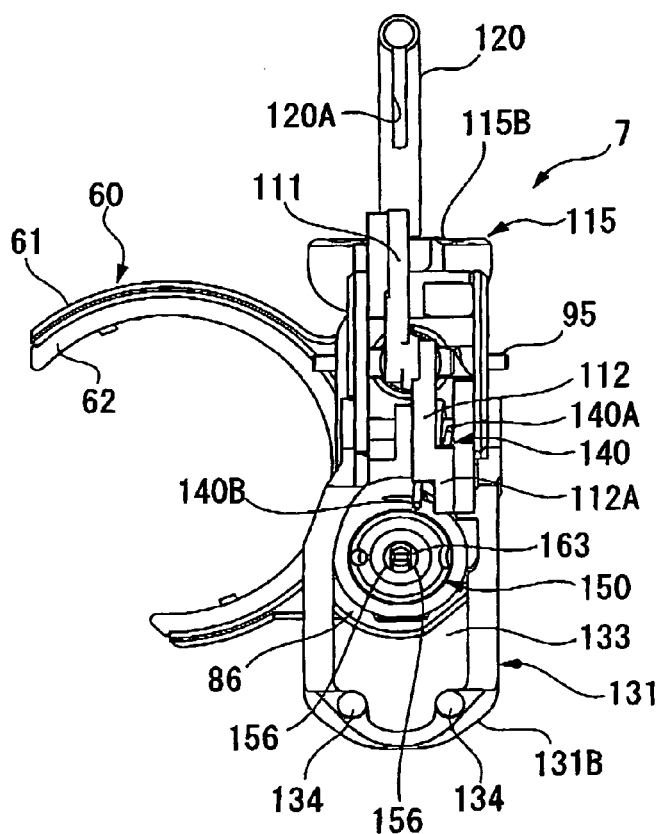
FIG. 11 is a view on arrow G in FIG. 10.

Since the charging spring 140 is wound like a coil, both of the ends 140A and 140B extend toward mutually different positions in the width direction. As shown in FIG. 11, the end 140A is disposed outside, whereas the opposite end 140B is disposed near the center. FIG. 11 shows a state in which the pair of forceps members 115 and 131 has been opened, and the charging spring 140 does not function. An opposite end 112A of the intermediate member 131A is expanded outwardly in the width direction so as to come into contact with the end 140A of the charging spring 140. On the other hand, the inside of the opposite end 112A of the intermediate member 131A is cut off, and the opposite end 112A thereof is deformed in the width direction. Since the opposite end 112A of the intermediate member 131A is structured in this way, interference between the intermediate member 131A and a casing 150 can be prevented when the casing 150 is moved back and forth. Additionally, in the structure to avoid the casing 150, adequate rigidity can be obtained by forming the deformed structure.

As shown in FIG. 6, the forceps members 115 and 131 are provided with projecting stoppers 151 and 152, respectively, that come into contact with a tip surface 80A of the tip cover 80 when the pair of forceps members 115 and 131 is completely closed. Since the stoppers 151 and 152 come into contact therewith, the forceps member 115 does not sag, and the axial line of the detachable needle 121 is not easily deviated when the pair of forceps members 115 and 131 is closed.

Next, a description will be given of the casing 150 into which the opposite end of the suture thread 125 is drawn as shown in FIG. 9 and the casing supporting portion 86 that supports the casing 150.

Figure 12:
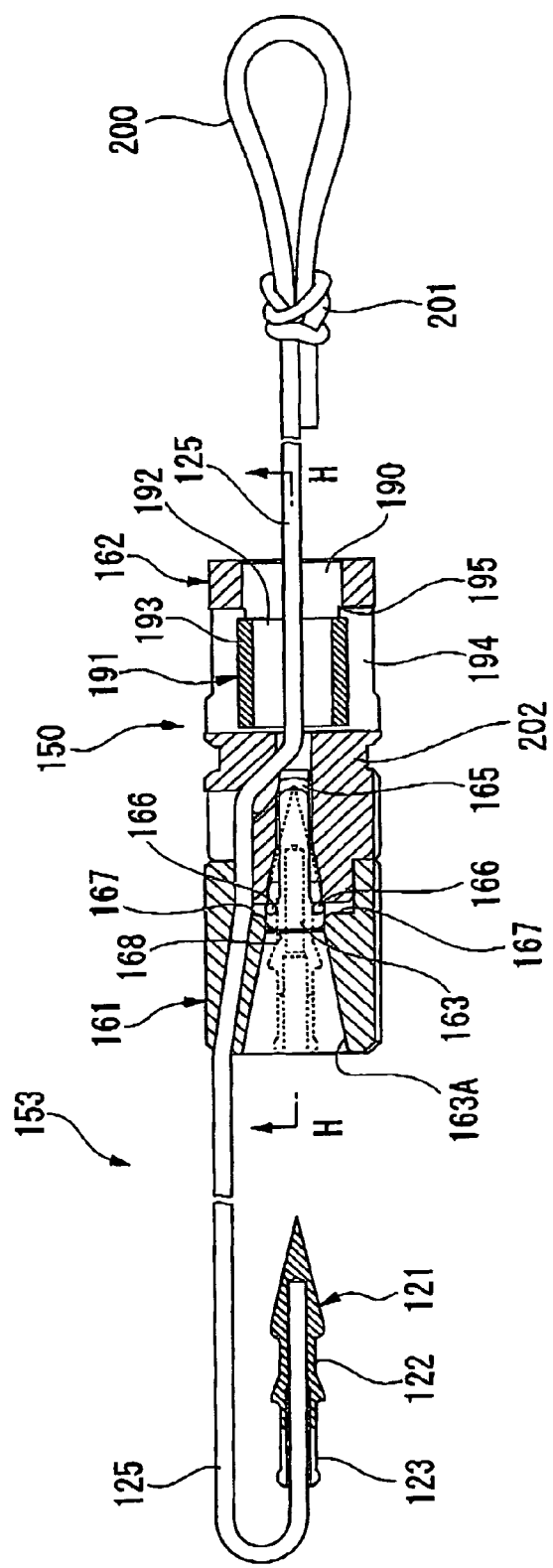
FIG. 12 is a sectional view showing a treatment instrument including a detachable needle, a casing, and a suture thread.
Figure 13:
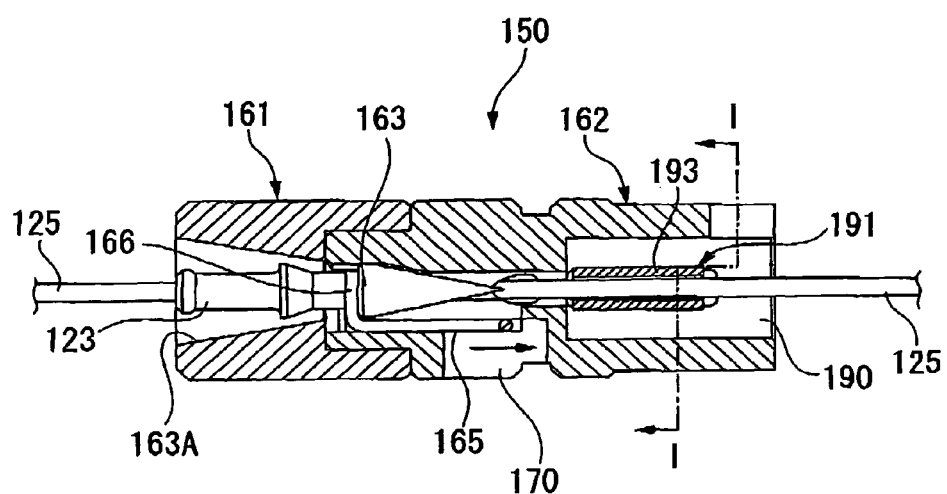
FIG. 13 is a sectional view along line H-H in FIG. 12, showing a state in which the detachable needle has been locked.

As shown in FIG. 12 and FIG. 13, the casing 150, the suture thread (string member) 125, and the detachable needle (tip member) 121 constitute a cartridge (also called a "retaining device") 153 that is retained in the body.

The casing 150 is formed by combining cylindrical members 161 and 162 together, and has a reception hole 163 into which the detachable needle 121 can be inserted. The distal end side of the reception hole 163 has a tapered surface 163A by which the axial line of the reception hole 163 and the axial line of the detachable needle 121 are allowed to easily coincide with each other. A wire spring 165, which is a needle locking member (tip-member locking member) used to prevent the detachable needle 121 from falling off, is inserted in the reception hole 163. The wire spring 165 is formed by bending a rod like the letter U and bending both ends 166 of the wire spring 165 by 90 degrees so as to become parallel in the same direction. The ends 166 of the wire spring 165 are disposed to reduce the width of the reception hole 163. In an initial state, the ends 166 of the wire spring 165 are contained in a groove 167 the width of which is greater than that of the reception hole 163. When the detachable needle 121 enters the reception hole 163, both ends 166 can be expanded. As shown in FIG. 13, when the detachable needle 121 is contained in the reception hole 163, the proximal end part 123 of the detachable needle 121 is completely contained in the casing 150. Therefore, tissues are never damaged by the proximal end part 123 of the detachable needle 121.

Polyphenylsulfone, polyphthalamide, polyether ether ketone, titanium alloy, or pure titanium can be mentioned as a material of the casing 150. If the casing 150 is made of polyphenylsulfone, polyphthalamide, or polyether ether ketone, the casing 150 does not easily undergo a change in quality in the living body, because they are superior in chemical resistance and acid resistance. Since these materials are also superior in welding, an assembling operation can be performed by use of ultrasonic wave welding or laser welding. Pure titanium or titanium alloy is superior in biocompatibility.

When the detachable needle 121 is contained in the casing 150, the wire spring 165 pinches the contracted part 122 of the detachable needle 121. If an operator intends to pull out the detachable needle 121 from the casing 150, the wire spring 165 is moved and slid together therewith, and the end 166 enters a narrow part 168 (see FIG. 12) on the distal-end side. Since the end 166 cannot be opened here, the wire spring 165 serves as a stopper, and prevents the detachable needle 121 from falling off. If the operator intends to pull out the detachable needle 121 from the casing 150, it is recommended to insert a release device into a release hole 170 formed in the side of the casing 150 and then return the wire spring 165 to the proximal end side as shown by the arrow in FIG. 13. As a result, the end 166 returns to the groove 167, whereby both ends 166 can be opened while being pushed. Therefore, the detachable needle 121 can be pulled out from the casing 150 by pulling the detachable needle 121 in a state of fixing the position of the wire spring 165.

Figure 14:
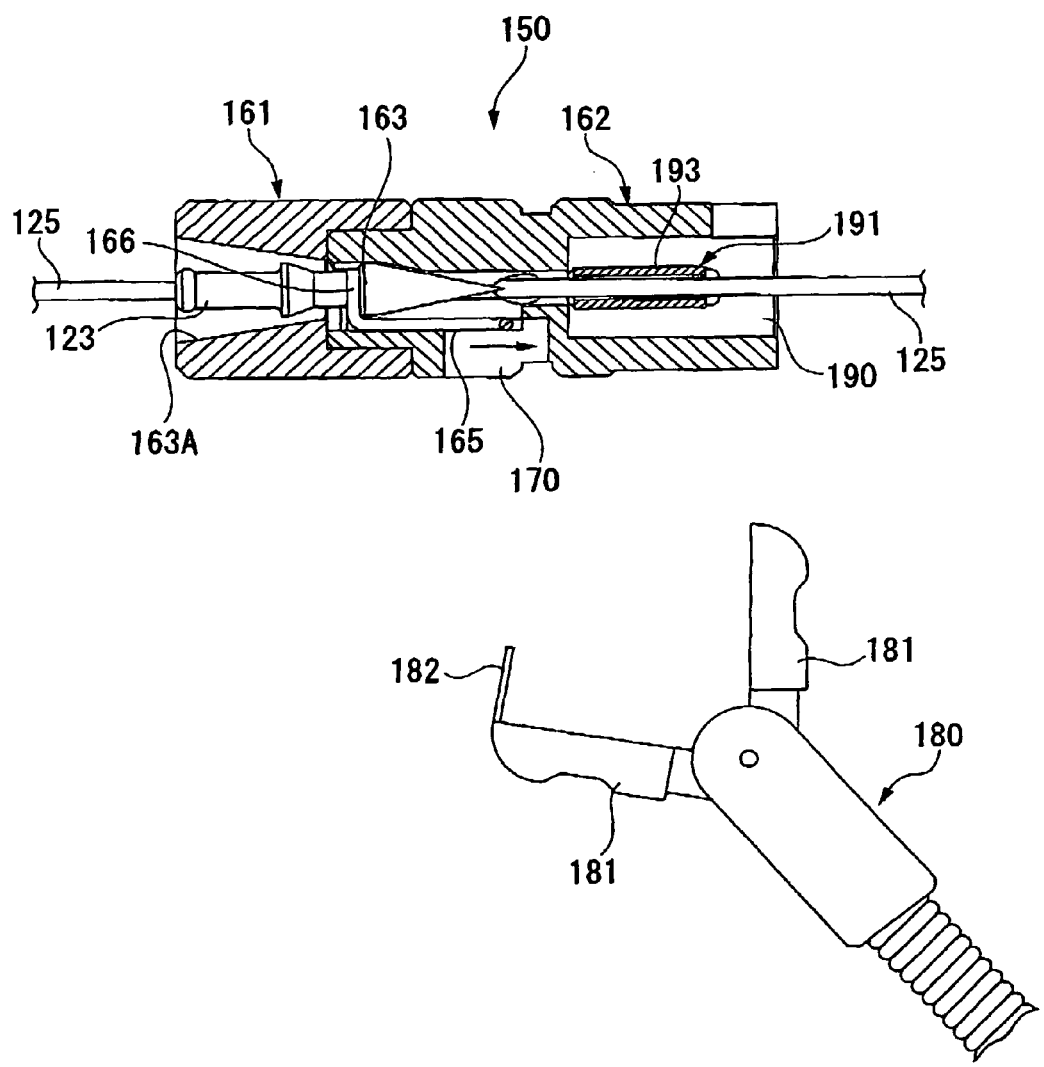
FIG. 14 is a view showing an example of a device for releasing the locking of the detachable needle.

For example, a device having a structure in which a holding member 181 of a forceps 180 is provided with a release pin 182 can be mentioned as the release device as shown in FIG. 14. If the operator inserts the release pin 182 through the release hole 170 by operating the instrument from the proximal end thereof, the detachable needle 121 can be pulled out from the casing 150 even during the manipulation. The form of the release device is not limited to that in FIG. 14. Any type of device can be employed as long as the device can be inserted through the release hole 170, and the wire spring 165 can be moved toward the proximal end side.

Figure 15:
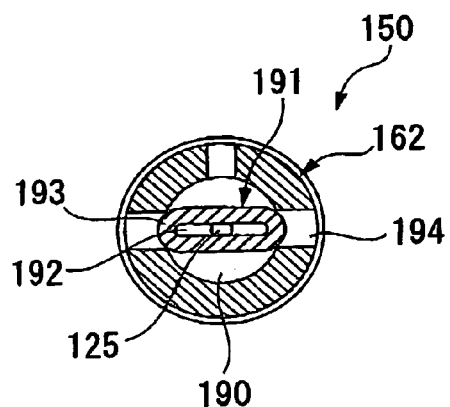
FIG. 15 is a sectional view taken along line I-I in FIG. 13.

As shown in FIG. 12 and FIG. 15, the suture thread 125 drawn into the casing 150 is pulled into the reception hole 163 from a position nearer to the proximal end than an area that the detachable needle 121 enters on the midway of the reception hole 163. The proximal end of the reception hole 163 leads to a large-diameter hole 190 formed in the surface of the proximal end of the casing 150. A brake portion (thread locking member) 191 is disposed inside the hole 190. The brake portion 191 has a flat shape obtained by winding a metallic plate 193 around an elastic member 192 through which the suture thread 125 is passed and then flattening the metallic plate 193. Predetermined sliding friction is generated between the suture thread 125 and the brake portion 191. The casing 150 has a slit 194 passing through the casing 150 in the radial direction. The brake portion 191 is loosely fitted to the slit 194. Since a step 195 formed between the hole 190 and the slit 194 functions as a stopper of the brake portion 191, the brake portion 191 never projects out of the casing 150 even when the brake portion 191 is pulled in the length direction of the suture thread 125. The brake portion 191 makes it possible to generate predetermined sliding friction when the casing 150 is moved between an end of the suture thread 125 and the opposite end thereof, and, as a result, the movement of the casing 150 is restrained.

Herein, the end of the suture thread 125 pulled out from the surface of the proximal end of the casing 150 forms a loop (hook catching portion) 200. A double, drawn-untied knot 201 is employed to form the loop 200. Since the double, drawn-untied knot 201 can make a knot of the loop 200 small, the loop 200 can be easily inserted into the hook sheath 21 even if the inner diameter of the hook sheath 21 is small.

As shown in FIG. 10, the casing 150 is contained in the casing supporting member 86. A ball (a third locking member, a casing locking member) 205 that is inserted through the hole 203 of the casing supporting member 86 is engaged with each annular concave portion 202 formed on the side of the casing 150. The ball 205 is urged to be fastened to the casing 150 by a leaf spring 206 serving as an urging member fixed to the casing supporting member 86. It is permissible to unite the ball 205 and the leaf spring 206 together by use of laser welding or an adhesive. The end of the casing supporting member 86 is inserted movably back and forth in a guide hole 210 used as a guide member of the tip cover 80. The guide hole 210 has its proximal end whose diameter has been increased. The ball 205 can be moved outwardly in the radial direction in a part 210A widened as shown in FIG. 9. A distal end part 210B is smaller in the diameter of the guide hole 210 than the diameter-increased part 210A, and hence the ball 205 cannot be moved outwardly in the radial direction.

In the casing supporting member 86, a distal claw portion 211 attached to the hook sheath 21 is fitted into the hole 190 of the casing 150. The distal claw portion 211 has a flange 211A that serves as a stopper by coming into contact, from the distal end side, with a step 86A formed on the inner periphery of the casing supporting member 86. A hook 212 is contained in the through-hole thereof. The hook 212 is fixed to the tip of the hook operating wire 18 passed movably back and forth through the hook sheath 21. The loop 200 (see FIG. 12) formed on the opposite end of the suture thread 125 is caught by the hook 212. Conventionally, an inner tube has been provided between the hook sheath 21 and the casing supporting portion 86. However, in this embodiment, the structure of the instrument is simplified by excluding the inner tube. As a result, component cost can be reduced, and the number of assembling steps can be reduced.

As shown in FIG. 7, a mark 220, which is used as a restriction part by which the endoscope 4 is positioned in the insertion direction, is provided on the side of the tip cover 80 of the treatment portion 7. A rigid part of the distal end of the endoscope 4 and a rigid part of the treatment portion 7 can be overlapped with each other in the insertion direction by putting the distal end of the endoscope 4 onto the mark 220. Conventionally, the distal end of the endoscope 4 has been positioned on the receiving portion 60, and hence the whole length of the rigid part is equal to the sum of the length of the treatment portion 7 and the length of the rigid part of the endoscope 4. Therefore, disadvantageously, it has been difficult to achieve excellent insertability into the overtube 6 or into the living body. However, in this embodiment, the length of the rigid part is shortened, and hence insertability is improved. Additionally, since the endoscope 4 is disposed nearer to the distal end, the tip cover 80 or the other elements do not block the visual field of an observation device of the endoscope 4. Therefore, a sufficient visual field can be obtained. A plate member 221 caused to abut against the surface of the end of the endoscope 4 may be used as a restricting member instead of the mark 220, and may be protruded from the tip cover 80 as shown by the broken line in FIG. 7. Additionally, as shown in FIG. 8, an inclined surface 225 is formed by slantingly cutting the corner of the tip cover 80. The inclined surface 225 makes it possible to facilitate a back-and-forth operation, because the suture instrument 1 is contained within the inner diameter of the overtube 6 shown by the phantom line in FIG. 8.

Next, the operation of this embodiment will be described. Although the following description is concerned with a case in which an incision formed in a stomach wall is sutured, a target region is not limited to the stomach wall. Hollow organs, such as the esophagus, duodenum, small intestine, large intestine, womb, or bladder may be targeted. Additionally, a natural opening through which the endoscope 4 is inserted is not limited to the mouth. The nose or anus may be used as the natural opening. Additionally, the treatment instrument of the present invention may be used to suture a mucous-membrane defective part or a perforated part generated by hemostasis or an ulcer.

The endoscope inserting part 5 of the endoscope 4 is passed through the scope holder 26, the valving element 50, and the receiving portion 60 in this order, and then the surface of the end of the endoscope 4 is allowed to coincide with the mark 220. To firmly fix the endoscope 4 to the suture instrument 1, the end of the endoscope 4 and the receiving portion 60 may be fastened together by, for example, a tape. Thereafter, the cartridge 153 is set at a desired position of the suture instrument 1. The overtube 6 is inserted from the mouth of a patient to the neighborhood of the cardiac orifice of the stomach or into the stomach by use of another endoscope. Thereafter, the suture instrument 1 fixed to the endoscope 4 via the overtube 6 is inserted into the stomach.

In the interior of the stomach, the position of the incision of a tissue that is a target region is confirmed by an observation device of the endoscope 4. Since the end of the endoscope 4 is disposed nearer to the distal end of the suture instrument than a conventional endoscope, the visual field is not easily blocked by the suture instrument 1, so that the incision of the tissue and the detachable needle 121 can come within the same visual field.

Figure 16:
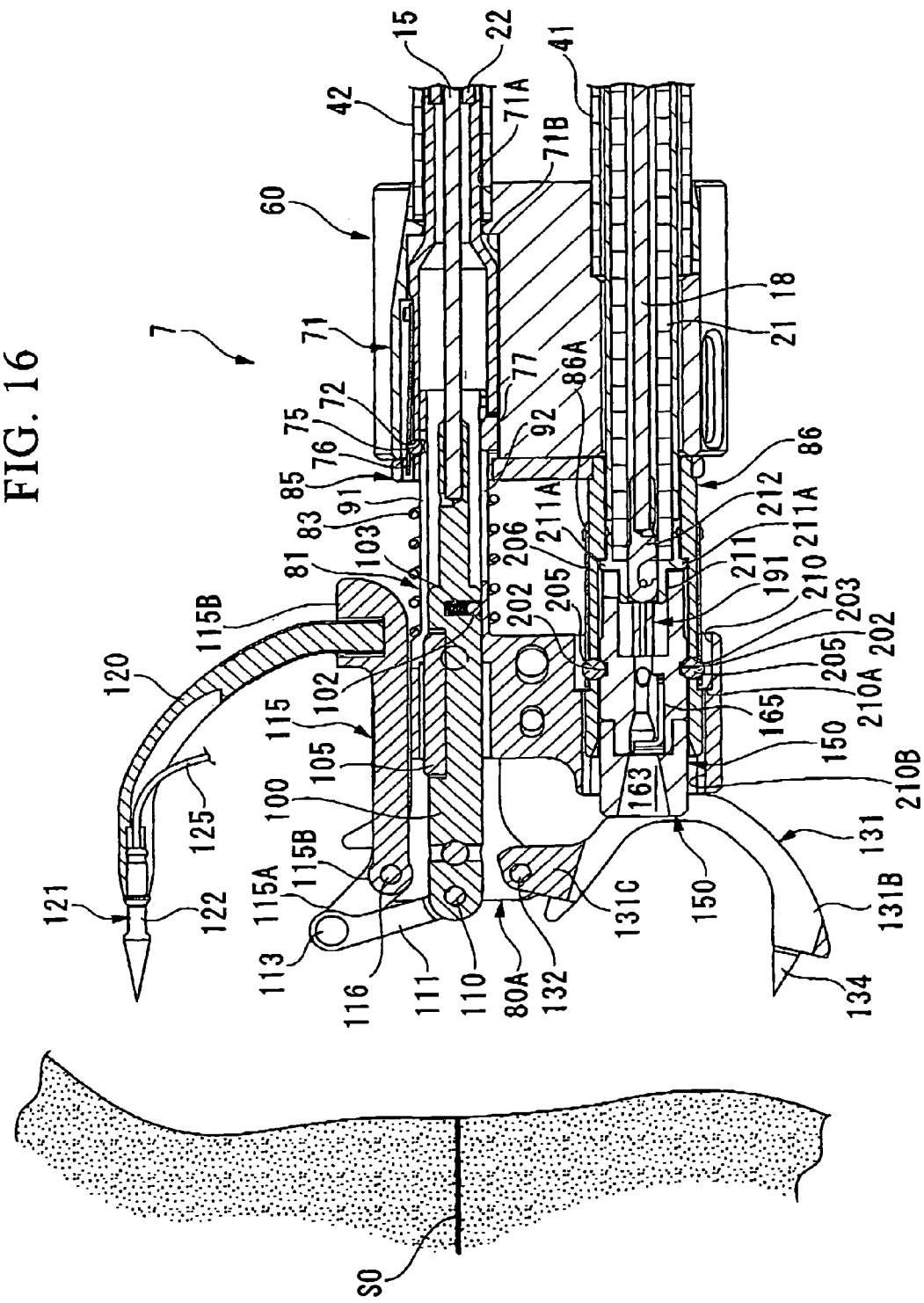
FIG. 16 is a sectional view for illustrating a suture method, showing a state in which a forceps member has been opened toward an incision.

Thereafter, the pair of forceps members 115 and 131 is opened in the interior of the stomach before suturing. In more detail, an operator extends the forceps operating portion 13 of the control portion 2. The forceps operating wire 15 is then extended, and the link members 111 and 112 connected to the rod 100 allow the forceps members 115 and 131 to pivot on the pins 106 and 132 and be opened. As shown in FIG. 16, when the thus opened forceps members 115 and 131 are allowed to approach the incision SO that is a target region, the pair of forceps members 115 and 131 is closed in such a way as to pinch tissues around the incision SO with the forceps members 115 and 131.

Figure 17:
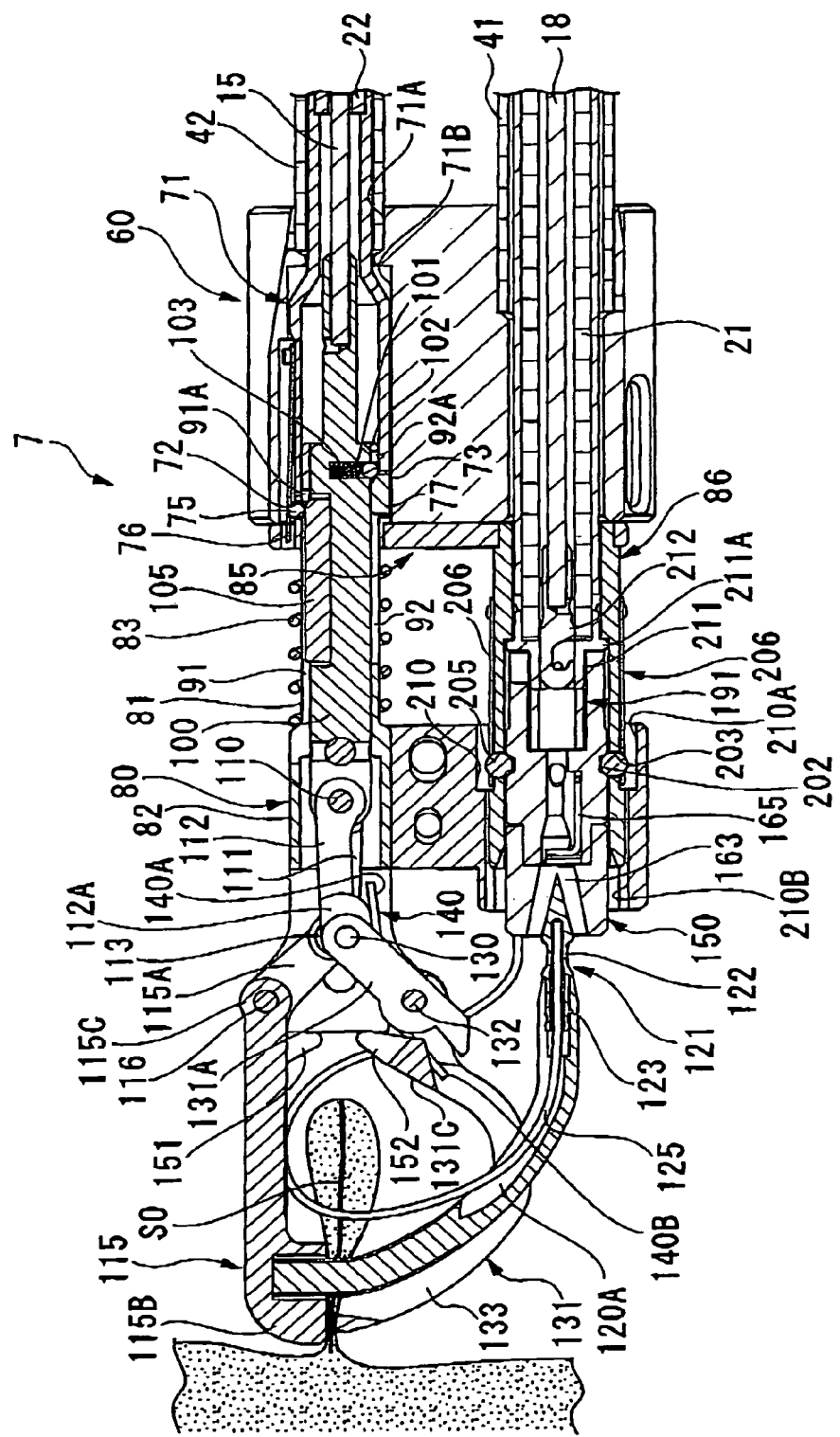
FIG. 17 is a sectional view showing a state in which the forceps member has been closed so as to pinch tissues including the incision.

When the operator allows the forceps operating portion 13 of the control portion 2 to recede therefrom, the forceps operating wire 15 recedes, and the link members 111 and 112 are pulled into the tip cover 80, so that the forceps members 115 and 131 pivot on the pins 106 and 132, respectively, and are closed. The needle 134 of the forceps member 131 is then inserted into the tissue, and presses the tissue against the incision SO. On the other hand, the curved needle 120 of the forceps member 115 is inserted into a tissue on the opposite side of the forceps member 131 with the incision SO therebetween, and is protruded toward the casing 150 through the tissue drawn in by the forceps member 131 across the incision SO. As a result, as shown in FIG. 17, the curved needle 120 and the suture thread 125 are passed through the incision SO.

If the incision SO is relatively large and cannot be pinched by a single suturing operation, it is permissible to first make a puncture in an end of the incision SO, then make a gap between the detachable needle 121 and the needle 134 by widening the curved needle 120 to the extent of about a half, then take a tissue on the opposite side of the incision SO into the gap, and perform a suturing operation while inserting the needle there.

Figure 18:
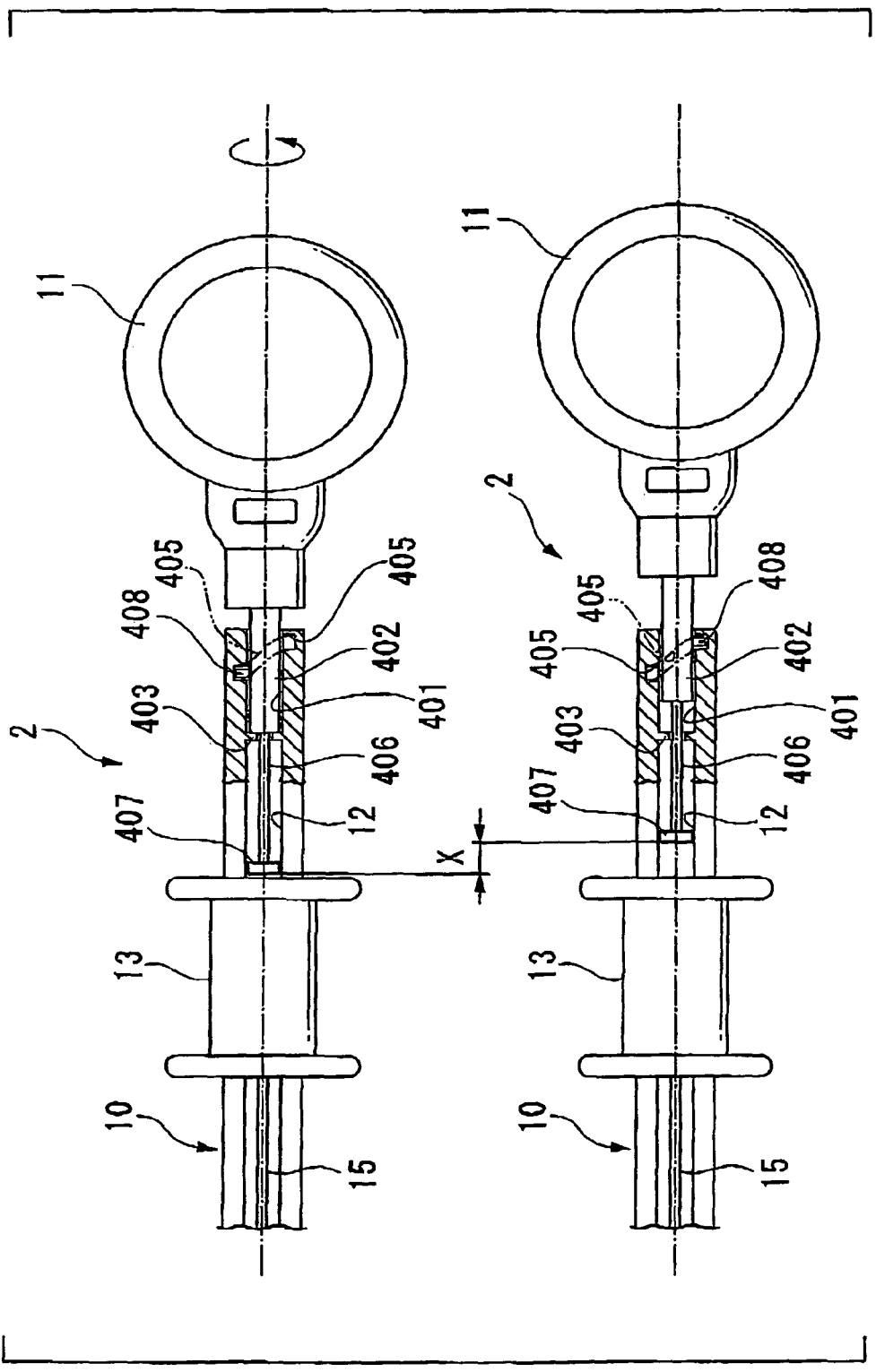
FIG. 18 is a view showing one aspect of the control portion that can reliably perform a needle-inserting operation twice.

If the tissue is hard at this time, the detachable needle 121 cannot be easily inserted through the tissue, and the forceps operating portion 13 cannot be stopped at a position at which the detachable needle 121 arrives through the tissue, because a large force is applied onto the forceps operating portion 13. Accordingly, the detachable needle 121 is often moved, as a serial operation, to a position at which the detachable needle 121 is engaged with the casing 150. If so, the incision cannot be sutured by a twice-inserting operation as described above. To reliably perform the twice-inserting operation, it is recommended to structure the control portion 2 as shown in FIG. 18. In the control portion 2, a hole 401 leading to the slit 12 is formed in the proximal end of the control body 10, and a cam rod 402 extended to the end of the ring 11 is inserted in the hole 401. An abutment portion 403 is disposed at the end of the hole 401 in such a way as to reduce the opening diameter. A spiral cam groove 405 is formed on the inner periphery of the hole 401. The cam groove 405 extends in the circumferential direction with a length greater than at least a semicircle (180 degrees). Further, a rod 406 that can pass through the abutment portion 403 extends from the cam rod 402 toward the distal end. The rod 406 is inside the slit 12, and a stopper 407 is disposed at the tip of the rod 406 so that the stopper 407 can come into contact with the forceps operating portion 13. Further, on the outer periphery of the cam rod 402, a pin 408 extends outwardly in the radial direction. The pin 408 is inserted in the cam groove 405, and the ring 11 is engaged with the control body 10 with the pin 408 therebetween.

In the control portion 2, the forceps operating portion 13 can be pulled until the forceps operating portion 13 comes into contact with the stopper 407. When the ring 11 is rotated from the position shown in FIG. 18 by 180 degrees, the rotational motion of the pin 408 rotating together with the ring 11 is transformed into the linear motion of the ring 11 by the cam groove 405, so that the ring 11 recedes. The stopper 407 formed integrally with the ring 11 recedes by, for example, a movement amount X. Since the stopper 407 recedes, the forceps operating portion 13 can further recede by the movement amount X. If the position obtained at this time is set as a position to which the tip cover 80 is moved until the detachable needle 121 is engaged with the casing 150, and if the first position of the stopper 407 is set as a first position for a twice-inserting operation, the twice-inserting operation will be reliably performed.

Figure 19:
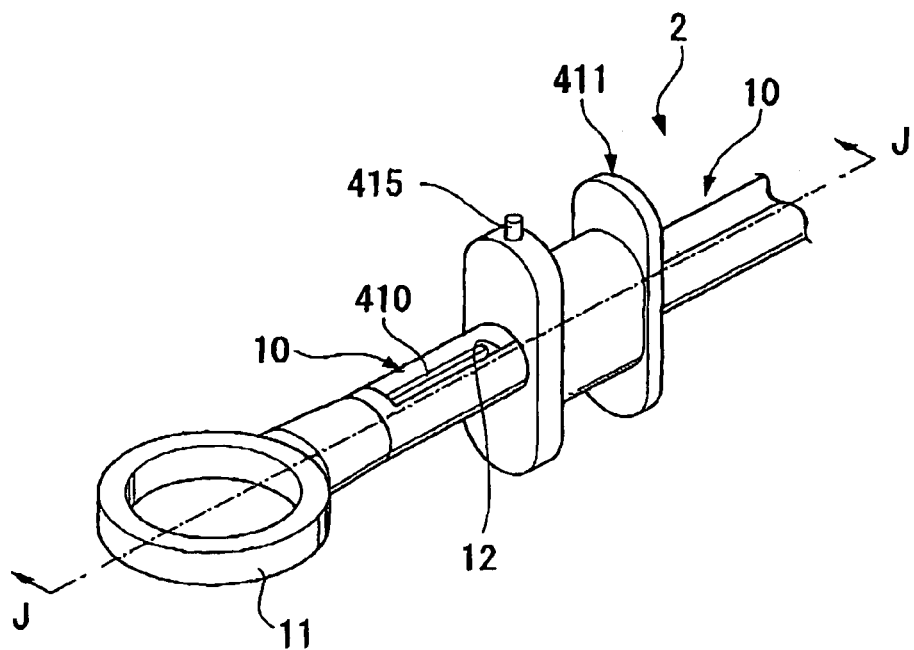
FIG. 19 is a view showing another aspect of the control portion that can reliably perform a needle-inserting operation twice.
Figure 20:
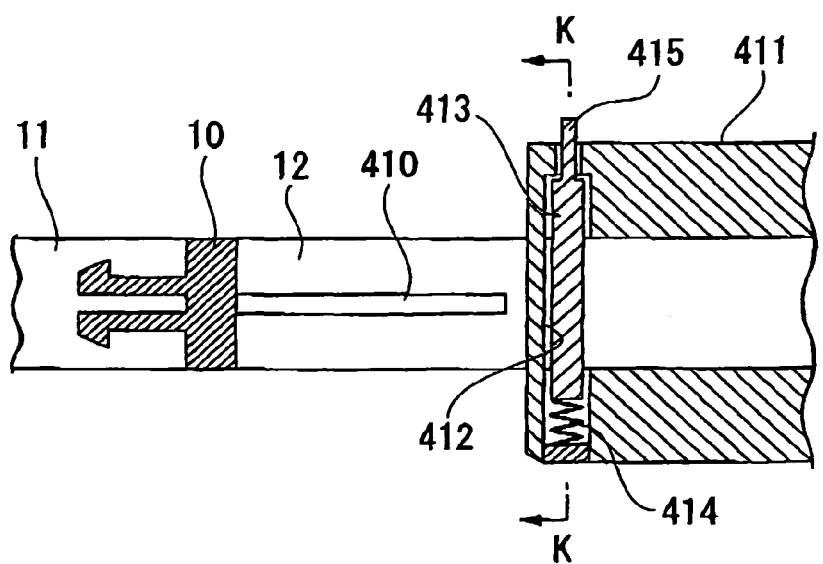
FIG. 20 is a sectional view along line J-J in FIG. 19.
Figure 21:
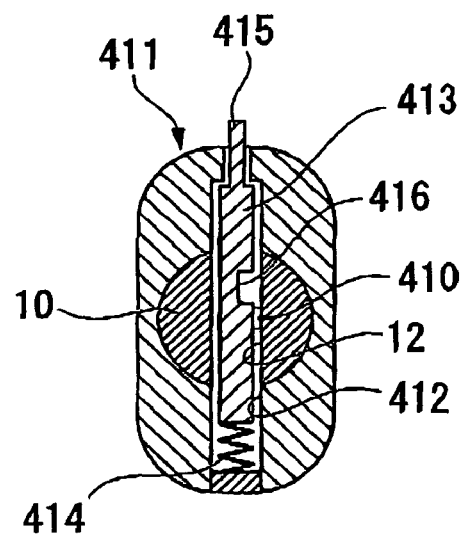
FIG. 21 is a sectional view along line K-K in FIG. 20.
Figure 22:
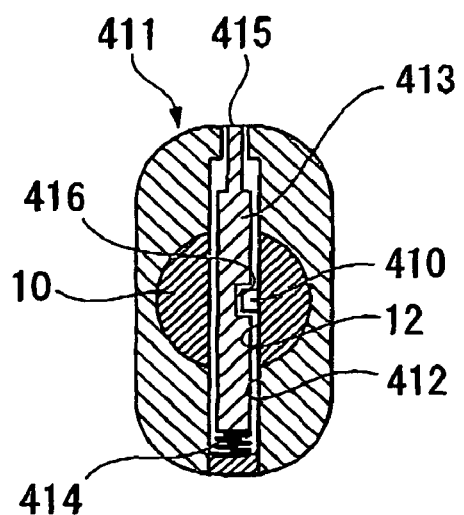
FIG. 22 is a view showing a state in which a stopper releasing button has been pushed from the state in FIG. 21.

Another aspect is shown in FIG. 19. As shown in FIG. 19, an obstacle rail 410 is disposed with a predetermined length in the length direction on the inner surface of the slit 12 of the control body 10 so as to have a ridge toward the inside of the slit 12. A forceps operating portion 411 is attached to the slit 12 slidably back and forth. The forceps operating portion 411 is a slider by which the pair of forceps members 115 and 131 is opened or closed. As shown in FIG. 20, a hole 421 perpendicular in the sliding direction is provided inside. A stopper member 412 is inserted in the hole 421. The stopper member 412 is urged by a coiled spring 414, which is an elastic member, toward an opening narrowed in the hole 412. The end of the stopper member 412 projects from the forceps operating portion 411, and is used as a stopper releasing button 415. The stopper member 412 has a cut 416 formed in the side thereof. As shown in FIG. 21, the cut 412 is sufficiently larger than the obstacle rail 410. However, since the position of the cut 416 does not coincide with the position of the obstacle rail 410 in a natural state, the forceps operating portion 411 can recede only until a stopper 413 comes into contact with the obstacle rail 410. As shown in FIG. 22, when the stopper releasing button 415 is pushed, the stopper 413 is moved in proportion to the shrinkage of the coiled spring 414, and the position of the cut 416 coincides with the position of the obstacle rail 410. Since it becomes possible to avoid the obstacle rail 410 by means of the cut 416, the forceps operating portion 411 can be allowed to further recede toward the ring 11. The movement amount of the forceps operating portion 411 can be controlled by allowing the operator to push the stopper releasing button 415 provided at the end of the stopper 413 as described above, and hence the twice-inserting operation can be reliably performed.

When the curved needle 120 and the suture thread 125 are passed through the incision SO, the forceps member 131 is urged by the urging force of the charging spring 140 in the closing direction, and the needle 134 firmly bites into the tissue. Further, the stoppers 151 and 152 of the forceps members 115 and 131 are pushed against the tip surface 80A of the tip cover 80. As a result, the forceps members 115 and 131 are prevented from sagging, and the axial line of the detachable needle 121 and the axial line of the casing 150 substantially coincide with each other.

Figure 23:
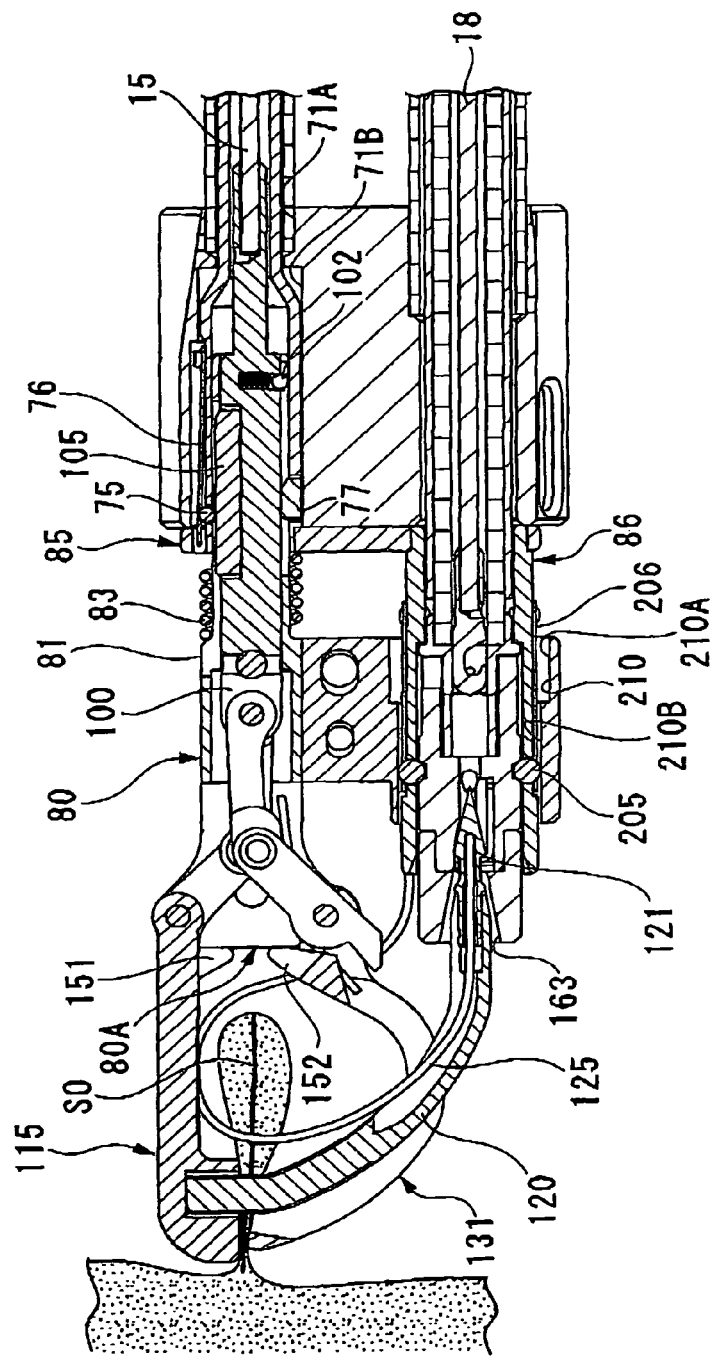
FIG. 23 is a sectional view showing a state in which the detachable needle has been inserted into the casing by pulling a tip cover and the forceps member.

When the pair of forceps members 115 and 131 is completely closed, or immediately before the pair of forceps members 115 and 131 is completely closed, the tapered surface of the release member 105 of the rod 100 pulled into the tube part 81 of the tip cover 80 pushes the pin 75 up. The engagement between the tube part 81 and the distal-end supporting portion 71 is released by pushing the pin 75 up. As a result, the tip cover 80 can be pulled into the distal-end supporting portion 71. Therefore, when the forceps operating wire 15 is allowed to further recede as shown in FIG. 23, the tip cover 80 recedes while compressing the coiled spring 83, and the forceps members 115 and 131, which are connected to the tip cover 80 by means of the pins 116 and 132 and the stoppers 151 and 152, recede. At this time, the ball 102 of the tube part 81 enters the large-diameter part 92A beyond the release member 77, and the tube part 81 and the rod 100 are connected together.

On the other hand, the casing 150 is held by the casing supporting member 86, and is not moved. Moreover, the outer periphery of the ball 205 engaged with the casing 150 is covered with the small-diameter part 210B of the guide hole 210 by allowing the tip cover 80 to recede, and hence the ball 205 cannot be moved outwardly in the radial direction. As a result, in a state of preventing the movement of the casing 150, the detachable needle 121 attached to the tip of the curved needle 120 is inserted in the casing 150. In the reception hole 163, the detachable needle 121 is locked to the casing 150 by the wire spring 165.

When the forceps operating wire 15 is completely pulled, the forceps operating portion 13 is extended. The tip cover 80 starts moving to the original position by the restoring force of the coiled spring 83 disposed outside the tube part 81. At this time, the tip cover 80 and the rod 100 are extended together since the tube part 81 and the rod 100 are connected together by means of the ball 102 entering the large-diameter part 92A of the slit 92. Therefore, the pair of forceps members 115 and 131 is extended without being opened, and the curved needle 120 attached to the forceps member 115 makes a parallel movement so as to recede from the casing 150.

Figure 24:
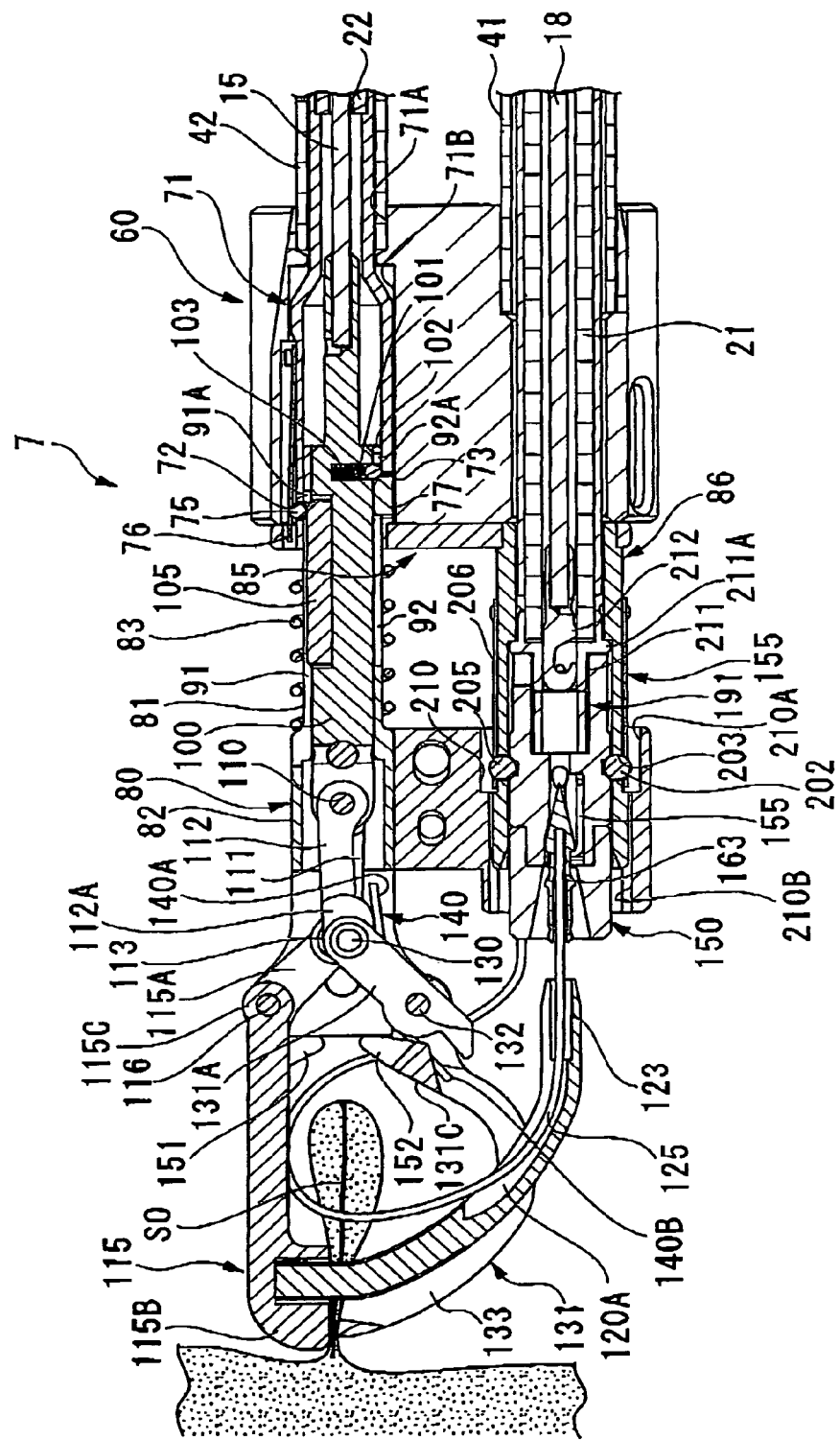
FIG. 24 is a view showing a state in which the detachable needle contained in the casing has been detached from a curved needle by returning the tip cover and the forceps member toward the distal end.
Figure 25:
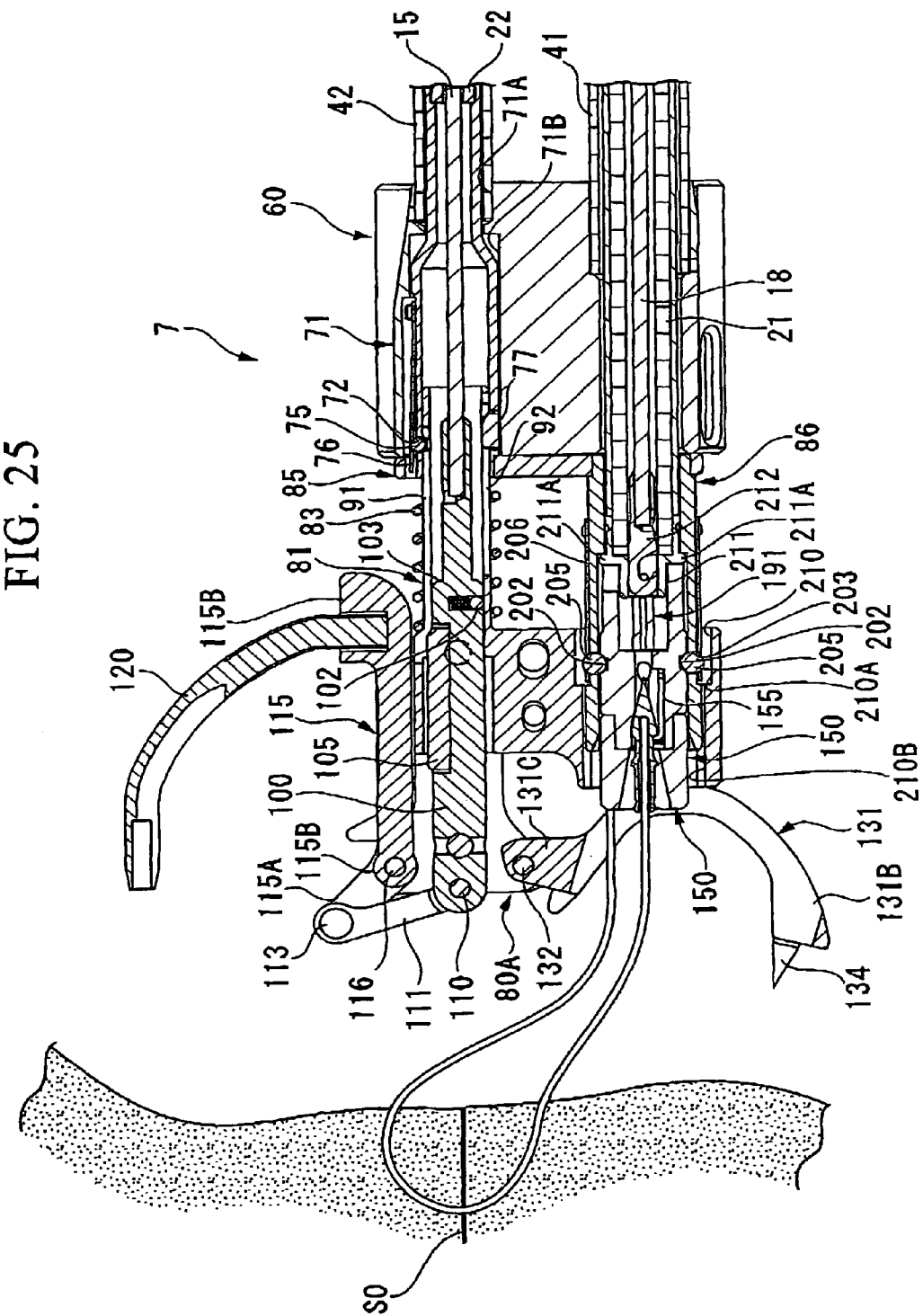
FIG. 25 is a view showing a state in which the forceps member has been opened after detaching the detachable needle from the curved needle.

The detachable needle is disengaged from the curved needle 120 by this parallel movement. As shown in FIG. 24, the detachable needle 121 stays while being contained in the casing 150, and the curved needle 120 recedes from the casing 150. Since the pair of forceps members 115 and 131 has not yet opened at this time, interference never occurs between the curved needle 120 and the casing 150. Thereafter, the ball 102 proceeding together with the tube part 81 of the tip cover 80 is brought into contact with the release member 77, and is pushed into the rod 100 by the tapered surface of the proximal end of the release member 77. Thereby, the engagement between the rod 100 and the tube part 81 is released, and the rod 100 becomes capable of proceeding to the tip cover 80. As a result, when the forceps operating portion 13 is extended, the pair of forceps members 115 and 131 can be opened. As shown in FIG. 25, the curved needle 120 is pulled out from the tissue by opening the pair of forceps members 115 and 131. The suture thread 125 remains like a loop while being passed through the tissue.

Figure 26:
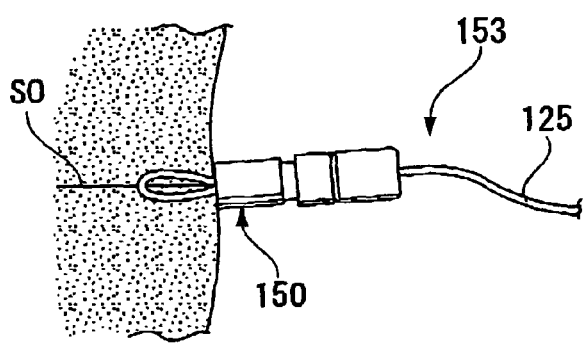
FIG. 26 is a view showing a state in which the treatment instrument is retained while the incision has been sutured.

When the suture thread 125 is tightened, the hook sheath 21 is extended. The hook sheath 21 pushes the distal claw portion 211, and the distal claw portion 211 pushes the casing 150 from the tip cover 80 toward the tissue. Since the tip cover 80 has returned to the original position, the diameter-increased part 210A of the guide hole 210 is present around the ball 205, and the ball 205 is disengaged from the concave portion 202 by the elastic deformation of the leaf spring 206, so that the engagement between the casing 150 and the casing supporting member 86 is released. When the casing 150 is protruded from the casing supporting member 86, the hook operating portion 14 is allowed to recede, and the hook 212 is allowed to recede. Since the suture thread 125 engaged with the hook 212 is pulled out, the loop of the suture thread 125 passing through the tissue is narrowed down. Since the handle 16 of the hook operating portion 14 can be pulled beyond the forceps operating portion 13, the suture thread 125 can be pulled out until the casing 150 is brought into contact with the tissue. As a result, as shown in FIG. 26, the incision SO is sutured by the cartridge 153. In a state in which the incision SO has been sutured, the cartridge 153 is retained in the body by releasing the engagement of the hook 212 or by cutting the suture thread 125 extending from the casing 150 by use of a known thread-cutting treatment device being passed through an operating channel of the endoscope 4.

In this embodiment, the structure is formed so that the engagement between the distal-end supporting portion 71 and the tip cover 80 can be released by providing the pin 75 that is a first locking member in the process of allowing the forceps operating wire 15 to recede. Therefore, the detachable needle 121 can be inserted into the casing 150 in accordance with an operation in which the pair of forceps members 115 and 131 is closed while pulling the forceps operating wire 15. A conventional control portion is complex in structure, and requires much skill in operating. However, in this embodiment, the work including the engagement of the detachable needle 121 can be achieved by a series of operations of the forceps operating portion 13, and hence the instrument can be easily operated. In other words, for example, in the treatment instrument described by US2003-0181924A1, the hook sheath holding the casing must be moved back and forth to engage the detachable needle with the casing. To do so, the control portion must be shifted from one hand to the other. Additionally, to engage the detachable needle with the casing, the detachable needle and the center axis in the longitudinal direction of the casing must coincide with each other. Therefore, an operator must confirm this coincidence during an operation. In contrast, in this embodiment, since the engagement between the distal-end supporting portion 71 and the tip cover 80 is released when a state in which the tip of the detachable needle 121 can be engaged with the casing 150 is reached, the detachable needle 121 can be inserted into the casing 150 in response to the closing motion of the pair of forceps members 115 and 131. Therefore, operability is improved. In this embodiment, the suture instrument is disclosed as an example of a treatment instrument. However, without being limited to this, the present invention can be applied to biopsy forceps or grasping forceps that are different in shape from the forceps members 115 and 131. If the present invention is applied to biopsy forceps, it will become possible to perform the operation of pinching tissues and the operation of removing the tissues, as a series of operations, by an operation performed on the side of the proximal end of the instrument. If the present invention is applied to grasping forceps, it will become possible to perform the operation of pinching tissues and the operation of transferring the tissues, as a series of operations, by an operation performed on the side of the proximal end of the instrument.

Additionally, the structure is formed so that the link mechanism of the forceps members 115 and 131 and the tip cover 80 can be extended together by providing the ball 102 that is a second locking member before the pair of forceps members 115 and 131 is opened. Therefore, the pair of forceps members 115 and 131 can be kept closed until the curved needle 120 is completely disengaged from the casing 150. Since the possibility that interference will occur between the curved needle 120 and the casing 150 is removed, the pair of forceps members 115 and 131 is reliably opened and closed. Additionally, both the disengagement of the detachable needle 121 from the curved needle 120 and the opening motion of the pair of forceps members 115 and 131 are accomplished by a series of operations of the forceps operating portion 13, and hence the instrument can be easily operated.

Since the ball 205 by which the casing 150 and the casing supporting member 86 are engaged together is provided as a third locking member, and since the engagement of the ball 205 is controlled by the guide hole 210 of the tip cover 80, the casing 150 can be reliably fixed, and the detachable needle 121 can be easily engaged with the casing 150.

Since the stoppers 151 and 152 that are brought into contact with the tip surface 80A of the tip cover 80 are provided on the forceps members 115 and 131, the deviation of the axis of the curved needle 120 can be prevented when the pair of forceps members 115 and 131 is closed. If the deviation of the axis of the curved needle 120 occurs, it will become difficult to insert the detachable needle 121 into the casing 150 or to detach the detachable needle 121 from the curved needle 120. However, in this embodiment, these problems are solved.

Since the movement control portion 25 and the scope holder 26 are provided in the path of the insertion portion 3, and since only the hook sheath 21 or both of the sheaths 21 and 22 are formed to simultaneously move back and forth, the control portion can be more easily operated than a conventional control portion, and the sheath that is moved back and forth by an operator can be easily imagined, thus making it easy to become skillful in operating. Additionally, since the movement control portion 25 is away from the control body 10, it is easy to share the operations.

Since the control portion (the forceps operating portion 13) that operates the forceps members 115 and 131 and the other control portion (the hook operating portion 14) that operates the hook 212 are integrally provided in the control portion 2, the control portions can be made compact, and can be easily handled. Since the hook operating portion 14 is disposed on the side of the distal end of the instrument, and since the forceps operating portion 13 is formed to enter the space between the handles 16, the stroke of the hook operating portion 14 can be enlarged, and the suture thread 125 can be easily tightened.

Various modifications of the suture instrument 1 will be shown hereinafter.

Figure 27:
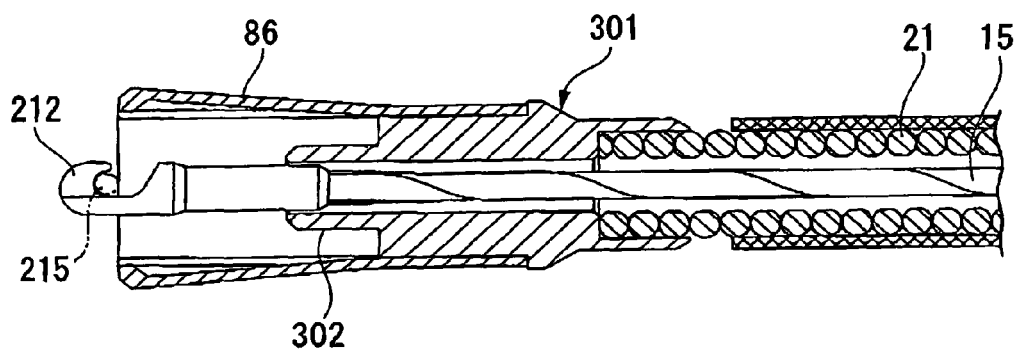
FIG. 27 is a sectional view showing a distal claw portion formed integrally.

As shown in FIG. 27, a distal claw portion 301 is fixed to the distal end of the hook sheath 21, and the hook operating wire 18 is drawn therein. Further, the distal claw portion 301 is fixed to the casing holding portion (whose end is slightly opened outwardly in the radial direction so as to receive the casing 150) 86. A claw portion 302 is formed integrally with the tip of the distal claw portion 301, by which the proximal end of the casing 150 can be locked. The distal claw portion 301 is formed by molding the distal claw portion 211 and the step 86A of the casing supporting member 86 that receives the distal claw portion 211 integrally with each other as shown in FIG. 9, and hence both manufacturing costs and the number of assembling steps can be reduced.

Figure 28:
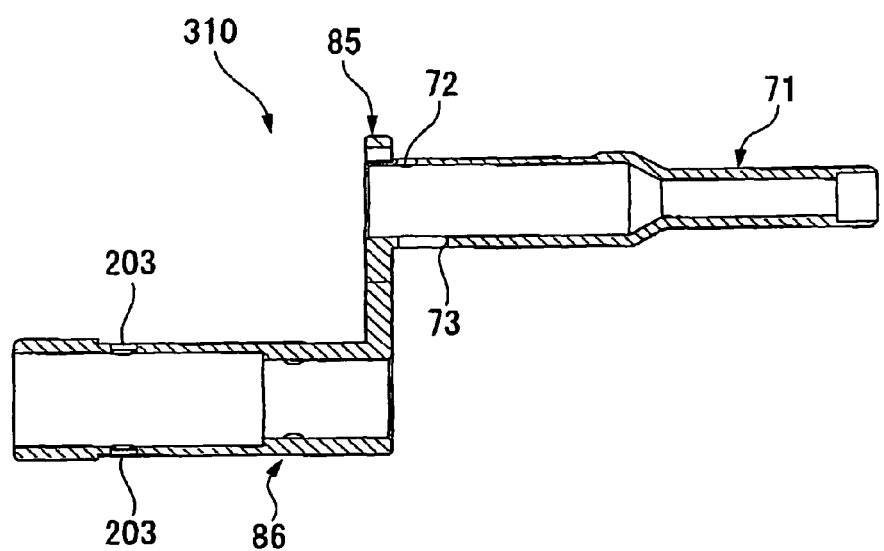
FIG. 28 is a view showing a structure in which a distal-end supporting portion, a bridge portion, and a casing holding portion are formed integrally with each other.

As shown in FIG. 28, it is permissible to use a supporting member 310 formed by integrally molding the distal-end supporting portion 71, the bridge portion 85, and the casing supporting member 86. The supporting member 310 is bent like a crank as a whole, and can make component costs and assembly costs lower than a structure in which the distal-end supporting portion 71 and the casing supporting member 86 are formed individually. Metal injection molding, turning center, molding, casting, or forging can be used as the producing method.

Figure 29:
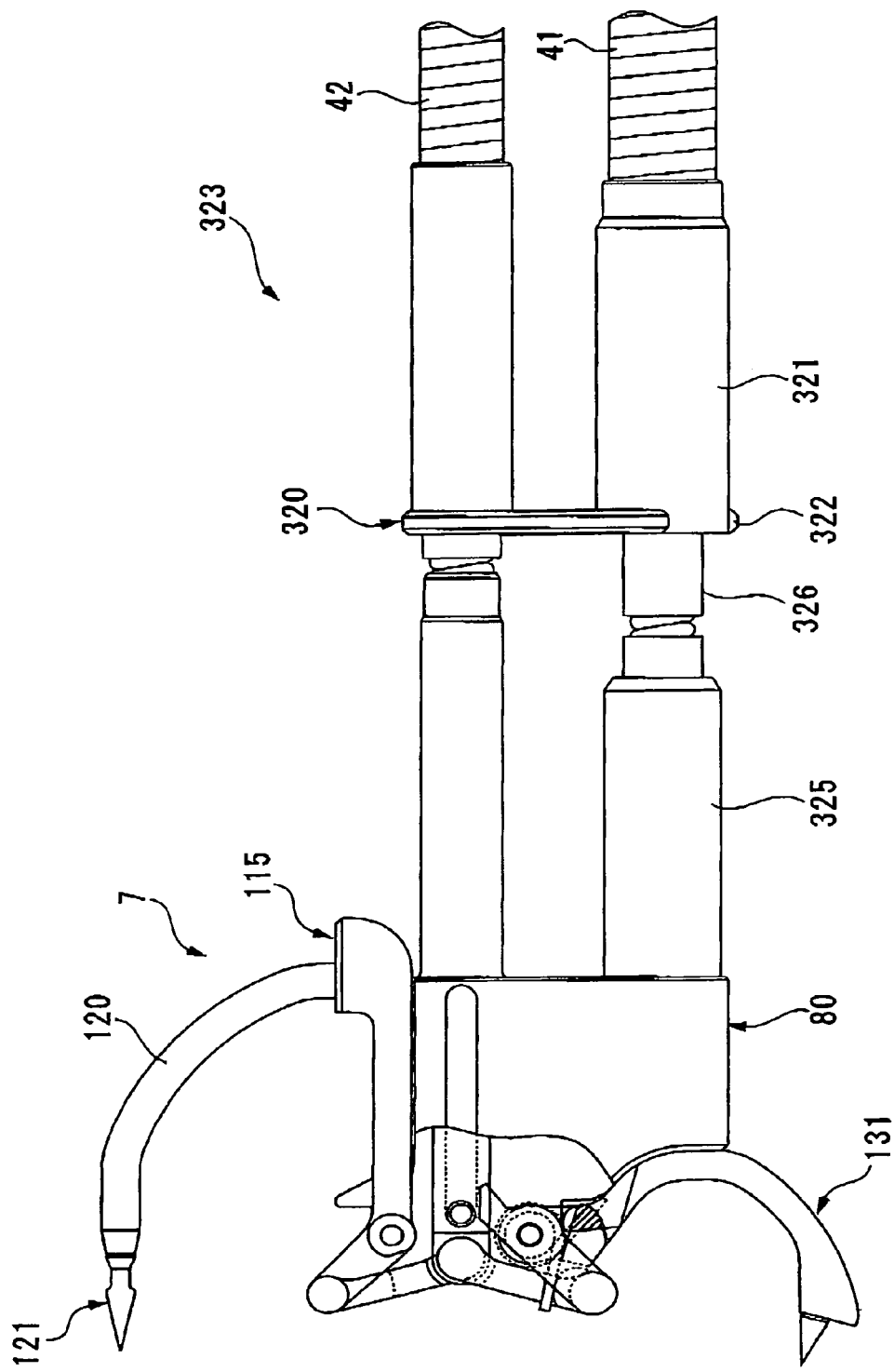
FIG. 29 is a view showing a distal end of a suture instrument according to another embodiment, in which a receiving portion is provided with a cut.

As shown in FIG. 29, in a receiving portion 320, a cut 322 may be formed in a part that is engaged with an outer member 321 to which the tip of the coil sheath 41 is fixed. The receiving portion 320 is used to fix the distal end of the endoscope 4 to a suture instrument 323. The receiving portion 320 holds the outer member 321 substantially in the cross-sectional shape of the letter C by means of the cut 322. The position of the cut 322 is a position at which the endoscope 4 and the suture instrument 323 are brought into contact with or close to the inner surface of the overtube 6 when the endoscope 4 and the suture instrument 323 are combined together and are inserted into the overtube 6. The outer diameter obtained by combining the endoscope 4 and the suture instrument 323 together can be reduced by cutting the receiving portion 320 at this position, and the insertion into the overtube 6 can be easily carried out. The suture instrument 323 has a structure in which the distal claw portion 301 that is engaged with the casing 150 is moved back and forth by a sheath 326. The distal claw portion 301 is moved back and forth inside the tip cover 80 and a casing holding portion 325 formed integrally with the tip cover 80.

Figure 30:
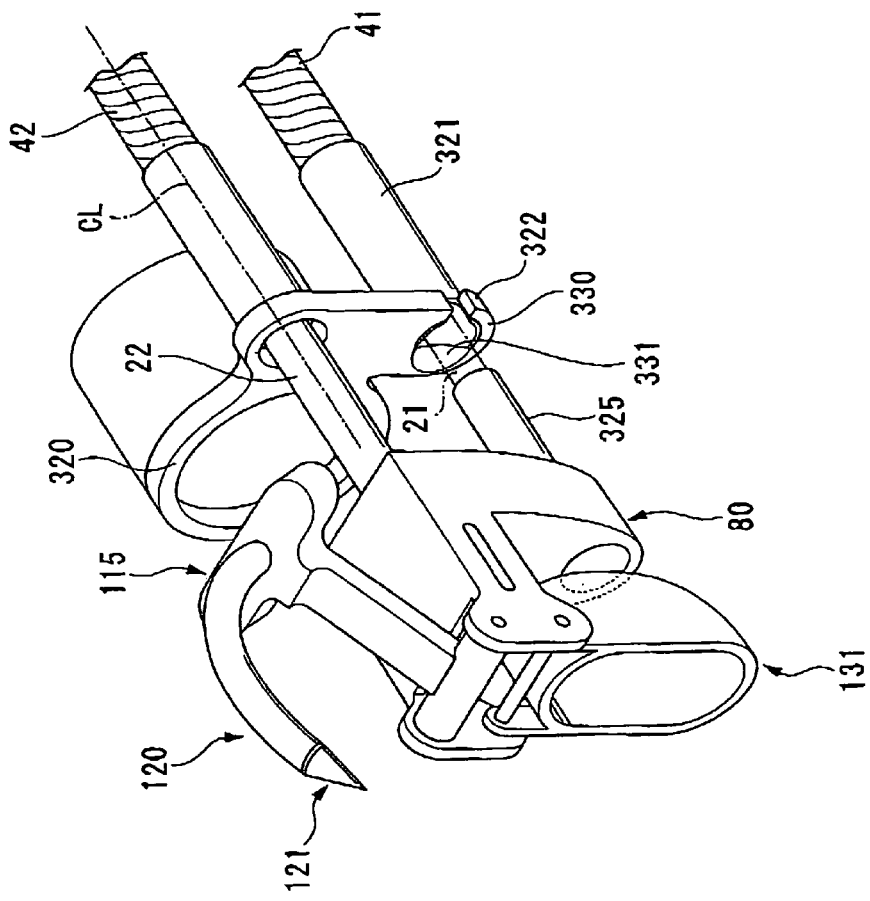
FIG. 30 is a view showing a receiving portion provided with a cut and a tapered surface.

As shown in FIG. 30, in the receiving portion 320, a holding portion 330 holding the outer member 321 has the cut 322 so that the cross section thereof has the shape of the letter C, and a tapered surface 331 that is opened toward the distal end is provided. The tapered surface 331 has a curved surface in which the axis line CL of the coil sheath 42 is a center axis. When the tip cover 80 is allowed to recede by operating the hook sheath 21 and the forceps sheath 22, the proximal end of the casing holding portion 325 is not caught by the receiving portion 320, and hence the tip cover 80 can be smoothly moved back and forth.

Figure 31:
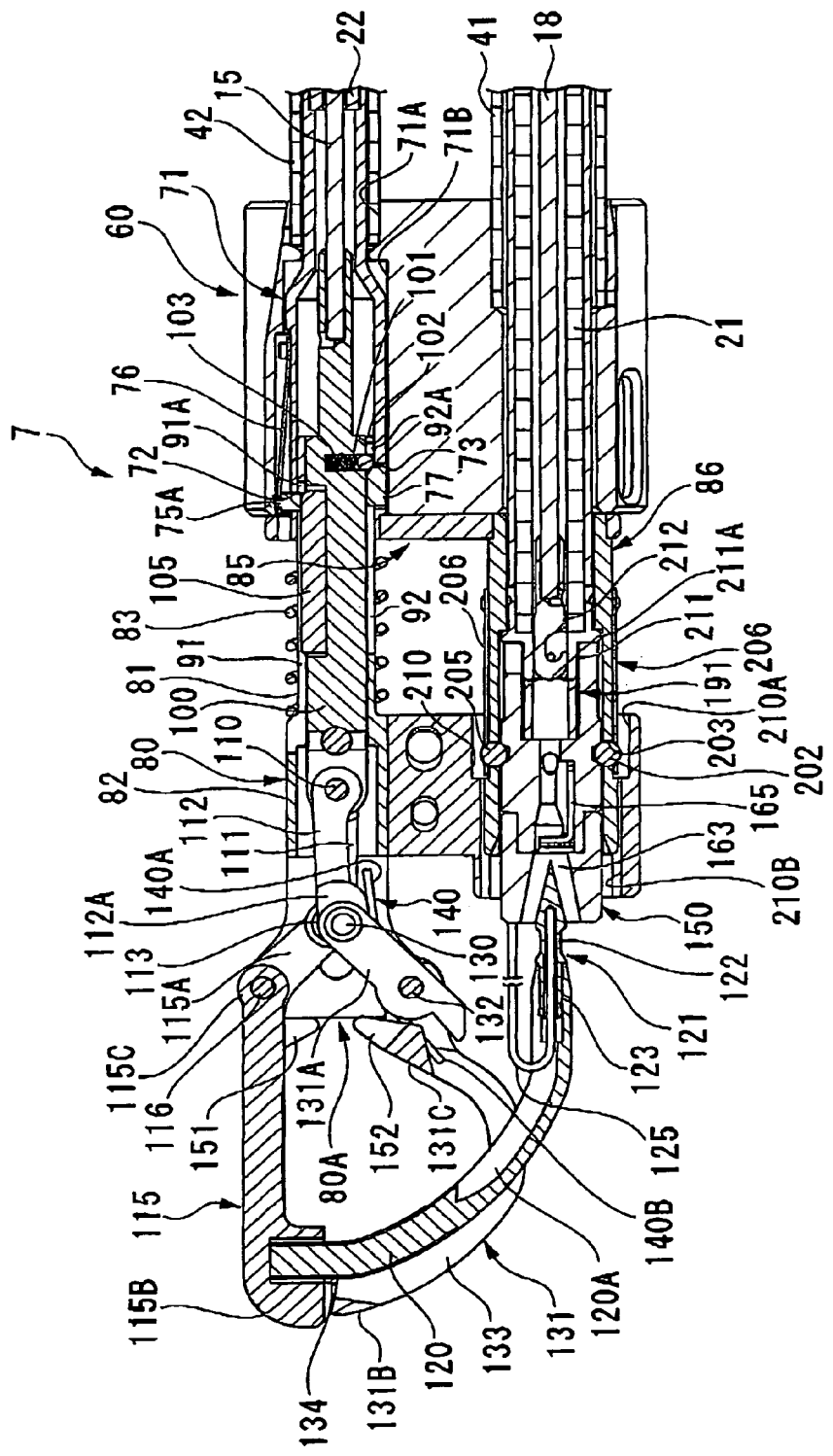
FIG. 31 shows a modified example of a first locking member.

The round shape pin 75 shown in FIG. 9 as the first locking member may be replaced by an approximate columnar pin 75A as shown in FIG. 31. Using the columnar pin 75A increases the length of engagement with the hole 72, thereby prevents the first locking member from removing therefrom during the operation. The first locking member does not remove from tissues subject to puncture since the force necessary to release the engagement of first locking member becomes stable.

Second Embodiment

Figure 32:
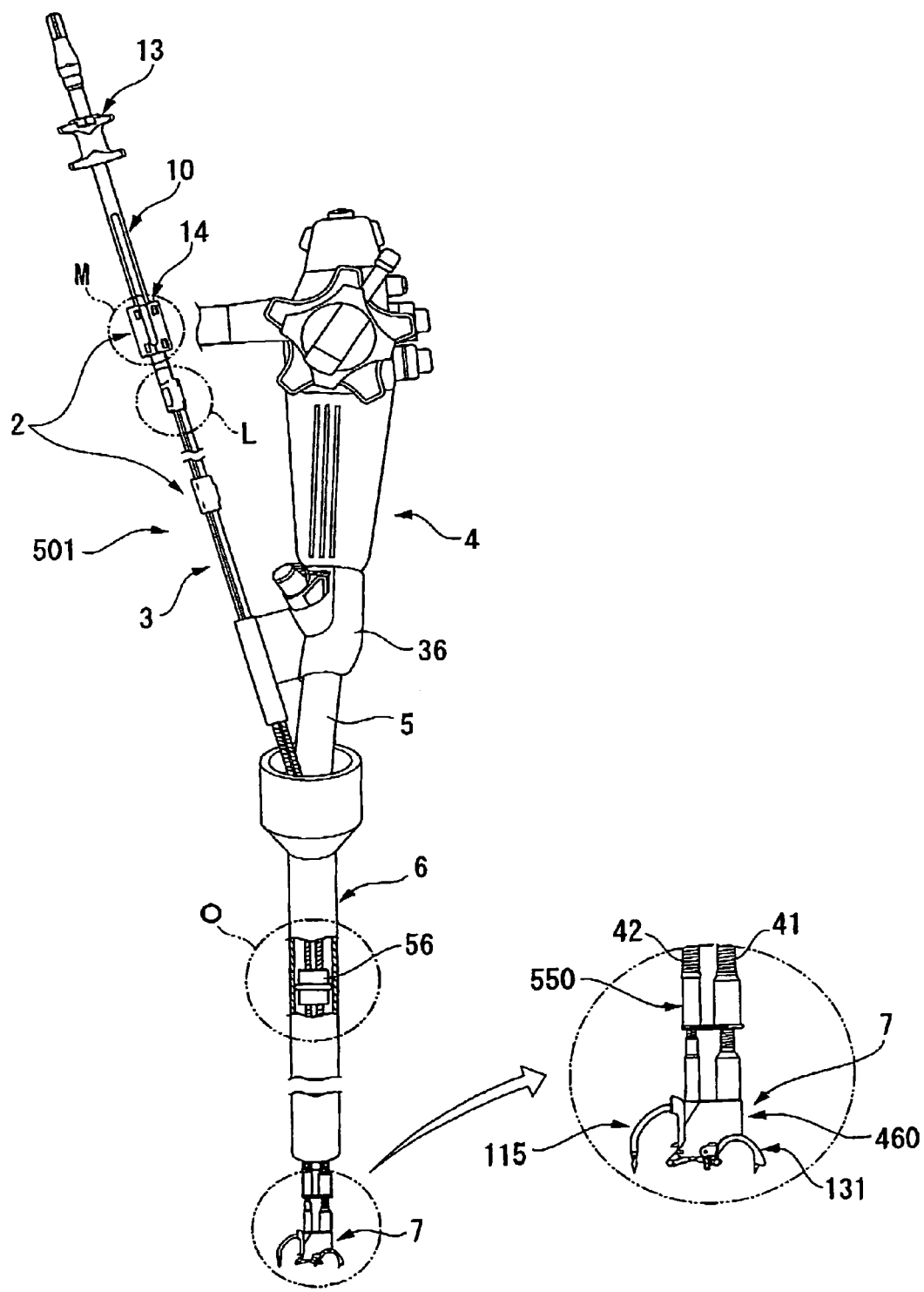
FIG. 32 is a view showing a schematic structure of a suture instrument which is an embodiment of an endoscope and an endoscopic treatment instrument.

FIG. 32 illustrates a suture instrument according to a second embodiment inserted together with the endoscope through the overtube.

A suture instrument (applicator) 501 as an endoscopic treatment instrument has a long insertion portion 3 extended from a control portion 2 that is operated by an operator. The control portion 2 is attached to an elongated control body 10 so that a forceps operating portion 13 and a hook operating portion 14 are independently slidable.

Figure 33:
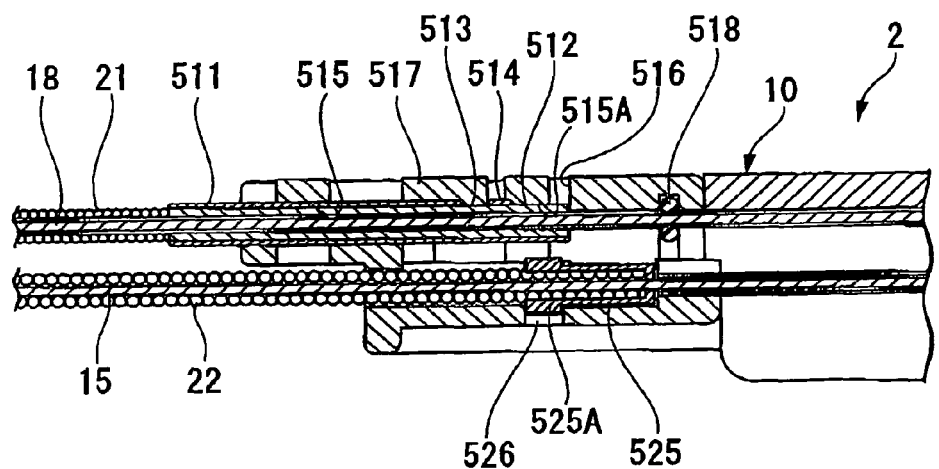
FIG. 33 is a cross section showing an area L shown in FIG. 32.

As shown in FIG. 33 showing the enlarged cross sectional view of the area L of FIG. 2 in FIG. 33, inserted through the distal end of the control body 10 are a hook operating wire 18, a hook sheath 21, a forceps operating wire 15, and a forceps sheath 22.

A sheath fixing pipe 511 is brazed to the hook sheath 21. An offset part of the end portion of the sheath fixing pipe 511 along its axial line from its axial line is cut so as to form a C-shaped cross section. Two regions are cut to form cuts 512, 513 along the axial line direction. The remaining part 514 between the cuts 512, 513 inclines so that a wall surface closer to the proximal end opens toward the distal end. A wall surface of the part 514 closer to the distal end is approximately orthogonal to the axial line. The wall surface closer to the distal end of the cut 513 inclines toward the outer periphery in the radial direction and toward the distal end so as to prevent the inserted sheath fixing pipe 511 from being caught. Formed on the tip part section of the control body 10 is a hole 515 through which the sheath fixing pipe 511 can be inserted. The hole 515 has a wall section 516 to which an end section of the sheath fixing pipe 511 is abutted, and a section extending from the wall section 516 forms a hole 515A having an approximate C-shape cross section. The hole 515A has an outline approximately the same as the cross sectional shape of the cut section of the sheath fixing pipe 511. An elastically deformable hook 517 is formed by means of the circumferential wall of the hole 515 so as to extend from the hole 515A. The sheath fixing pipe 511 cannot be removed since the hook 517 projects so as to be able to engage with the cut 513.

Inserting the sheath fixing pipe 511 through the control body 10 until abutting its end section to the wall section 516 contains the cut 512 in the hole 515A having an approximate C-shape, thereby regulating the rotation around the axial line. Simultaneously, the hook 517 is inserted into the cut 513. The hook 517 caught by the withdrawn wall section of the part 514 of the sheath fixing pipe 511 prevents the hook sheath 21 from being removed. In addition, the sheath fixing pipe 511 extending from the tip of the control body 10 by a predetermined length has a function for preventing the hook sheath 21 from being broken.

The hook operating wire 18 retractably inserted through the hook sheath 21 is withdrawn across the wall section 516 and inserted into the hook operating portion 14 after passing through a hook ring 518.

Figure 34:
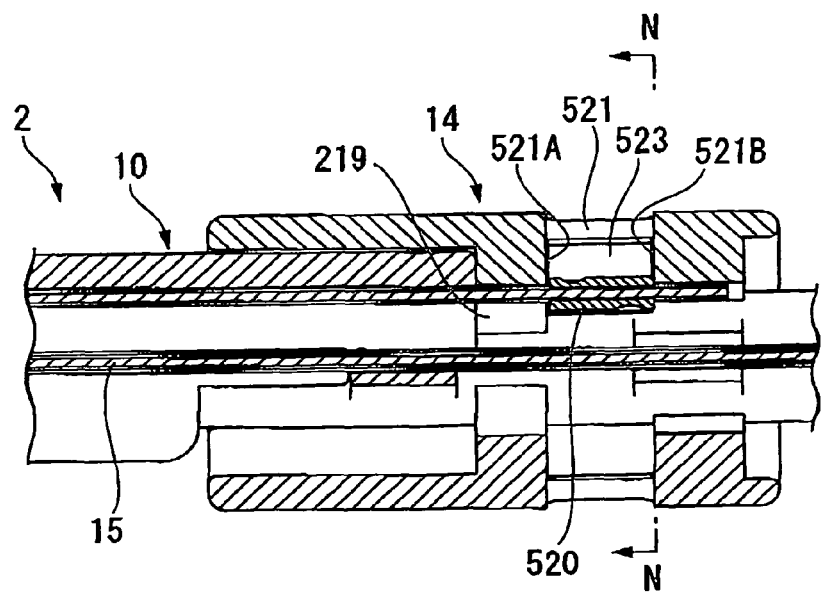
FIG. 34 is a cross section showing an area M shown in FIG. 32.
Figure 35:
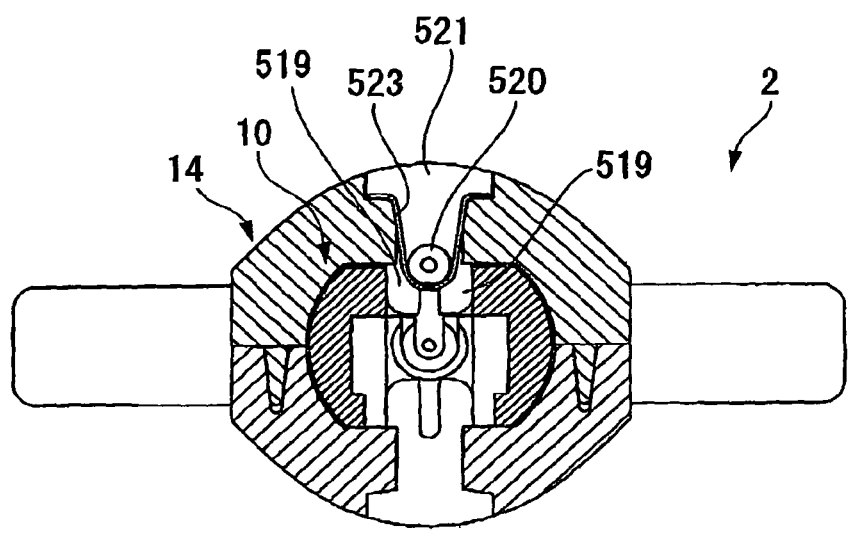
FIG. 35 is a cross-sectional view taken along the line N-N of FIG. 34.

As shown in FIGS. 34 and 35, the hook operating portion 14 has a pair of claws 519 extending across a path through which the hook operating wire 18 passes, and the hook operating wire 18 is inserted through a space between the claws in the hook operating portion 14. Crimped to be fixed to the tip section of the hook operating wire 18 is a wire-fixing pipe 520. Engaging the wire-fixing pipe 520 to the hook operating portion 14 provides a locking effect. The wire-fixing pipe 520 is disposed in a slit 521 formed between the outer periphery and an inner section of the hook operating portion 14. The slit 521 has approximately the same length as that of the wire-fixing pipe 520, and longitudinal wall sections 521A and 521B regulate the back-and-forth movement of the wire-fixing pipe 520.

Inserted furthermore into the slit 521 is an engagement band 523. The approximately U-shape engagement band 523 has one open end. The bending part of the engagement band 523 makes surface contact with the outer circumference of the wire-fixing pipe 520 and the inner faces of the hook operating portion 14 while extending from here toward the outer periphery of the hook operating portion 14. Its end parts are fixed to the hook operating portion 14 in a region radially outside the passing-through wire-fixing pipe 520. This prevents the wire-fixing pipe 520 from radially moving inward therefrom.

Engaging the hook operating wire 18 at the end of the slit on the claw 519 regulates the radially outwardly movement of the wire-fixing pipe 520. The way the hook operating wire 18 is fixed to the hook operating portion 14 increases extrusion resistance of the hook operating wire 18, thereby preventing the hook operating wire 18 from, even if deformed, being removed from the hook operating portion 14.

As shown in FIG. 33, a brass sheath fixing pipe 525 is crimped and fixed at an end of the forceps sheath 22. The outer periphery of the tip of the sheath fixing pipe 525 is enlarged to form a locking section 525A. Inserting the locking section 525A into a groove 526 formed on the control body 10 allows the forceps sheath 22 to be locked with the control body 10. The sheath fixing pipe 525 crimps a part of the forceps sheath 22 closer to the proximal end inserted from the locking section 525A the proximal end. The locking section 525A formed closer to the distal end facilitates insertion of a crimping tool. Also, the brass-made sheath fixing pipe 525 can be machined easier than a stainless-steel made component. Therefore, the cost can be reduced.

Figure 36:
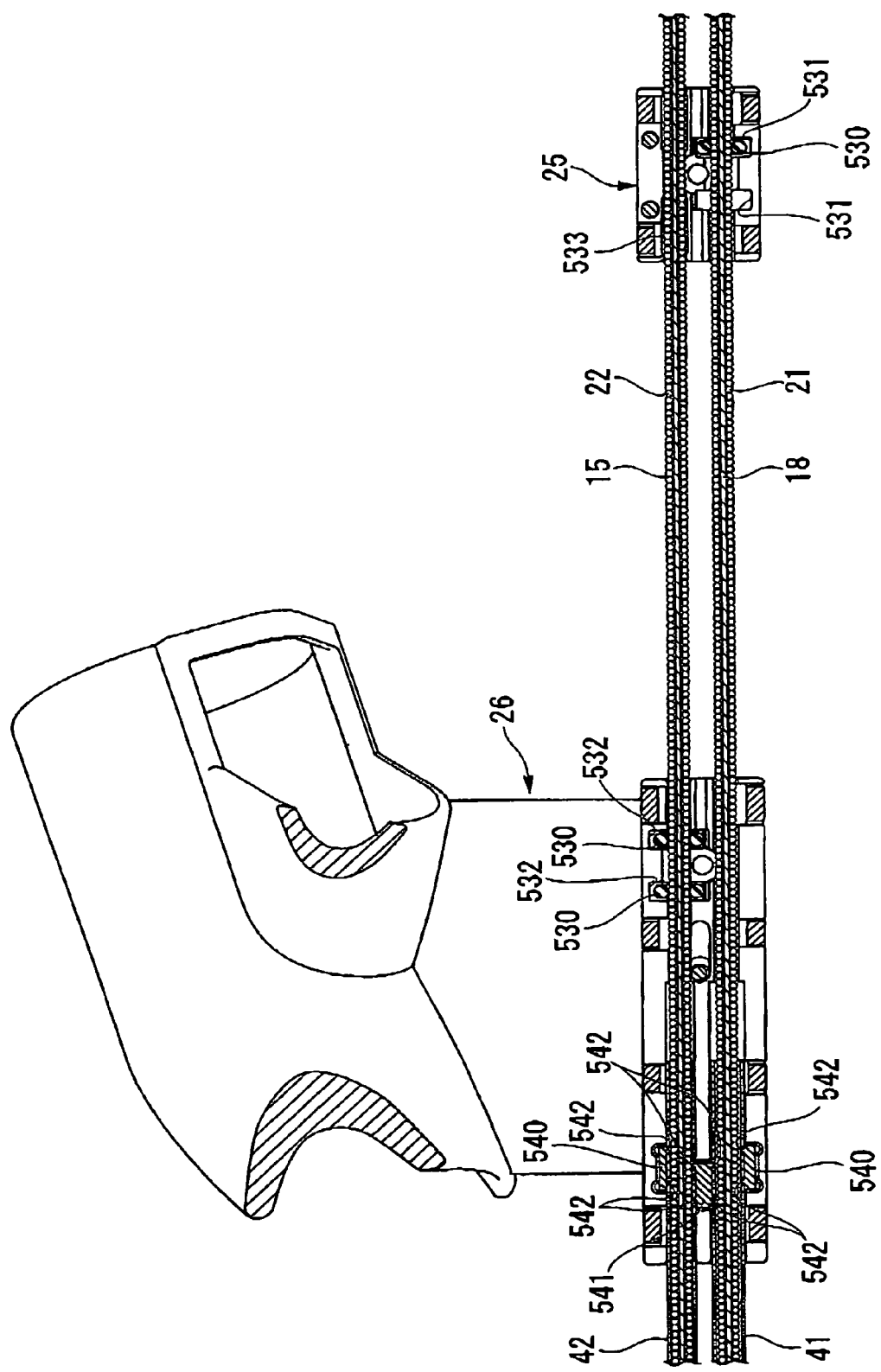
FIG. 36 is a partial cross sectional view showing a structure of an insertion portion.

As shown in FIG. 36, the hook sheath 21 and the forceps sheath 22 are passed in this order through a movement control portion 25 and a scope holder 26. The forceps sheath 22 is fixed to the movement control portion 25. The hook sheath 21 increases its sliding resistance at an O-ring 530 accommodated in the movement control portion 25. The O-ring 530 is accommodated in one of two receiving sections 531 formed in the longitudinal direction for containing the O-ring 530. The two receiving sections 531 each may accommodate the O-ring 530.

Also, sliding resistance of the forceps sheath 22 passing through the scope holder 26 increases at an O-ring 530 in the receiving section 532. Two receiving section 532 are formed in the longitudinal direction for containing the O-ring 530. The O-ring 530 may be accommodated in one of the receiving sections 532. A pipe 533 is crimped and fixed to a portion of the forceps sheath 22 subject to be accommodated in the movement control portion 25. The pipe 533 engages a groove of the movement control portion 25.

The sliding resistance caused by the forceps sheath 22 is greater than that caused by the hook sheath 21 when the hook sheath 21 exposed between the movement control portion 25 and the scope holder 26 are held and moved back and forth since the hook sheath 21 has one braking O-ring 530 while the forceps sheath 22 has two braking O-rings 530. This allows only the movement of the hook sheath 21 while the forceps sheath 22 does not move.

In order to move the two sheaths 21 and 22, the movement control portion 25 is held and moved back and forth. The engagement between the forceps sheath 22 and the movement control portion 25 by means of the pipe 533 provides greater back and forth moving force that overwhelms the braking force caused by the two O-rings 530 accommodated in the scope holder 26. The hook sheath 21 moves together with the movement control portion 25 by means of the sliding resistance caused by the O-ring 530 accommodated in the movement control portion 25.

Using the O-ring 530 for adjusting the sliding resistance in the movement control portion 25 realizes a brake appropriate for moving the sheaths 21 and 22 back and forth. If the sliding resistance of O-rings in use with the sheaths 21 and 22 is insignificant, three or more O-rings may be used. Braking capability and O-ring durability can be improved. Also, an O-ring may be replaced by a tube made of resin, e.g., silicone.

In addition, enlarging the diameter or the elemental wire of the forceps sheath 22 provides greater hardness of the coil in order to prevent the bending of the forceps sheath 22 and extending of the hook sheath 21 when the movement control portion 25 is extended. Desirable hardness of the forceps sheath 22 in this case does not bend the forceps sheath 22 when the suture instrument 501 compresses the tissues.

The diameter of the elemental wire of the hook sheath 21 is also enlarged in order to prevent the hook sheath 21 from yielding when the hook sheath 21 is compressed by holding the scope holder 26. This allows the hook sheath 21 to be compressed smoothly. Decreasing the clearance between the hook sheath 21 and the hook operating wire 18 provides a sliding movement of the hook operating wire 18 with the hook sheath 21. Larger clearance between the hook sheath 21 and the hook operating wire 18 may bend the hook operating wire 18 to serpentinly wind in the hook sheath 21. The operational stroke of the hook operating portion 14 in this case must be increased in accordance with the serpentine hook operating wire 18. In contrast, the suture instrument 50 having a reduced clearance and a less significant stroke provides improved operability to the hook operating wire 18.

Figure 37:
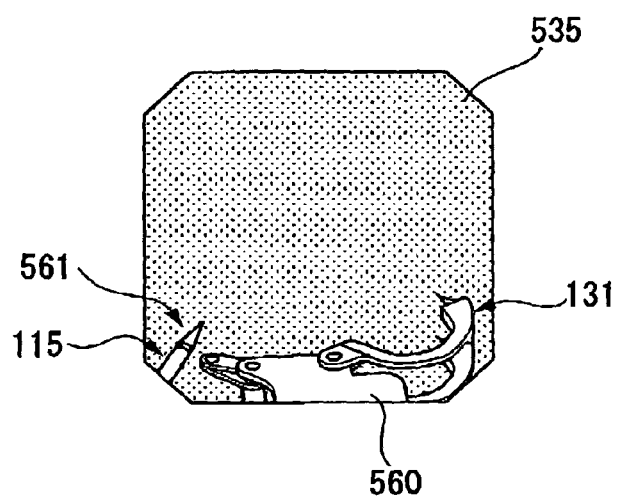
FIG. 37 is a schematic diagram of an endoscopic image.

The forceps sheath 22 and the hook sheath 21 are inserted through the scope holder 26 in a predetermined order. The hook sheath 21 is disposed on the right-hand side of the operator and the forceps sheath 22 is disposed on the left-hand side of the operator who holds the endoscope 4 in the left hand and operates the hook sheath 21 and the forceps sheath 22 by the right hand. This results in the disposition in a image 535 of the endoscope 4 shown in FIG. 37 where the hook is on the right-hand side and a curved needle 120 is on the left-hand side. The displayed erect image permits easy operation to the operator who observes it.

As shown in FIG. 36, the hook sheath 21 and the forceps sheath 22 are inserted through the coil sheath 41 and the coil sheath 42 respectively in the scope holder 26. Each of the coil sheaths 41 and 42 is made out of a flat and closely-wound coil obtained by closely winding a flat plate. Locking members 340 and 341 are fit in the scope holder 26 for preventing the coil sheaths 41 and 42 from removing therefrom. The locking members 540 and 541 are press-fit in recesses provided closer to the scope holder 26, and two separate protrusions 542 are provided in the longitudinal directions of the coil sheaths 41 and 42. The protrusions 542 are formed alternately with respect to the longitudinal direction of the two locking members 540 and 541 placing the coil sheath 41 in between. Similarly, the protrusions 542 are formed alternately with respect to the longitudinal direction of the two locking members 540 and 541 placing the coil sheath 42 in between. The protrusions 542 entering between the wires of the coil prevents the coil sheath 41, 42 from removing there. The coil sheaths 41 and 42 are fixed by adjusting the projection of the coil sheaths 41 and 42 from the scope holder 26 having the press fit locking members 540 and 541 in a state where the hook sheath 21 and the forceps sheath 22 are passed through continuous grooves of the scope holder 26. Pressing the positioned coil sheaths 41 and 42 engages them to the protrusions 542. This shortens the assembly time and facilitates the adjusting of the lengths of coil sheaths 41 and 42.

The outer periphery of the hook sheath 21 is uncoated, and the hook sheath 21 and the coil sheath 41 constitute a reduplicate structure. These uncoated stainless-steel-made sheaths 21 and 41 provide desirable sliding between the sheaths 21 and 41. The hook sheath 21 can be extended and retracted easily when the endoscope 4 is angularly bent.

Figure 38:
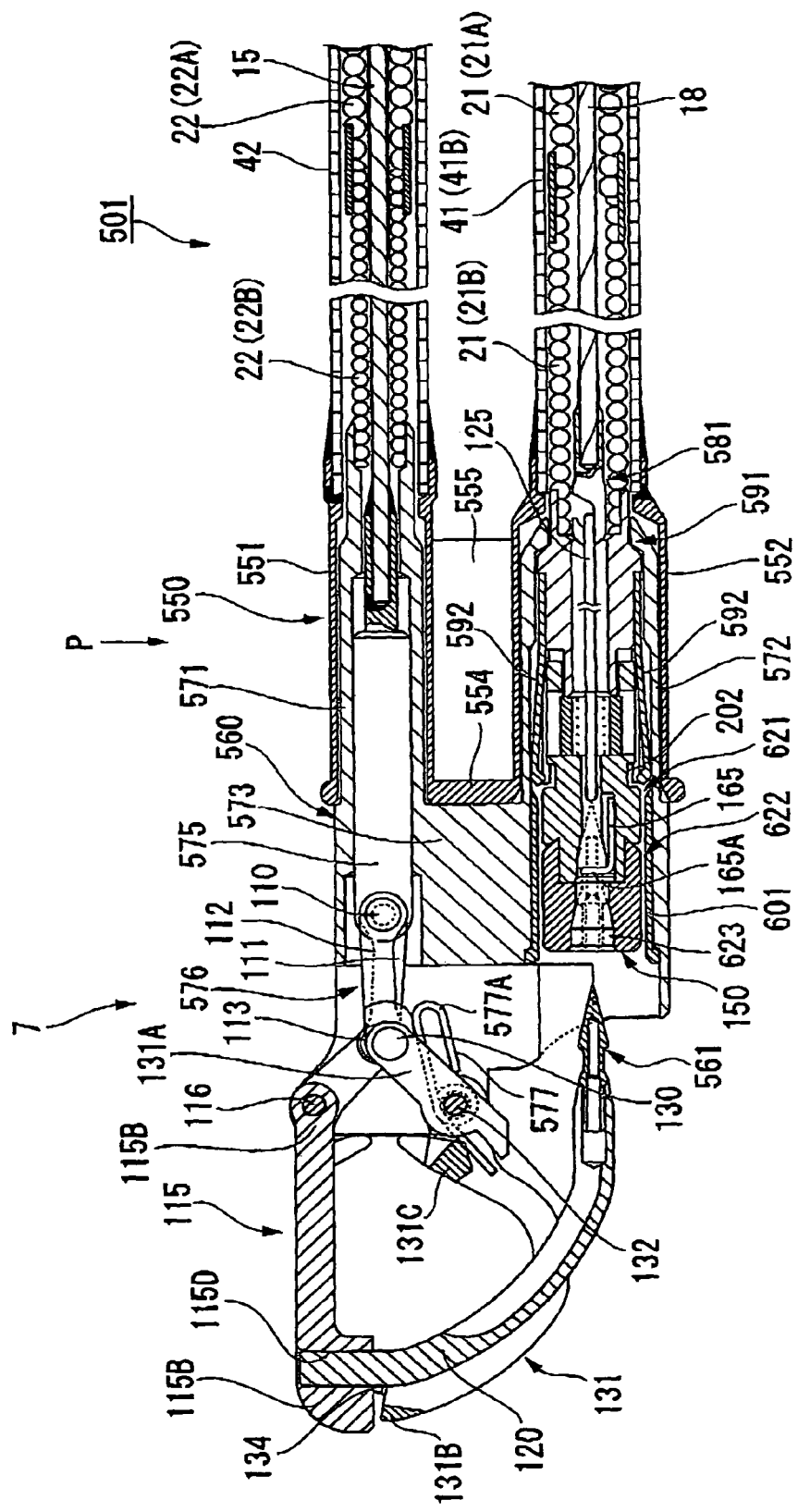
FIG. 38 is a cross sectional view of a tip portion of a suture instrument.

The elemental wire of the manipulation side coil 21A is differentiated from the elemental wire of the distal end coil 21B in the hook sheath 21 as shown in FIG. 38. The enlarged diameter of the elemental wire of the manipulation side coil 21A prevents the coil from extending when the hook sheath 21 is pulled. Also, the reduced diameter of the elemental wire of the distal end coil 21B provides flexibility, thereby facilitating the angular bending of the endoscope 4. The angularly bent hook sheath 21 can be further slid with moderate force. As shown in FIG. 38, a flat coil 41A constitutes a manipulation side of the coil sheath 41, and a flat thick coil 41B constitutes a distal end thereof. The coil sheath 41 which is almost not extendable with the extended forceps sheath 22 improves the operability of the forceps sheath 22, thereby facilitating the bending of the endoscope 4 at the distal end. The thick flat coil 41A reaching the distal end used in place of the flat coil 41B can prevent the extension of the coil sheath. The boundaries of coils 21A, 21B, 41A, and 41B are welded.

The outer periphery of the hook sheath 22 is uncoated, and the hook sheath 22 and the coil sheath 42 constitute a reduplicate structure. These stainless-steel-made sheaths 22 and 42 provide desirable slidability between the sheaths 22 and 42. The enlarged diameter of the elemental wire of the manipulation side coil 22A of the forceps sheath 22 prevents the extension of the coil when the forceps sheath 22 is pulled. Also, the reduced diameter of the elemental wire of the distal end coil 22B facilitates the angular bending of the endoscope 4. The angularly bent hook sheath 22 can be further slid with moderate force.

A less significant clearance between the coil sheath 41 and the hook sheath 21 prevents an air insufflated into a body from leaking out of the body through the sheaths 21 and 41. The clearance between the coil sheath 42 and the forceps sheath 22 is less significant. Increased air tightness which prevents air leakage, e.g., during the insufflation of a stomach, facilitates the insufflation shortly, and a previously insufflated stomach will not contract instantly. Reduced number and time of insufflation provides easy operations, thereby moderating stress exerted on the operator.

As shown in FIGS. 32, 38, 40 and 41, the distal ends of the coil sheaths 41 and 42 are welded to a scope holder 550. Disposed in the scope holder 550 are two tube parts 551 and 552 respectively having the coil sheaths 41 and 42 connected thereto; a tube part 552 for receiving the endoscope 4 so that the tube parts are united at a distal end connection section 554 approximately in parallel. The three tube parts 551 to 553 in one unit increases the parallelism between the two tube parts 551 and 552, thereby facilitating the projection and recession of the treatment section 7.

Figure 40:
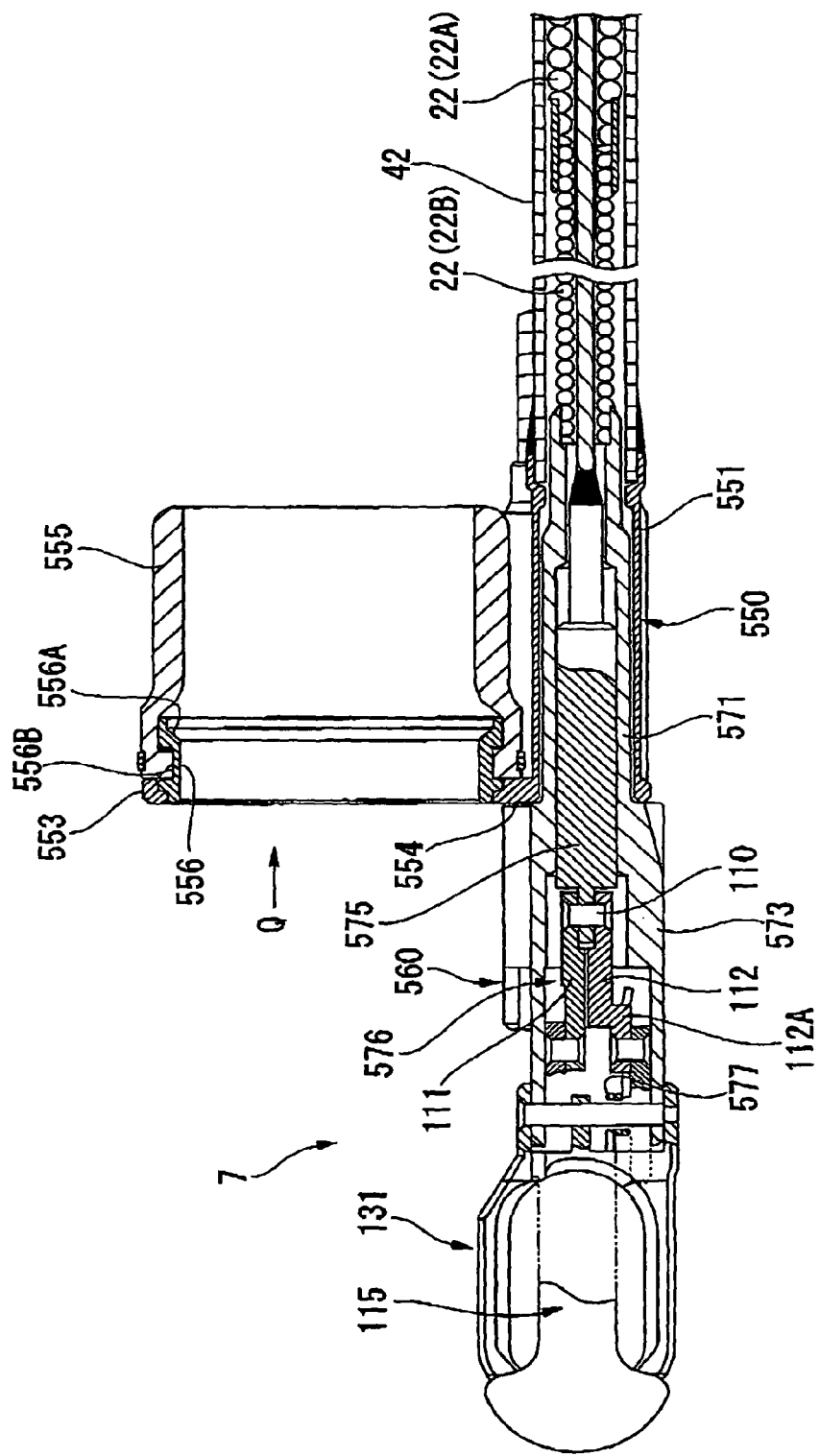
FIG. 40 is a view on arrow P in FIG. 38.

As shown in FIG. 40, a resin-made hood 555 is attached to an inner ring 556 that is welded to the tube part 553 in one unit. This accordingly facilitates the machining of each component. The inner diameter of the inner ring 556 is approximately the same as the inner diameter of the hood 555, and a end surface 556A is chamfered, i.e., the inner diameter increases radially. The outer diameter of the inner ring 556 having an annular groove 556B is greater than the inner diameter of the hood 555. The hood 555 in use having capability of supporting the endoscope 4 is not spontaneously removed from the inner ring 556. Easy attachment of the hood 555 during assembly reduces man-hours in the assembly. Attaching the hood 555 includes fitting the inner ring 556 and fitting the tip part section of the hood 555 to a groove 354B. The surface of the distal end of the inner ring 556 and the tube part 553 are unified by means of, e.g., a laser welding method. Since the depth of the groove 556B of the inner ring 556 and the fitting height of the hood 555 are substantially obtained, the attaching strength of the hood 555 is improved.

Figure 41:
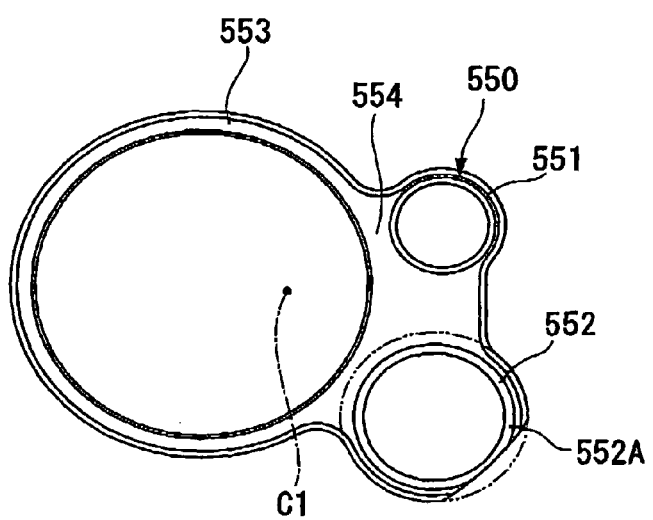
FIG. 41 is a view on arrow Q in FIG. 40.

As shown in FIG. 41, an opening 552A at the distal end of the tube part 552 is cut in an arch around a rotational axis C1 of the scope holder 550, i.e., in an approximate D-shape. The scope holder 550 having a small outer diameter can be inserted through the overtube 6. Withdrawing is facilitated even if the treatment section 7 is inclined.

As shown in FIGS. 38 and 40, the treatment section 7 has a tip cover 560 supported by the scope holder 550, and a pair of forceps members 115 and 131 that freely open and close are supported by the tip cover 560. Accommodated further in the tip cover 560 is a freely extending and retracting casing 150 for receiving a detachable needle 561 attached to the forceps member 115. The length of the tip cover 560 is adjusted so that a tip of a detachable needle 561 is captured in a display of the endoscope 4 since the forceps members 115 and 131 are opened until the detachable needle 561 is received. This provides the opening pair of forceps members 115 and 131, and the detachable needle 561 in a lower portion of the displayed image 535 of the endoscope 4 as shown in, for example, FIG. 37. This disposition permits the operator to observe the trace of the detachable needle 561 in the image 535 until the pair of forceps members 115 and 131 close. The operator can conduct treatment while continuously observing the detachable needle 561. Thus, the reliability of the treatment can be improved.

Figure 42:
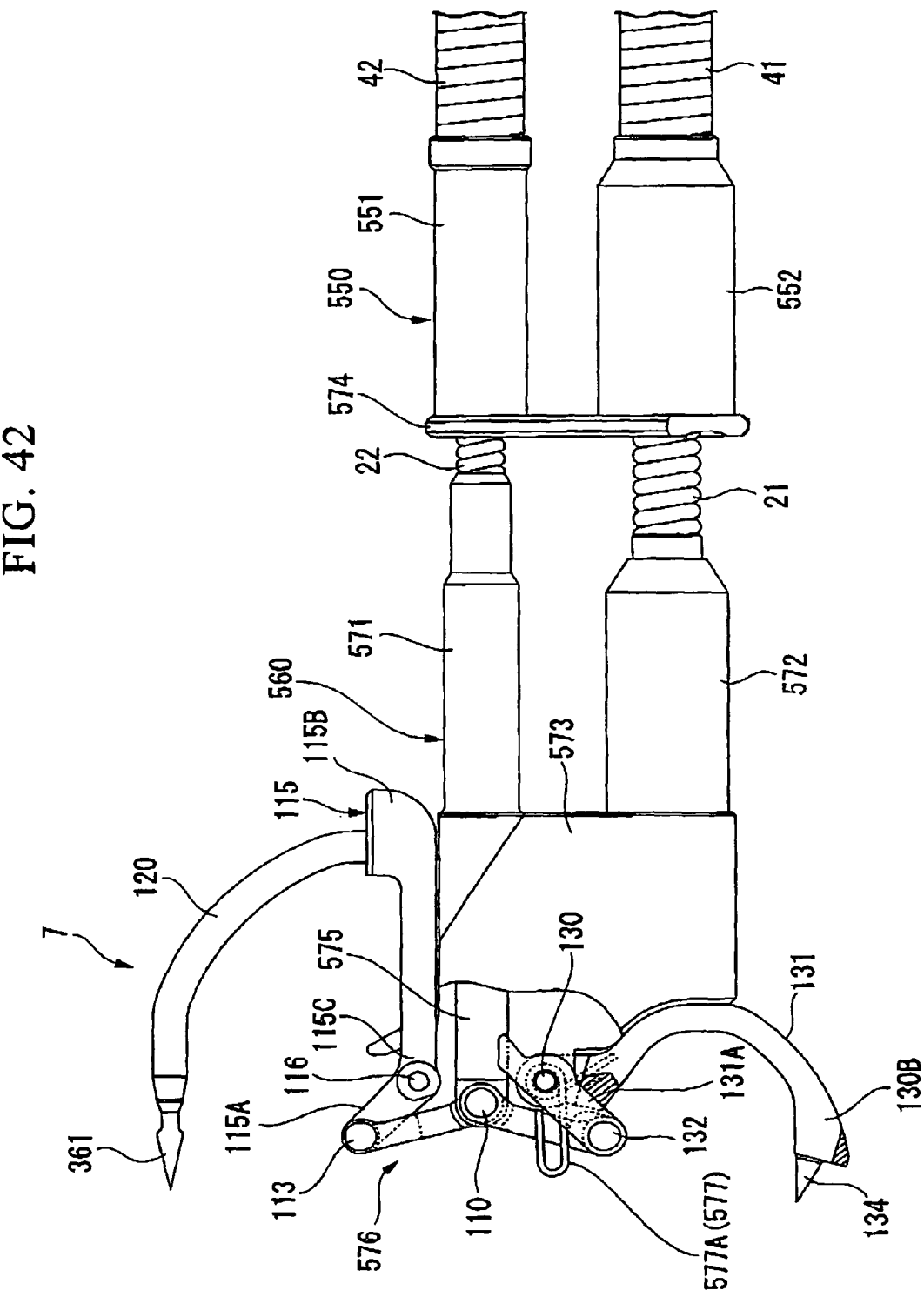
FIG. 42 illustrates an open state of a pair of forceps members.

As shown in FIGS. 38, 40, and 42, the tip cover 560 is configured so that a forceps-receiving section 571 having the forceps sheath 22 connected thereto by means of, e.g., laser welding method and a cartridge supporting member 572 having the hook sheath 21 connected thereto by means of, e.g., laser welding method are connected in one unit by a connection 573. Provided in the forceps-receiving section 571 is a link mechanism 576 configured to include a rod 575 connected to the forceps operating wire 15. Connected to the distal end of the rod 575 are a pair of link members 111 and 112 by means of a pin 110. The link member 111 is connected to a first forceps member by means of a pin 113. The first forceps member 115 extends from one pin-connected end section to the other end section having a curved needle 120 connected thereto and rotatively supported by the tip cover 560 via a pin 116. Attached on the distal end of the curved needle 120 is a detachable needle 561.

The opposite end of the other link member 112 is rotatably connected to the proximal end of an intermediate member 131A by means of a pin 130. The distal end of the intermediate member 131A is rotatably supported by the tip cover 560 via a pin 132.

In the forceps member 131, a part 131C supported by the tip cover 560 via the pin 132 is disposed inside the tip cover 560. The forceps member 131 is urged by a charging spring 577 so that the tip part 131B of the forceps member 131 is fully closed when the forceps members 115 and 131 are closed. The coiled charging spring 577 is slidably wound around the pin 132. An end 577A of the charging spring 577 makes contact with the opposite end 112A (see FIG. 40) of the link member 112 when the pair of forceps members 115 and 131 are closed. An opposite end of the charging spring 577 comes into contact with the part 131C of the forceps member 131. Since the charging spring 577 slidably and rotatively wound around the pin 132 does not incline relative to the pin 132, it will not be removed from the link member 112 and the forceps member 131.

As shown in FIG. 42, the end 577A of the charging spring 577 projects from the tip cover 560 toward the tissue when the forceps members 115 and 131 are opened. Since the approximately U-shaped bending portion of the end 577A is disposed toward the distal end, it will not stick the tissue when the distal end is pressed thereto.

Since the link members 111 and 112 each are longer than the distance between the rod 575 and the pins 116 and 132 as shown in FIG. 41, the rod 575 cannot move further toward the distal end from this position. Therefore, the pin provided onto the rod and the guide hole provided on the tip cover in accordance with the first embodiment will not be necessary. A guide hole may be provided onto only one end of the tip cover 560 for use in positioning the attaching device described in another embodiment.

The curved needle 120 is inserted through a hole 115D having a circular cross section formed in the first forceps member 115 to be welded and fixed there. The cross sectional shape of the curved needle 120 is also an approximate circle, and both components are positioned by means of a jig that is not shown in the drawings. Machining man-hour can be reduced compared with a conventional case where the positioning is conducted by cutting the cross section of the curved needle 120 in a C-letter shape.

A hook 581 is fixed to the distal end of the hook operating wire 18. The hook 581 in a withdrawn state is put in the hook sheath 21. Greater sliding resistance between the hook 581 and the hook sheath 21 disturbs the movement of the hook 581. Furthermore, if the sliding resistance is greater, the greater sliding resistance damps the movement of the hook 581 when the endoscope 4 is bent. The clearance between the hook 581 and the hook sheath 21 is therefore increased so that the extending and retracting movement of the hook 581 can be provided by a moderate force. Incidentally, it is desirable that the clearance is greater than 0 mm and no greater than 0.1 mm. This range provides desirable movement of the hook 581. Therefore, the suture thread 125 will not be unhooked from the hook 581.

Figure 43:
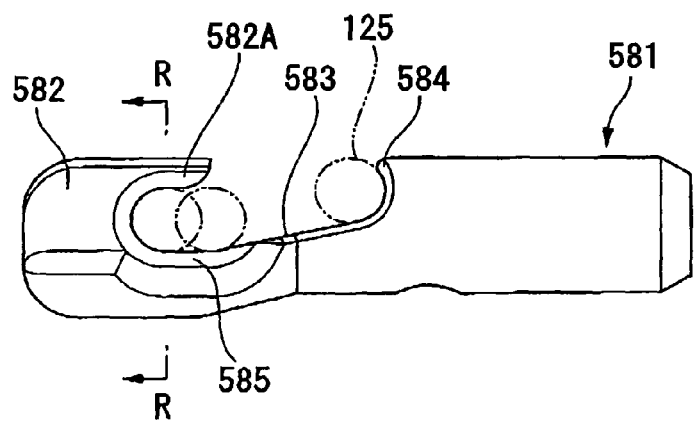
FIG. 43 is an enlarged view of a hook.
Figure 44:
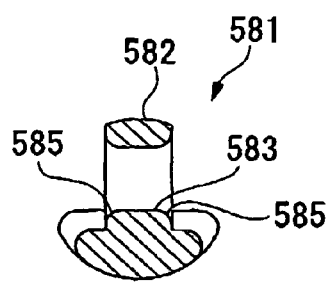
FIG. 44 is a cross-sectional view taken along the line R-R of FIG. 43.

As shown in FIGS. 43 and 44, the hook 581 has an engaging section 582 having a reduced width of its tip part section. The suture thread 125 can be hooked by a barb 582A directed toward the proximal end of the engaging section 582 having a size capable of passing through the suture thread 125 toward the hook sheath 21. The engaging section 582 is manufactured by a cutting operation using a tapered end mill. A proximal end portion is first cut diagonally with a portion of the cutting end mill that is approximately the same as the thread in diameter. A jaw 584 is formed on the proximal end portion of the groove 583. The jaw 584 is disposed offset from the axial line of the hook 581. Similarly, the barb 582A of the engaging section 582 is disposed on the same side to the axial line of the hook 581. Protruding the hook 581 from the coil sheath 41 hooks the suture thread 125 at the jaw 584, thereby preventing the suture thread 125 from detaching therefrom in a process of extending and retracting the hook 581. Also, the suture thread 125 is prevented from detaching the hook 581 by the jaw 584 when the coil sheath 41 is bent. The manufacturing of the hook 581 includes forming a groove 583 through which the suture thread 125 is passed by using a significantly tapered cutting end mill, pressing the expanded-diameter section of the end mill, and forming a chamfering 585 for decreasing the width of the hook 581. A one time machining operation for forming the groove 583 and the chamfering 585 reduces the cost for manufacturing the hook 581.

The hook 581 is manufactured by cutting a material having desirable machinability, e.g., SUS420F2. This reduces the machining time and improves the durability of the cutting tools.

As shown in FIG. 38, the hook sheath 21 is welded to a supporting member 591 accommodated in a cartridge supporting member 372 of a tip cover 560 in accordance with, e.g., a laser welding method. The supporting member 591 has a projection for supporting the casing 150 at the distal end and a through-hole for passing through the hook 581. Further welded to engage the casing 150 are a pair of arms 592. The arms 592 made of an elongated flexible member are bent so that the distal ends pivot to open radially outward by a welded root section welded to the supporting member 591. The tip part sections of the arms 592 are bent inward. Bending the welded arms 592 reduces the assembly time. Since the arms 592 are welded to recesses of the supporting member 591, the outer diameter of the portion of the supporting member 591 corresponding to the welded arms 592 is approximately the same as the other portion. Therefore the arms 592 can make extending and retracting movements smoothly relative to the cartridge supporting member 572.

The proximal end of the cartridge supporting member 572 is reduced in diameter so as to be able to contact the supporting member 591, and the cartridge supporting member 572 has from here an inner diameter approximately equal to the outer diameter of the supporting member 591 while expanding in the axial direction, and the inner diameter is further enlarged to open at the distal end. Since the spacer 601 is inserted from the distal end of an inner hole, the enlarged inner diameter portion is partly formed. Elastic force of the pair of arms 592 of the supporting member 591 recover and open at the inner-diameter-enlarged portion, and the engagement of the casing 150 to the concave portion 202 is released. The arms 592 are closed at the portion where the spacer 601 is inserted, and the arms 592 make contact with a concave portion 202 of the casing 150. The portion where the spacer 601 is inserted corresponds to a position where the curved needle 120 is withdrawn from the casing 150 after the pair of forceps members 115 and 131 are closed. Therefore, the arms 592 pressed and deformed by the spacer 601 engage the casing 150; and the drop-off of the withdrawn curved needle 120 is thus prevented.

The pair of arms 592 are opened to be able to accommodate the attached casing 150 since the supporting member 591 is disposed toward the proximal end. Merely hooking the hook 581 at the loop 125A and drawing the hook 581 completes attaching of the casing 150 to the tip cover 560. Time and effort for attaching the casing 150 are reduced.

Figure 45:
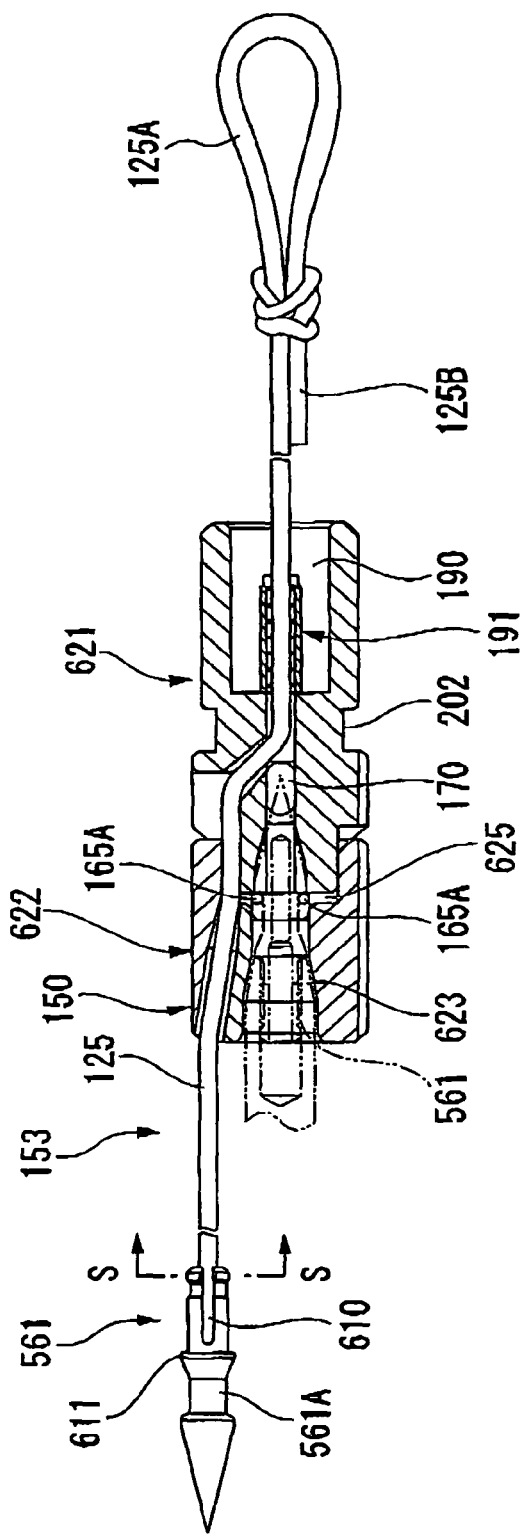
FIG. 45 is a cross sectional view showing a structure of a cartridge.

As shown in FIG. 45, a cartridge (otherwise called a retaining device) 153 is provided with the detachable needle 561, the suture thread 125 crimped and fixed to the detachable needle 561, and the casing 150 through which the suture thread 125 is passed. The detachable needle 561 has an acute distal end and a proximal end having a slot 610 into which the curved needle 120 can be intruded. The dimension of the slot 610 is determined so that the detachable needle 561 can be supported or removed by appropriate force even if the inner diameter of the curved needle 120 has dimensional error. For example, in a case where the detachable needle 561 is 5 mm in total length, the slot 610 is approximately 1.4 mm in length reduces a spring constant, thereby restricting the deviation of the attaching and removing force with respect to the detachable needle 561 and the curved needle 120. Although a contact part 611 contacting the surface of the distal end of the curved needle 120 is disposed to the detachable needle 561, the slot 610 is stopped at a region closer to the proximal end relative to a position where the contact part 611 is formed. The absence of the slot 610 in the part which is inserted into the curved needle 120 prevents the detachable needle 561 from wobbling and facilitates the aligning of the axial line of the curved needle 120 to the axial line of the detachable needle 561.

Figure 46:
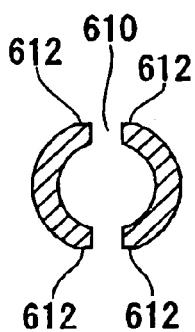
FIG. 46 is a cross-sectional view taken along the line S-S of FIG. 45.

As shown in FIGS. 45 and 46, the proximal end of the detachable needle 561 is cut in a plane orthogonal to a silt forming the slot 610, and the detachable needle 561 is shortened in length in this direction. The end surfaces 612 are cut to have a distance in between so that the curved needle 120 can be inserted in a case where the slot 610 is deformed even if the hole in the curved needle 120 is the minimum of the design tolerance. Although the width in the direction that can be reduced by means of the slot 610 is longer than the distance between the end surfaces 612, this direction can be flexibly modified in accordance with a hole diameter of the curved needle 120 by means of the slot 610. Partly cutting the end portion of the detachable needle 121 permits the dimensional error in the curved needle 120, thereby providing a reliable press-fitting of the detachable needle 561 to the curved needle 120 with moderate force.

As shown in FIG. 45, the suture thread 125 passing through the casing 150 has one end fixed to the detachable needle 561 and the other end having a loop 125A based on the double, drawn-untied knot. The length of the suture thread 125 from the detachable needle 561 to the casing 150 is approximately 35 mm, that is necessary and sufficient for binding a tissue. The portion pulled from the casing 150 reaches the end of the loop 125A, and the length of the portion is approximately 10 mm. This reduces the stroke amount of the hook 581 between the projecting position of the hook 581 and the binding position when the cartridge 153 is attached. Optimizing the length of the suture thread 125 reduces the manipulation with regard to the stroke amount of the hook operating portion 14, thereby facilitating the operation. Shortening the length of the pulled out portion of the casing 150 prevents the suture thread 125 extruded from the casing 150 from being shaggy, thereby preventing the suture thread 125 from clogging in the hook sheath 21.

The length of the end 125B of the suture thread 125 remaining after forming the loop 125A is 2 mm or greater. This prevents the end 125B of the suture thread 125 from clogging or rubbing in the inner surface of the hook sheath 21 when the casing 150 is released. The extending and retracting movement of the casing 150 can be carried out smoothly.

Figure 47:
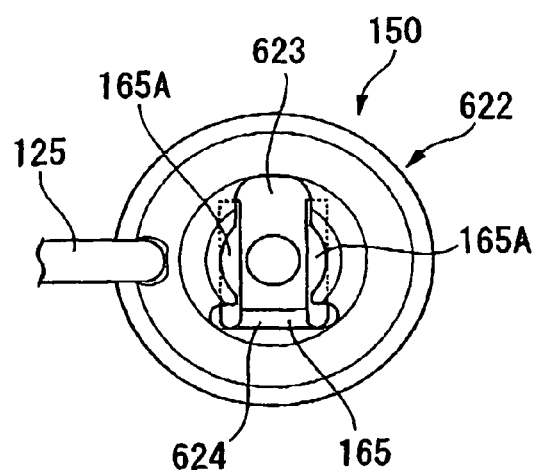
FIG. 47 illustrates a casing viewed from an insertion direction of an detachable needle.

As shown in FIGS. 38 and 45, the casing 150 has a two-piece structure. The member 621 accommodating a wire spring 165 thereinside can be engaged to a supporting member 591. A through-hole 623 that can accommodate a proximal end section of the detachable needle 561 is formed to a member 622 directed toward the distal end. A wire spring 165 having an approximate U-shape in plan view has ends 166 bent approximately orthogonal to the insertion direction of the detachable needle 561. The distance between the pair of bent ends 166 is approximately the same as the outer diameter of the small-diameter part 561A to which the detachable needle 561 is crimped and smaller than the outer diameter of the contact part 611 directed to the proximal end of the detachable needle 561. As shown in FIGS. 45 and 47, formed in the member 622 directed toward the distal end are the through-hole 623 and a hole 624 to which the wire spring 165 can be inserted. The approximate U-shaped portion of the wire spring 165 can be inserted through the hole 624 having a planular shape. The pair of end portions 165A is deformed so as to be the outer diameter of the through-hole 623 or smaller, and the wire spring 165 is then inserted into the holes 623 and 624. Since there is a spacer 625 which accommodates the spread end portions 165A between a distal end member 622 and a proximal end member 621, inserting the wire spring 165 into the spacer 625 opens the end portions 165A, thereby subsequently preventing the removal of the wire spring 165. When the detachable needle 561 is inserted, the pair of end portions 165A are pushed to spread at the distal end of the detachable needle 561. The pair of end portions 165A recover and close at the small-diameter part 561A of the detachable needle 561 into engagement to the detachable needle 561. Since the end portions 165A of the wire spring 165 are hooked on a wall surface of the distal end member 622 in this state, the wire spring 165 locks the detachable needle 561 even if the detachable needle 561 is pulled. Therefore, the detachable needle 561 will not be removed from the casing 150. The configuration where the wire spring 165 is inserted into the distal end permits an integral construction having the distal end member 621 of the casing 150 and the proximal end member 622. The detachable needle 561 can therefore be accommodated reliably.

Conventionally, two components constituting the casing are integrated by using an adhesion method or an ultrasonic welding method. In this case, if the welded section is detached and the distal end of the detachable needle 561 is exposed therefrom, the exposed distal end may possibly contact and damage the tissue. Since the casing 150 has a non-separated, i.e., integral structure in the present embodiment, the wire spring 165 is puckered and inserted into an opening on the distal end that receives the detachable needle 561 during the assembly so that the undercut portion prevents the spread wire spring 165 from being removed.

Figure 48:
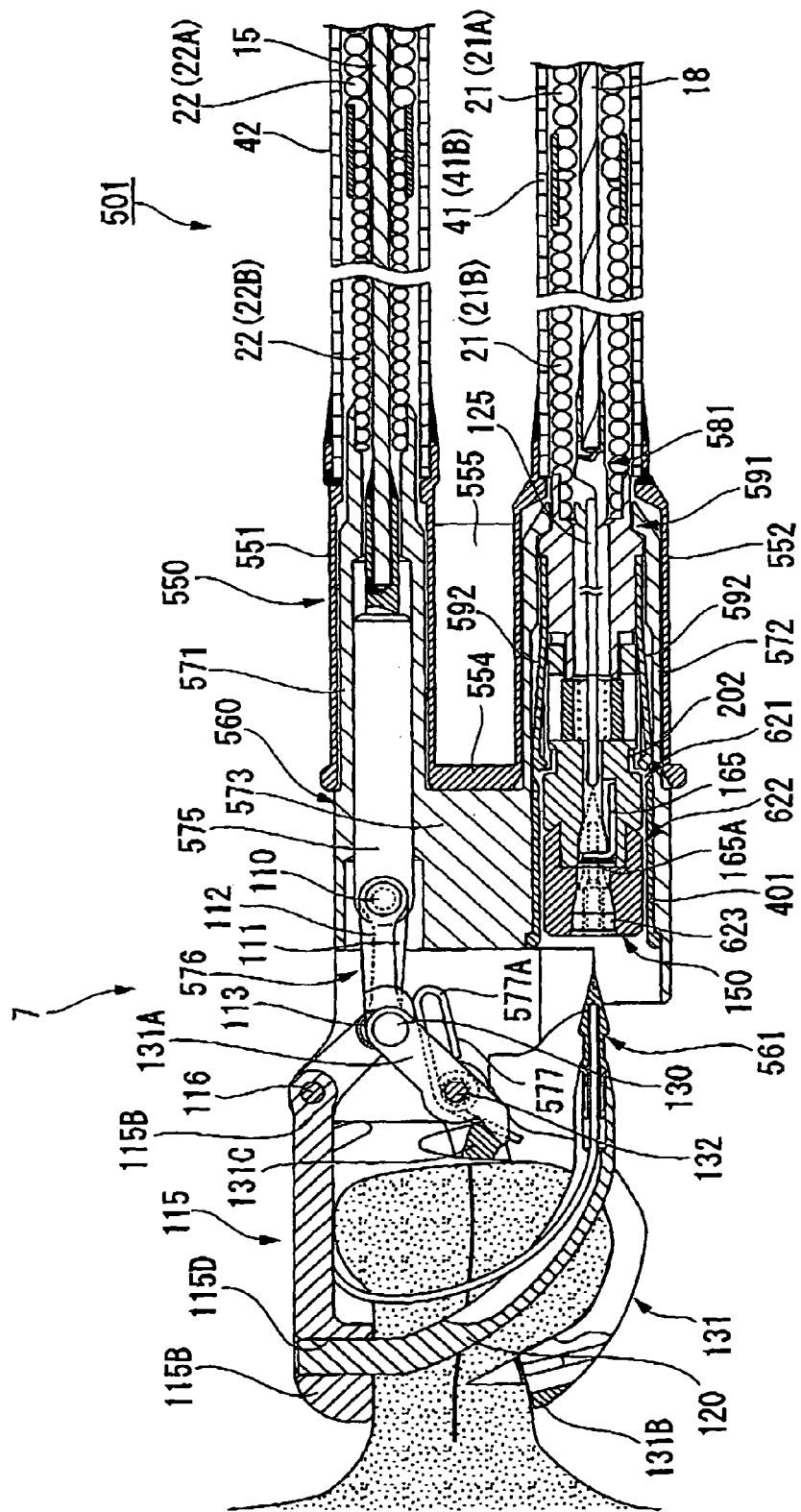
FIG. 48 illustrates a closed sate of the pair of forceps members.
Figure 49:
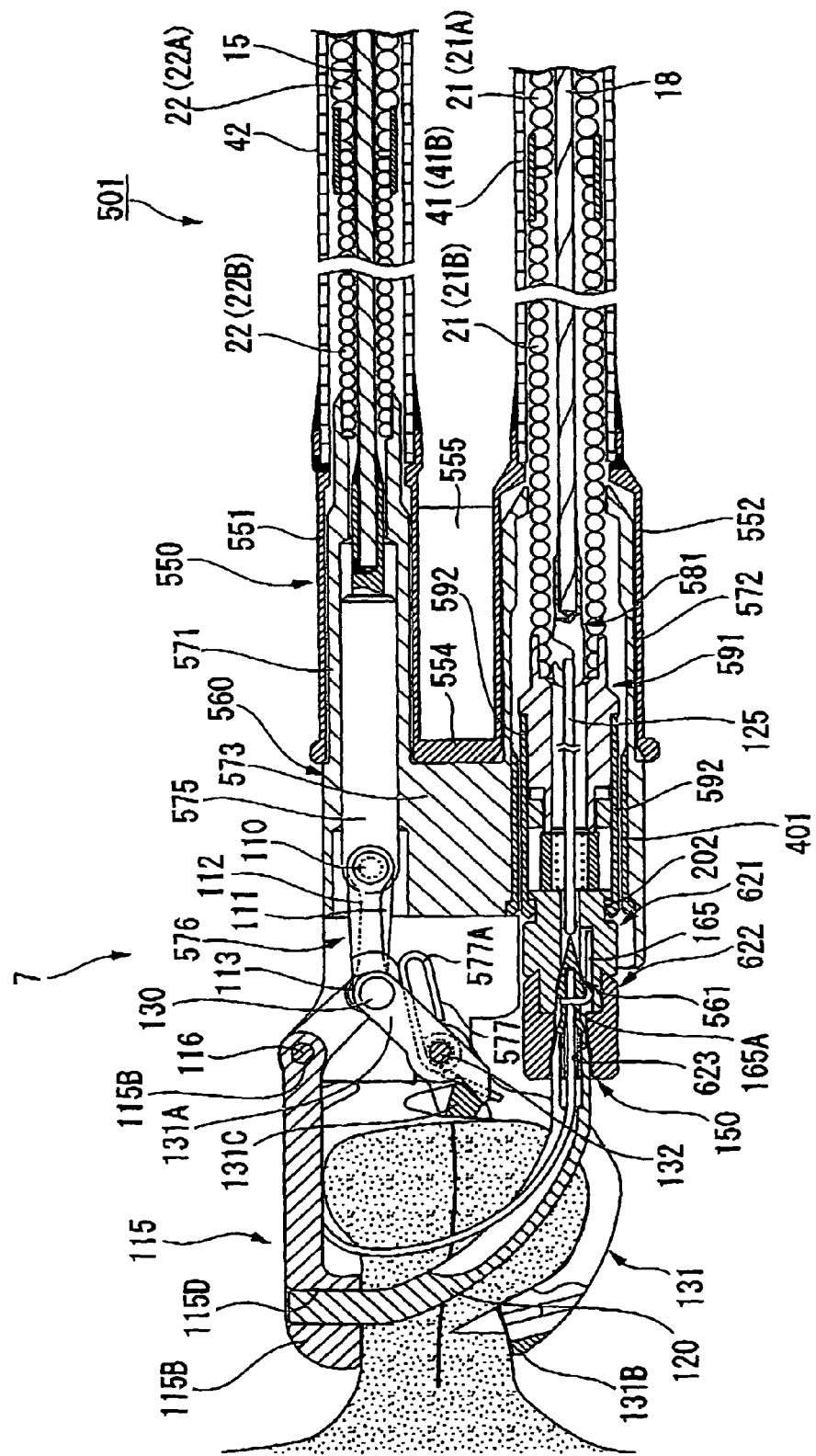
FIG. 49 illustrates an extended casing containing the detachable needle.
Figure 50:
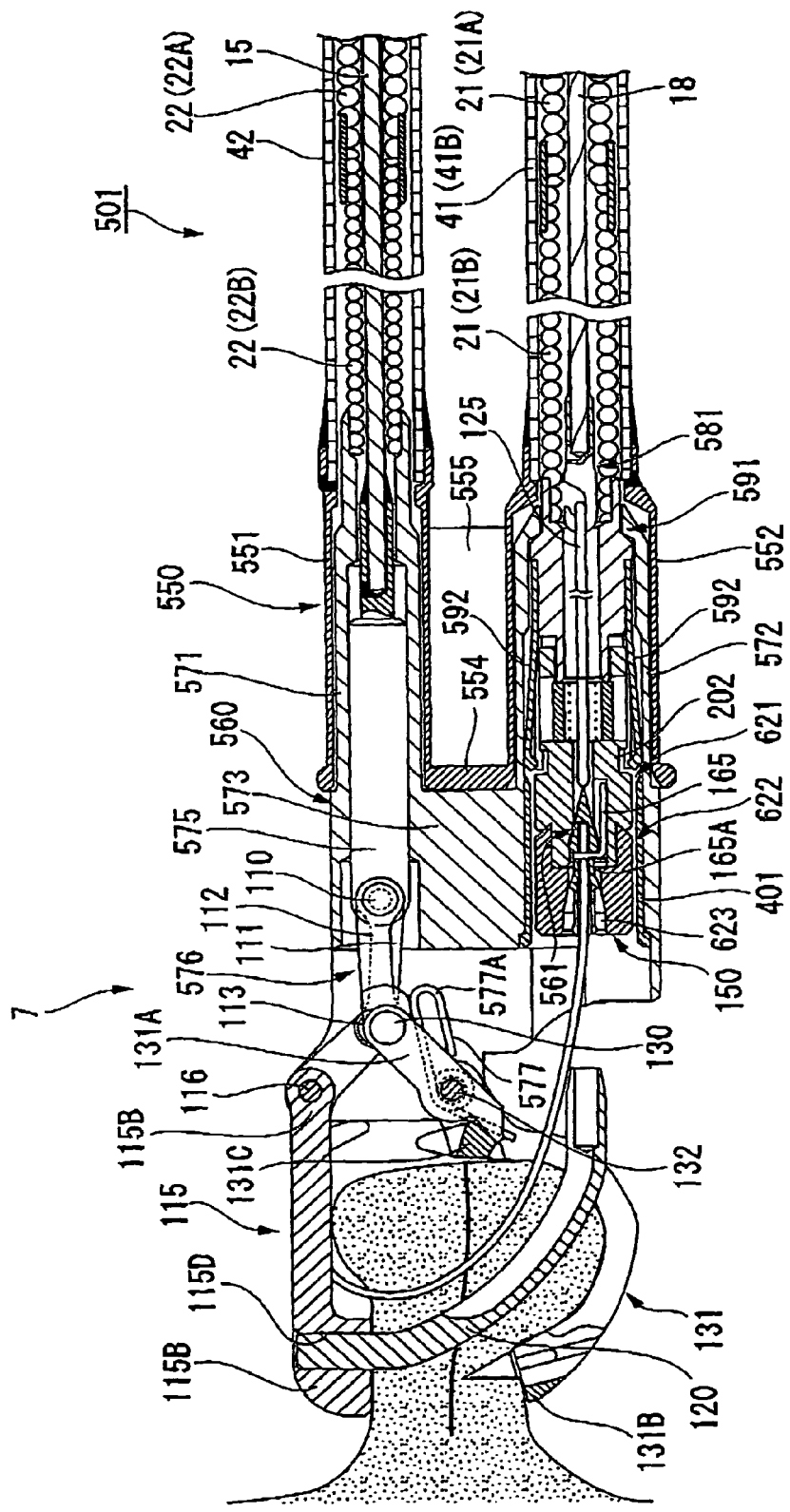
FIG. 50 illustrates the casing withdrawn to be separate from the detachable needle.
Figure 51:
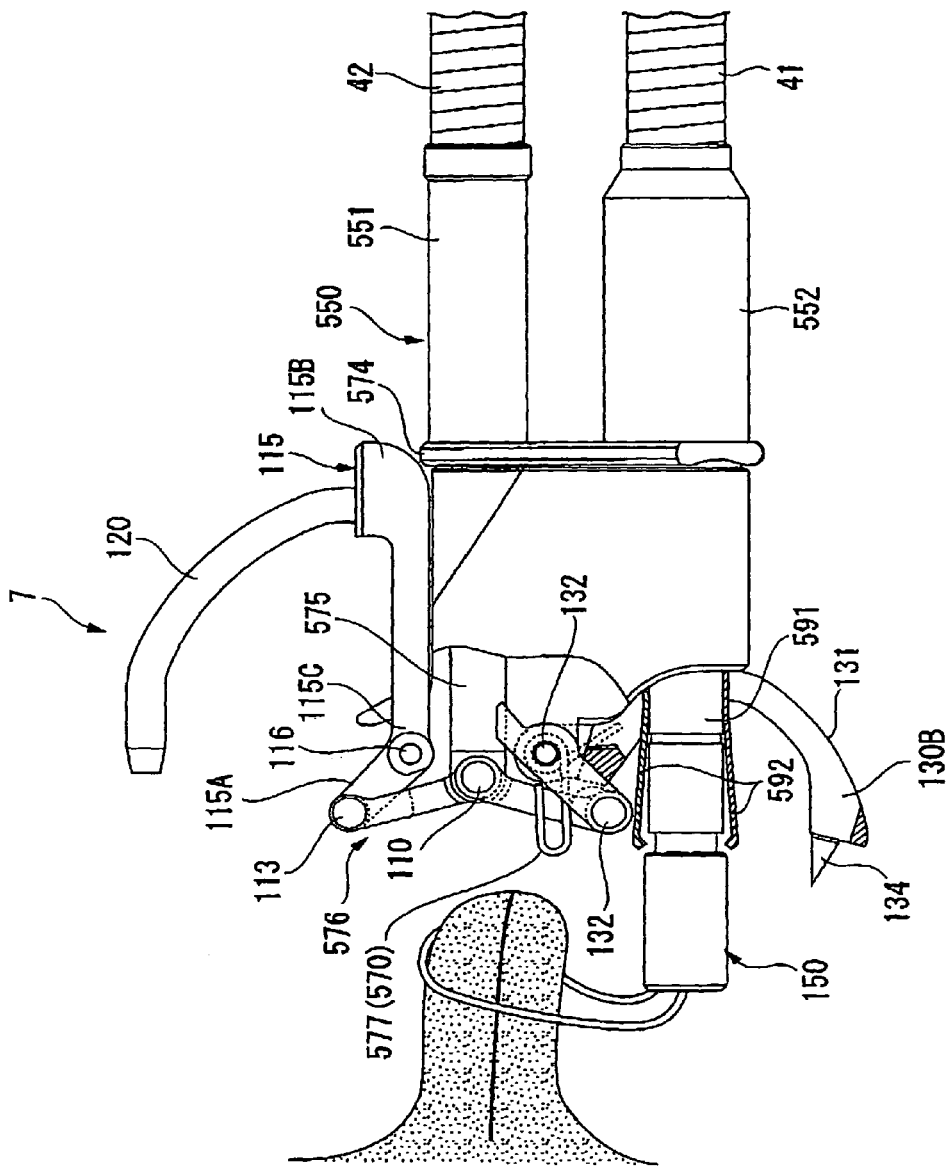
FIG. 51 illustrates an extruded state of casing from the open pair of forceps members.

The pair of forceps members 115 and 131 are closed and the curved needle 120 is inserted into the tissue when the tissue is bound with the cartridge 153. As shown in FIG. 48, the detachable needle 561 directed to a manipulation side is disposed coaxially with the casing 150. When the hook sheath 21 is manipulated to extend, the detachable needle 561 is inserted into the casing 150 as shown in FIG. 49. Since a pair of arms 392 pushed and closed by the spacer 601 then tightens the concave portion 202, the spacer 601 will not be dropped off or the axis will not be deviated. After the detachable needle 561 is locked by the wire spring 165, the hook sheath 21 is manipulated to be withdrawn. As shown in FIG. 50, the detachable needle 561 removed from the curved needle 120 is drawn in the tip cover 560 together with the casing 150.

The pair of forceps members 115 and 131 are then opened to extend the hook sheath 21. As shown in FIG. 50, upon projecting the casing 150 ahead of the tip cover 560, the hook operating portion 14 is manipulated and pulled to retract the hook 581. The pulled suture thread 125 constricts the tissue. The hook sheath 21 is retracted after binding the tissue, and the casing 150 is removed from the supporting member 591 by extending the hook 581. The hook 581 is projected from the supporting member 591 to remove the suture thread 125 from the hook 581. The cartridge 153 is retained while binding the tissue.

Third Embodiment

Figure 52:
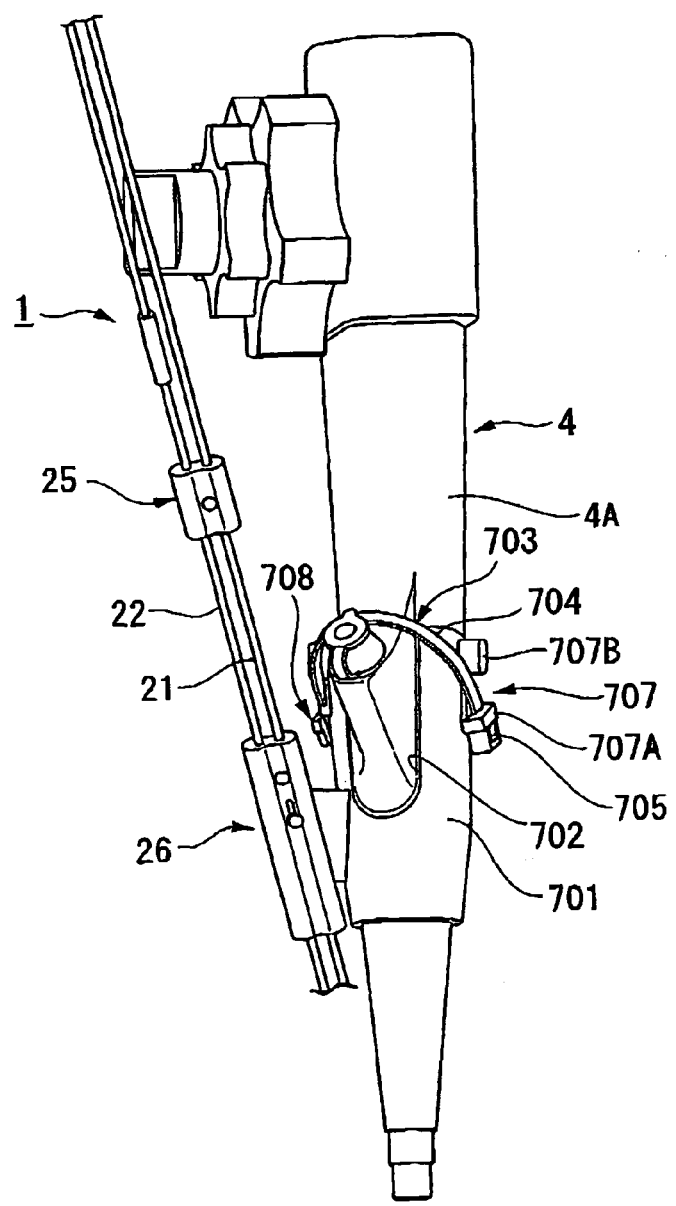
FIG. 52 is a view showing a scope holder attached to the endoscope.

As shown in FIG. 52, provided to a scope holder 26 is a receiving portion 701 attached to an endoscope operation section 4A. A cut 702 corresponding to a forceps plug section 4B is formed at the receiving portion 701 having an approximate C-letter shape in cross section. Before attaching the scope holder 26 to the endoscope 4, the receiving portion 701 is fit into the endoscope operation section 4A and fastened by a binding band 703 disposed across a forceps plug section 4B. A locking head section 705 is integrally disposed to one end of an elongated band section 704 of the binding band 703. A rack is disposed on the band section 704 along the longitudinal direction. The binding band 703 is locked to two attaching sections 707 and 708 disposed across the cut 702 of the receiving portion 701.

Figure 53:
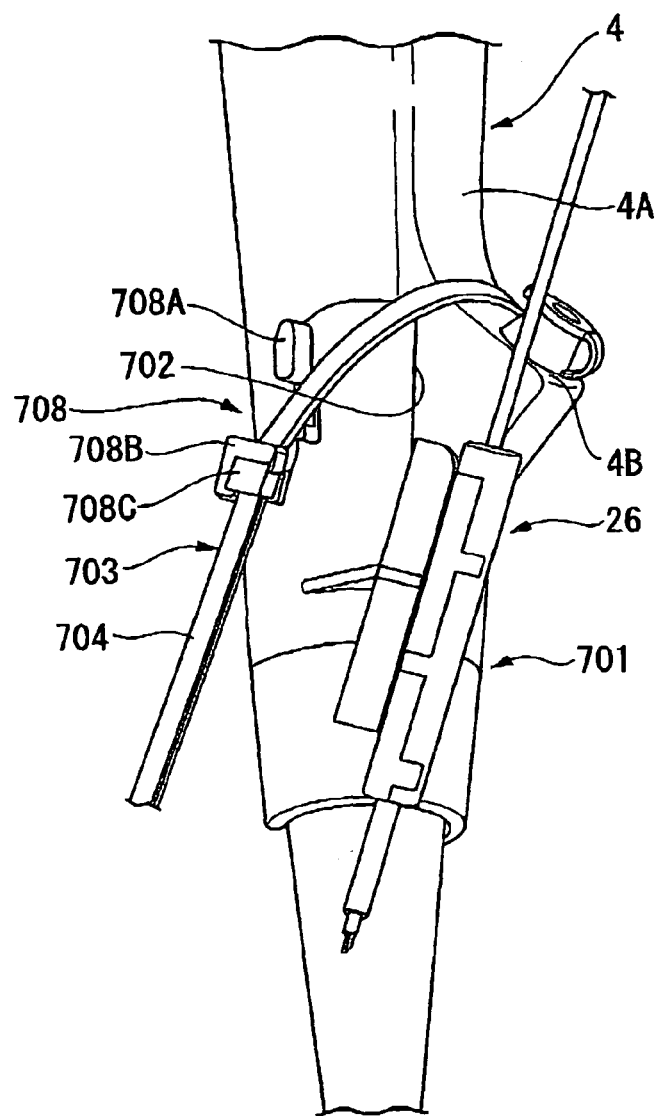
FIG. 53 illustrates the scope holder viewed from a half end.

One of the attaching section 707 has an insertion portion 707A that permits the band section 704 to pass therethrough but does not pass the locking head section 705; and a protrusion 707B for preventing the band section 704 from shifting. As shown in FIG. 53, provided to the other attaching section 708 are a protrusion 708A for preventing the band section 704 from shifting; and an insertion portion 708B for passing the band section 704 therethrough. Furthermore, fixed to the insertion portion 708B is a locking section 708C having a ratchet claw engaging the rack of the band section 704. The ratchet claw and the rack engage in the withdrawing direction of the band section 704 but not in the insertion direction of the band section 704. The scope holder 26 can be attached to the endoscope 4 of an arbitrary type since the forceps plug section 4B is fastened and fixed by the binding band 703. Also, the fastening, by means of the binding band 703, tightly fixes the suture instrument to the endoscope 4.

Figure 54:
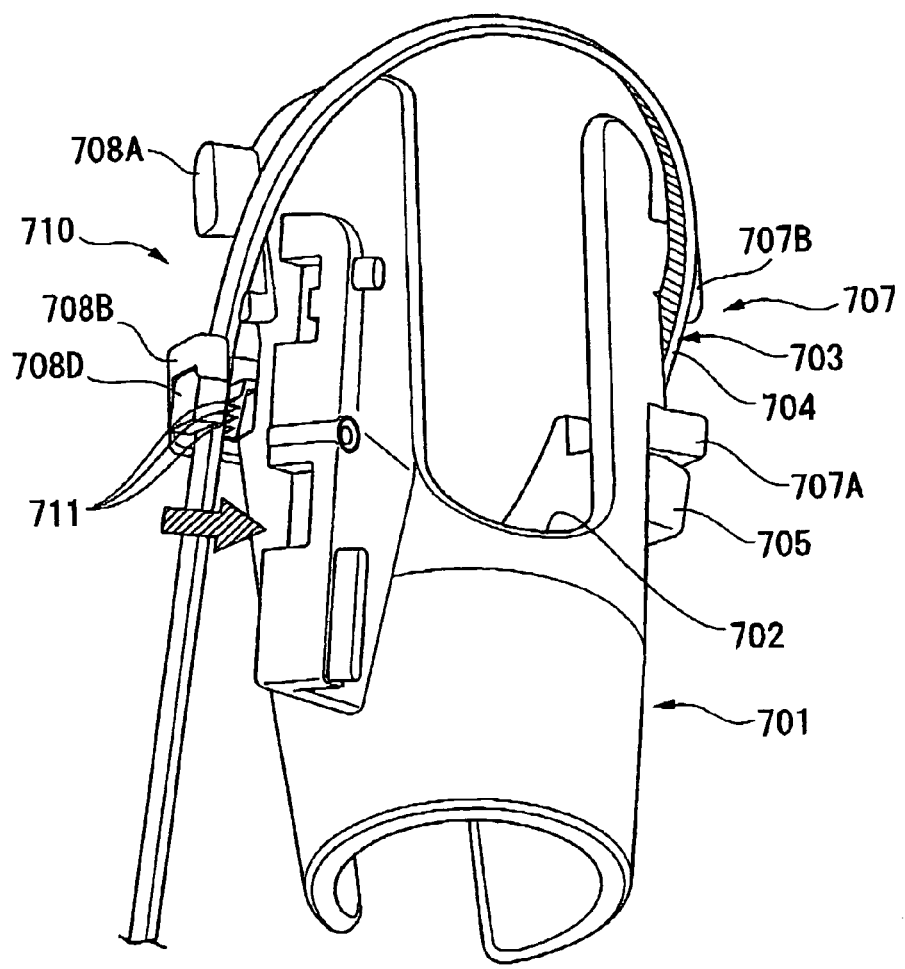
FIG. 54 is a view showing an example of the scope holder.

A modified example of the present embodiment will be explained as follows. A scope holder 26 shown in FIG. 54 has an attaching member 710 of a receiving portion 701 in construction. The attaching member 710 has a locking section 708D. The locking section 708D is cut in a direction orthogonal to the insertion direction of the band section 704, and thus a ratchet claw 711 is exposed. When the scope holder 26 is attached to the endoscope 4, the binding band 703 is inserted into a attaching section 707, and the other end of the band section 704 is passed and pulled through the attaching section 708. When the scope holder 26 is detached from the endoscope 4, the band section 704 having passed through the band section 704 is slid in a direction approximately orthogonal to the insertion direction indicated by an arrow shown in FIG. 53, and the band section 704 is extracted from the cut surface. The binding band 703 can be reused.

Figure 55:
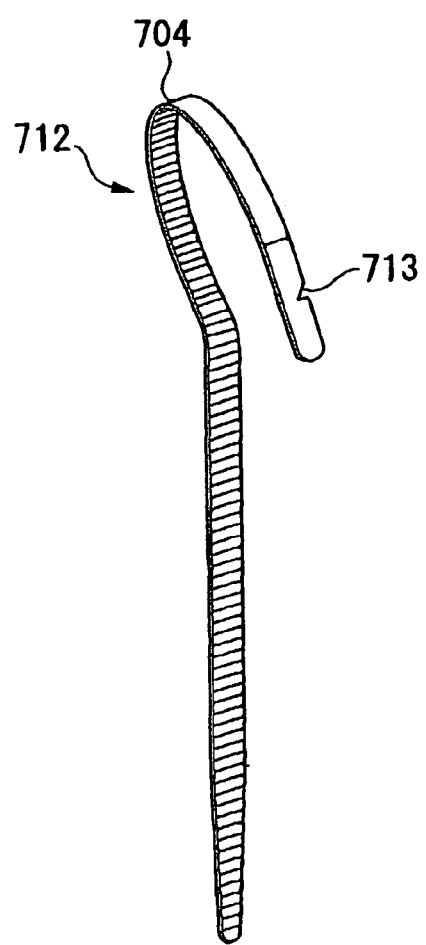
FIG. 55 is a view showing a modified example of a binding band.
Figure 56:
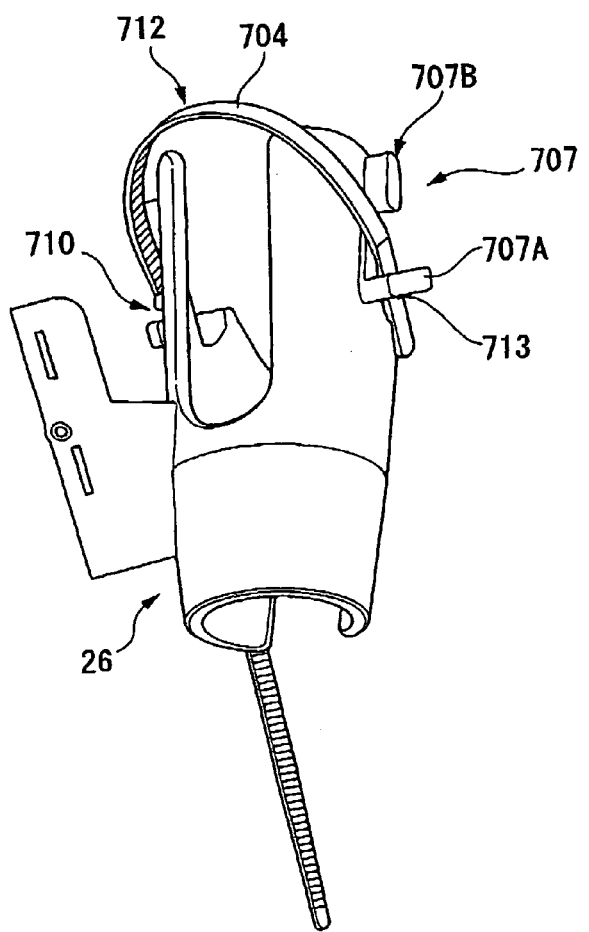
FIG. 56 shows the scope holder using the binding band shown in FIG. 55.

Also, a binding band 712 as shown in FIG. 55 may be used. A cut 713 having an approximate V-letter shape is formed to an end portion of the band section 704 of the binding band 712. When the scope holder 26 is attached to the endoscope 4, the binding band 712 is inserted from the attaching section 707. As shown in FIG. 56, the cut 713 of the band section 704 is hooked at the insertion portion 707A. The other end of the band section 704 is passed and pulled through the attaching member 710. When the scope holder 26 is detached from the endoscope 4, the band section 704 having passed through the locking section 708D is slid to extract the band section 704. Since the cut 513 is merely hooked to the attaching section 707, the binding band 712 can be detached without difficulty. The binding band 712 can be reused.

Figure 57:
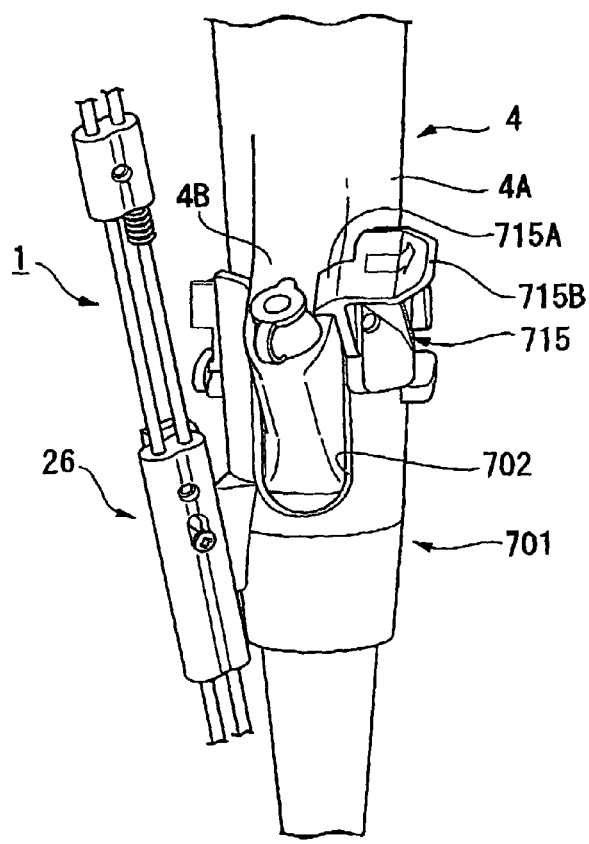
FIG. 57 illustrates the scope holder unitarily formed with a locking member.

Also, as shown in FIG. 57, an elastic deformable locking section 715 may be disposed to integrally extend from an outer periphery of the cut 702 of the receiving portion 701. Provided to the locking section 715 are a projecting claw 715A for locking to the forceps plug section 4B; and an integrally formed lever 715B for operating the unlocking of claw 715A. When the receiving portion 701 is attached to the endoscope 4, pressing the lever 715B to deform the locking section 715, thereby opening the claw 715A. After the receiving portion 701 in this state is attached to the endoscope 4, the lever 715B is unclasped. The locking section 715 recovers and locks the claw 715A to the forceps plug section 4B, thereby the scope holder 26 is fixed. One-touch lever operation enables the scope holder 26 to be attached to the endoscope 4. Incidentally, the locking section 715 may be separate from the receiving portion 701.

Fourth Embodiment

Figure 39:
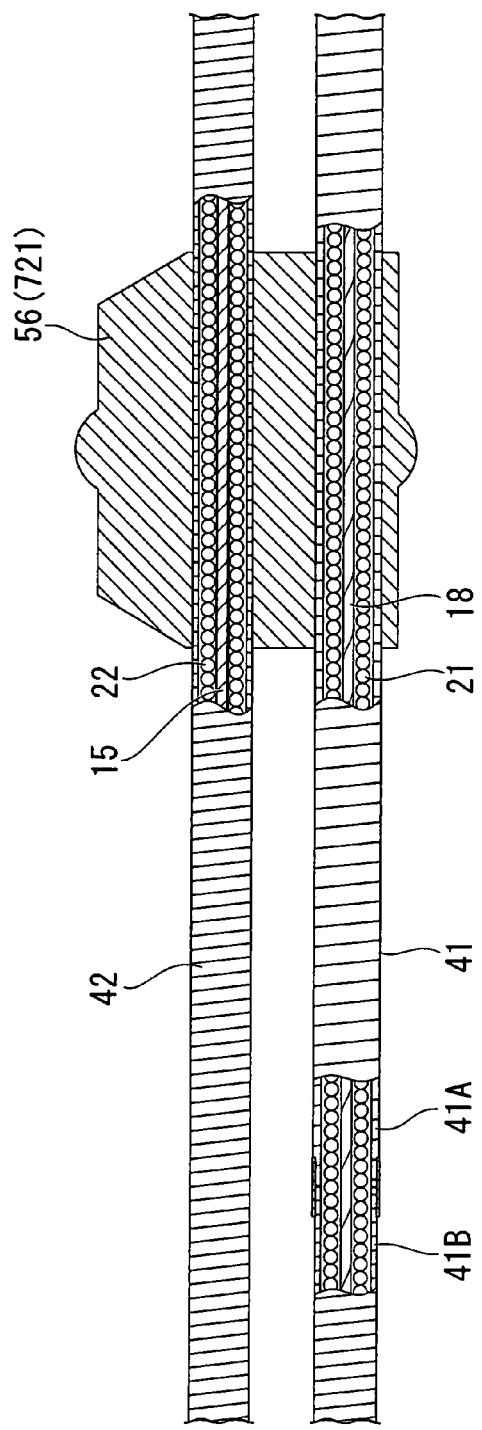
FIG. 39 is a partial cross sectional view showing a structure of an insertion portion.
Figure 58:
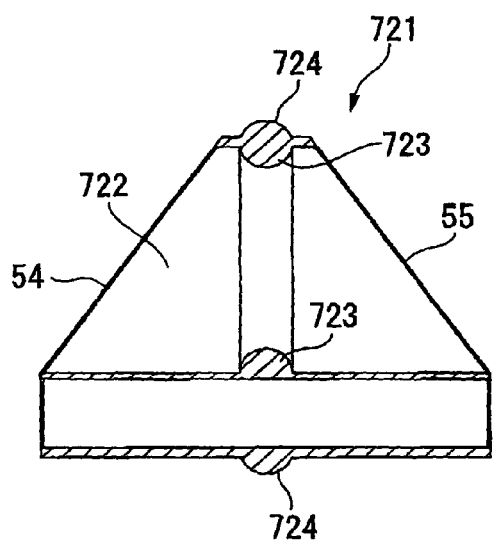
FIG. 58 is a cross sectional view showing another aspect of a valving element.

As shown in FIG. 39 and FIG. 58, a valving element 721 for bundling the two coil sheaths 41 and 42, and the endoscope inserting part 5 of the endoscope 4 has a through-hole 722 having a larger diameter than that of the valving element 50 according to the first embodiment. Little contact between an inner circumference of the valving element 721 and the inserted endoscope inserting part 5 facilitates the insertion of the endoscope 4. Also, the diameter of a press-fit part 723 of the valving element 721 is smaller than that of the first embodiment. Even if a press-fit part 723 is crushed by the inserted endoscope 4, the reduced area making contact with the endoscope 4 facilitates the insertion of the endoscope 4. This valving element 721 enhances the operability for inserting the endoscope 4.

Also, the diameter of the press-fit part 724 around the outer circumference of the valving element 721 is reduced in order to decrease the sliding resistance subjected to the insertion of the valving element 721 into the overtube 6. Even if a press-fit part 724 is crushed in the overtube 6, the reduced contacting area facilitates the insertion. Incidentally, these press-fit parts 724 are configured to have a size where airtightness and slidability can be compatibly established.

The hardness of a rubber constituting the valving element 721 is decreased from conventional 50° to, for example, 40° in order to decrease the sliding resistance subjected to the insertion of the valving element 721 into the overtube 6. It is possible to decrease the force required to insert the valving element 721 into the overtube 6 and reduce treating time and stress accompanying the operation.

Fifth Embodiment

Figure 59:
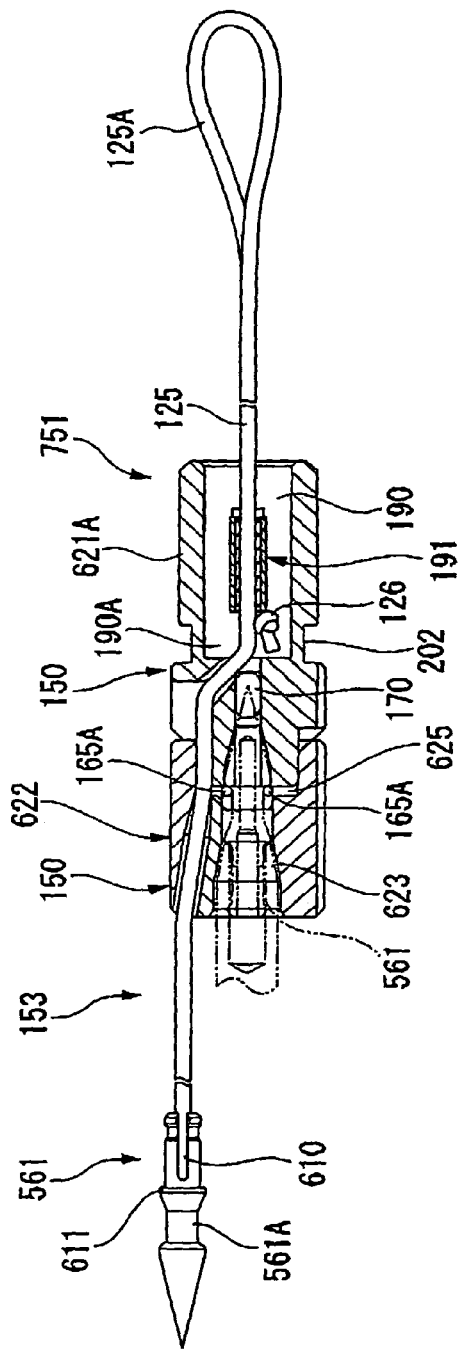
FIG. 59A is a side cross sectional view of a cartridge in a modified example.
FIG. 59B is a cross sectional view illustrating a modified example of the cartridge shown in FIG. 59A.
Figure 60:
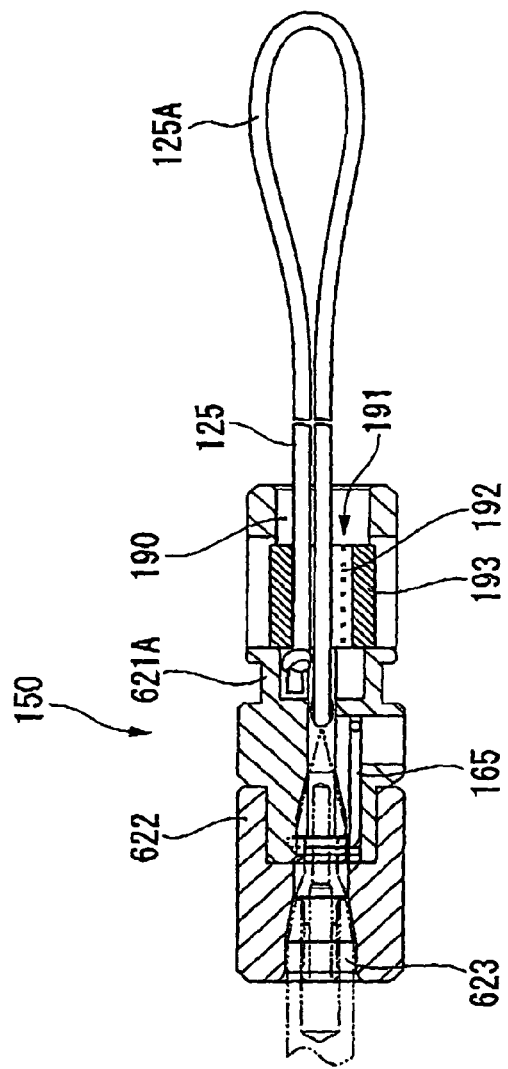
FIG. 60 is a plan cross sectional view of the cartridge shown in FIGS. 59A and 59B.

FIG. 59 and FIG. 60 show a modification example of the cartridge. Also, FIG. 61 illustrates a hook used together with the cartridge.

A suture thread 125 is passed through a casing 150 of the cartridge 751, and a detachable needle 561 is attached to the suture thread 125. The suture thread 125 upon having passed through a brake portion 191 in a hole 190 of a proximal end member 621A is extracted, returned in the outside of the casing 150, and reentered into the member 621A. Thus, a loop 125A of the suture thread 125. The end portion of the suture thread 125 pulled into the casing 150 is crimped and fixed to the brake portion 191 accommodated in the hole 190. A knot 126 formed there serves as a removal stopper. The means for fixing the suture thread 125 may be a crimped structure or a knot 126.

Apparently two suture threads 125 are extending from the member 621A of the cartridge 751 since the loop 125A of the suture thread 125 extends into the member 621A.

Figure 61:
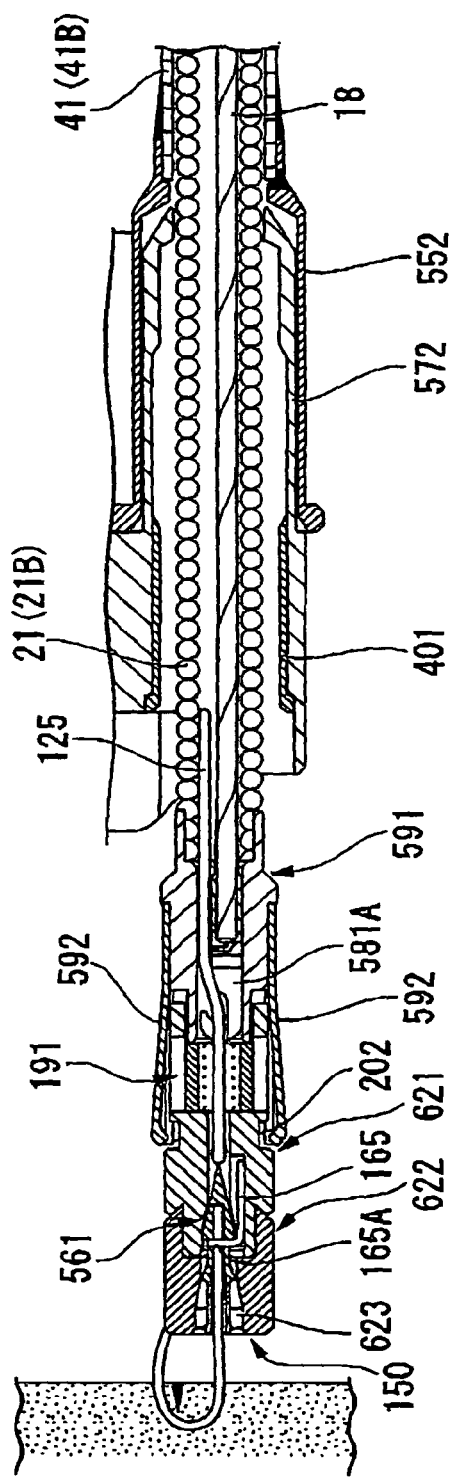
FIG. 61 is a modified example of the hook in an enlarged view showing a tip portion of the suture instrument.
Figure 62:
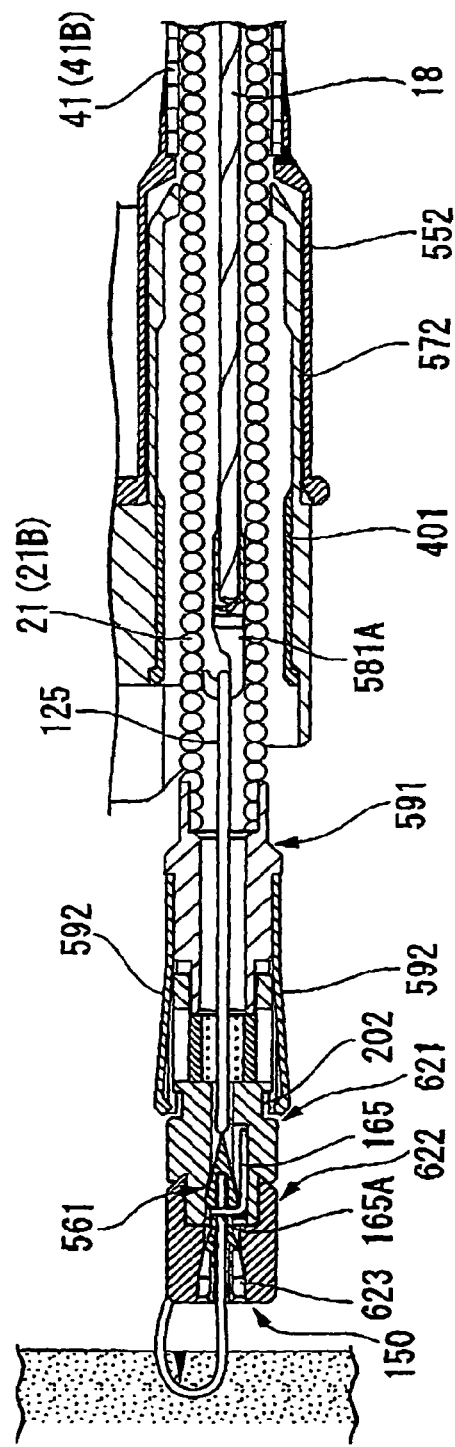
FIG. 62 shows a withdrawn state of a suture thread pulled by the hook.

Extending the hook 581A expels the suture thread 125 into a space between the hook 581A and a sheath 21, thereby extending only the hook 581A since the hook 581A shown in FIG. 61 does not have an overhang shape, i.e., the proximal end through which the suture thread 125 is passed does not expand toward the distal end. Extending the hook 581A further into contact with the brake portion 191 reliably separates the casing 150. Incidentally, when a tissue is bound, the hook 581A is retracted as shown in FIG. 62. The loop 125A of the suture thread 125 hooked on the hook 581A provides constriction of the suture thread 125.

The use of the hook 581A facilitates to push the casing 150, thereby reliably extruding the casing 150.

Although a space 190A that can accommodate the knot 126 is disposed on an axial line of the hole 190 of the casing 150 in the example shown in FIG. 59A, the space 190A directed toward the distal end may be omitted. In this case, the knot 126 is returned to the manipulation side to be accommodated in the hole 190 as shown in FIG. 59B.

Sixth Embodiment

Figure 63:
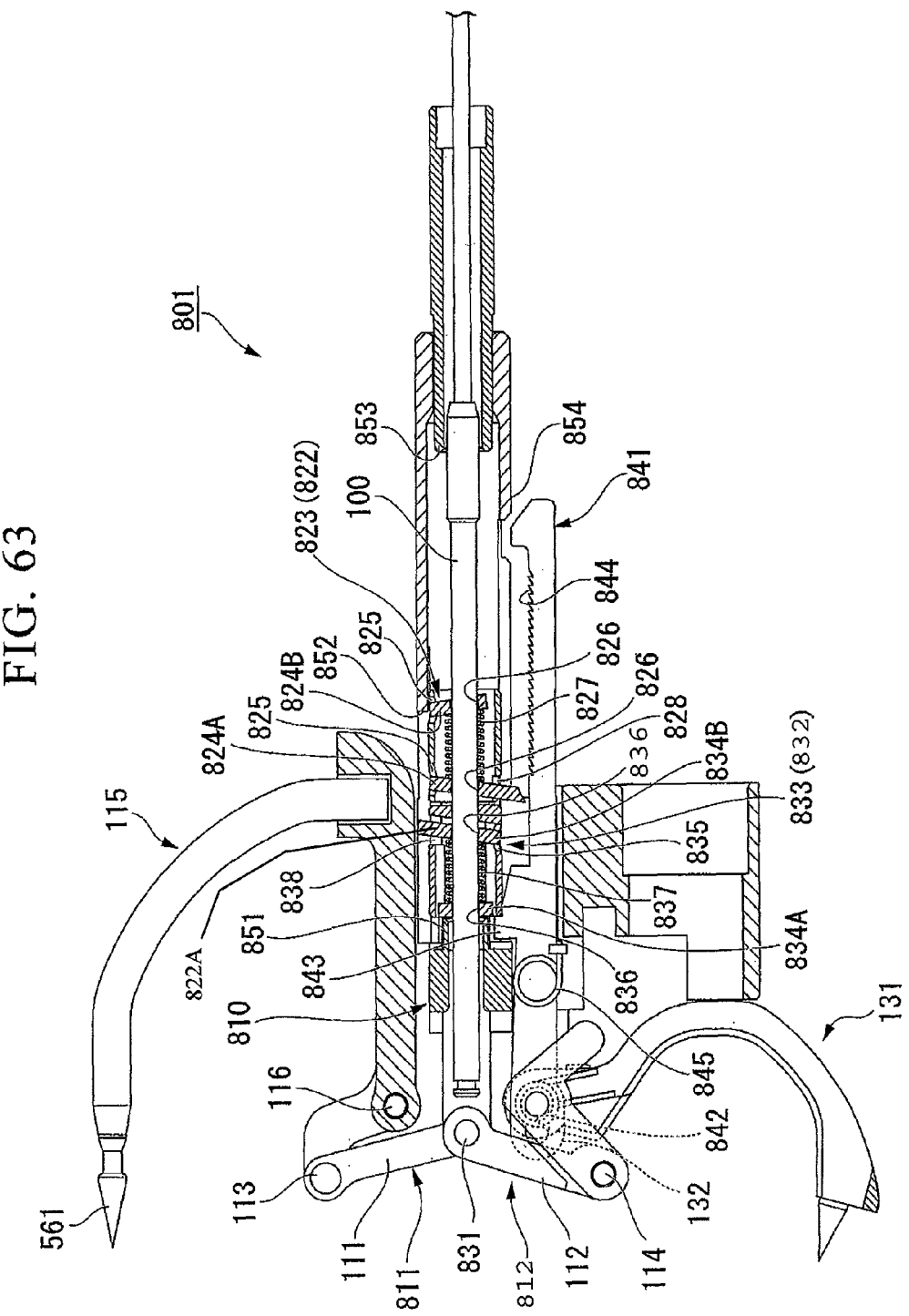
FIG. 63 is a cross sectional view showing the distal end portion of a suture instrument where forceps members are driven by separate links.

FIG. 63 illustrates a treatment section 807 in a cross sectional view of a suture instrument 801 (applicator) as an endoscopic treatment instrument. Incidentally, the structure for holding the casing 150 may be that of the second embodiment.

Figure 64:
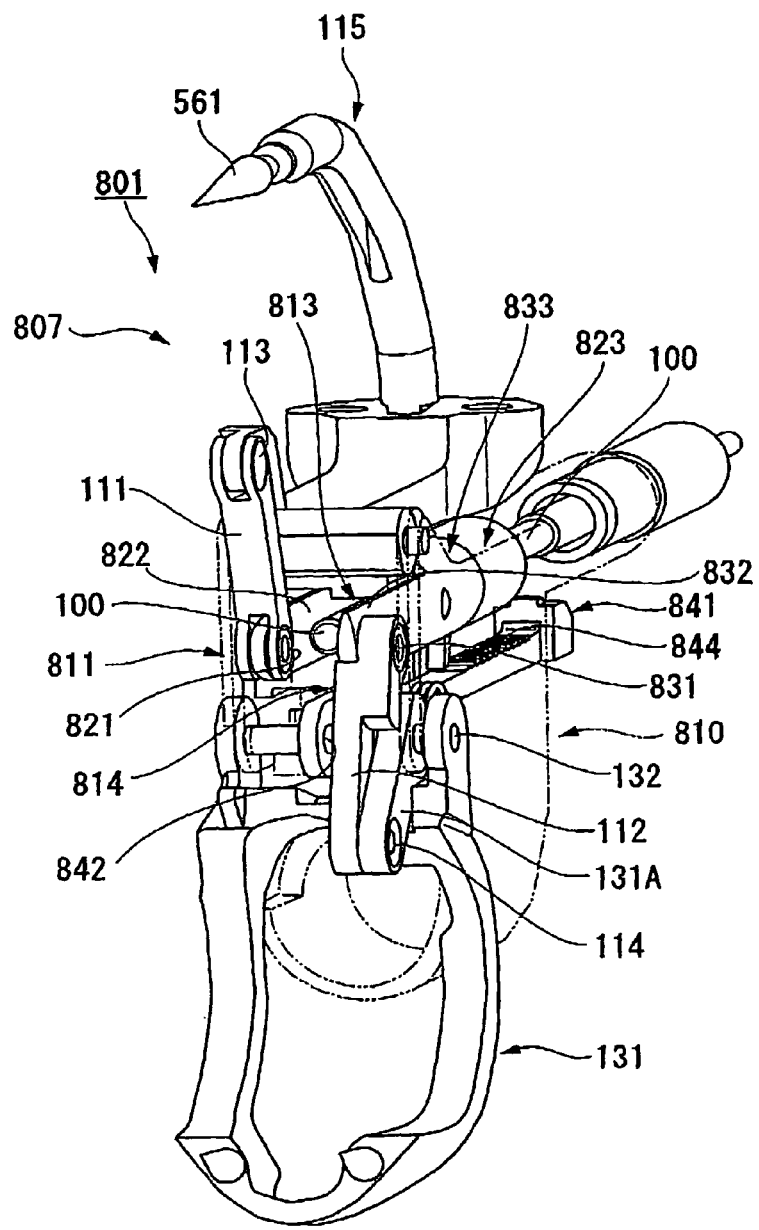
FIG. 64 is a perspective view for explaining the disposition of the links.

As shown in FIGS. 63 and 64, provided to the treatment section 807 are a first finger-hook ring 811 for rotating a forceps member 115 as a first forceps member in a tip cover 810; and a second finger-hook ring 812 for rotating the forceps member 131 as a second forceps member.

A freely extending and retractable connection rod 822 is connected to a link member 111 of the first finger-hook ring 811 via a pin 821. The connection rod 822 extending in parallel with a rod 100 as an inputting member is supported by a tip cover 810. The proximal end portion of the connection rod 822 is a first connecting portion 823 through which the connection rod 822 is passed. Two control plates 824A and 824B are disposed alternately with respect to an extending and retracting direction of the rod 100 in the first connecting portion 823. These freely inclinating control plates 824A and 824B each are inserted into two slits 825 disposed in the first connecting portion 823. The control plates 824A and 824B each have one hole 826 through which a rod 100 is inserted. A coiled spring 827 disposed along the rod 100 to compress the inclined control plates 824A and 824B allows end portions of the plates directed toward the slit 825 to access each other while the other end portions are separate from each other. The hole 826 is configured in size so that the inclined control plates 824A and 824B engage the rod 100 and control plates 824A and 824B standing orthogonal to the axial line form a clearance relative to the rod 100. The distal end control plate 824A projects through the slit 828 into the opposite end.

A freely extending and retractable connection rod 832 is connected to a link member 112 of the second finger-hook ring 812 via a pin 831. The connection rod 832 is supported by the tip cover 810 in parallel with the rod 100 opposite to the first finger-hook ring 811 relative to the rod 100. The distal end portion of the connection rod 832 relative to the first connecting portion 823 of the first finger-hook ring 811 forms a second connecting portion 833. The freely extending and retractable rod 100 is passed through the second connecting portion 833, and two control plates 834A and 834B are alternately disposed thereinside with respect to the extending and retracting direction of the rod 100. The control plates 834A and 834B directed toward the distal end are inserted at a rotated direction of 90° around the axial line relative to the control plates 824A and 824B of the first finger-hook ring 811. The control plate 834A capable of freely inclining is passed through a slit, not shown in the drawing, formed in the second connecting portion 833. The control plate 834B is inserted at a rotated direction of 180° around the axial line relative to the control plates 824A and 824B. The control plate 834B capable of freely inclining is passed through a slit 835 of the second connecting portion 833. The rod 100 inserted through the hole 836 formed in the control plates 834A and 834B each has a coiled spring 837 disposed along thereof. Thus, the control plates 834A and 834B are urged to separate from each other. The hole 836 is configured in size so that the inclined control plates 834A and 834B engage the rod 100 and control plates 834A and 834B standing orthogonal to the axial line form a clearance relative to the rod 100. The distal end control plate 834A projects through the slit 838 into the opposite end.

In addition, an approximately parallel lock arm 841 is disposed closer to the hook sheath 21 relative to the rod 100. The freely swinging lock arm 841 is supported by the tip cover 810 via a pin 132 inserted through an elongated hole 842. The lock arm 841 has a protrusion 843 capable of engaging the distal end of the second connecting portion 833 of the connection rod 832 and a rack 844 capable of engaging the control plate 834A so that a barb of the end portion of the rack 844 projects toward the rod 100. The lock arm 841 is urged by a pressure spring 845 between the elongated hole 842 and the protrusion 843 so that the distal end is directed toward the rod 100.

Incidentally provided to the tip cover 810 is an abutment section 851 that allows the control plate 834A to make contact with the distal end of the second connecting portion 833. An abutment section 852 to which the projecting portion 822A of the connection rod 822 pressed by the control plate 834B can make contact is provided and is directed to the proximal end relative to the control plate 834B as shown in FIG. 63 illustrating an initial position. Provided further in the vicinity of the distal end of the rod 100 is a abutment section 853 capable of making contact with the control plate 824B. Provided in addition is a ground portion 854, onto which the lock arm 841 overrides, for permitting a space between the control plate 824A and the lock arm 841.

The operation of the suture instrument 801 will be explained.

Figure 65:
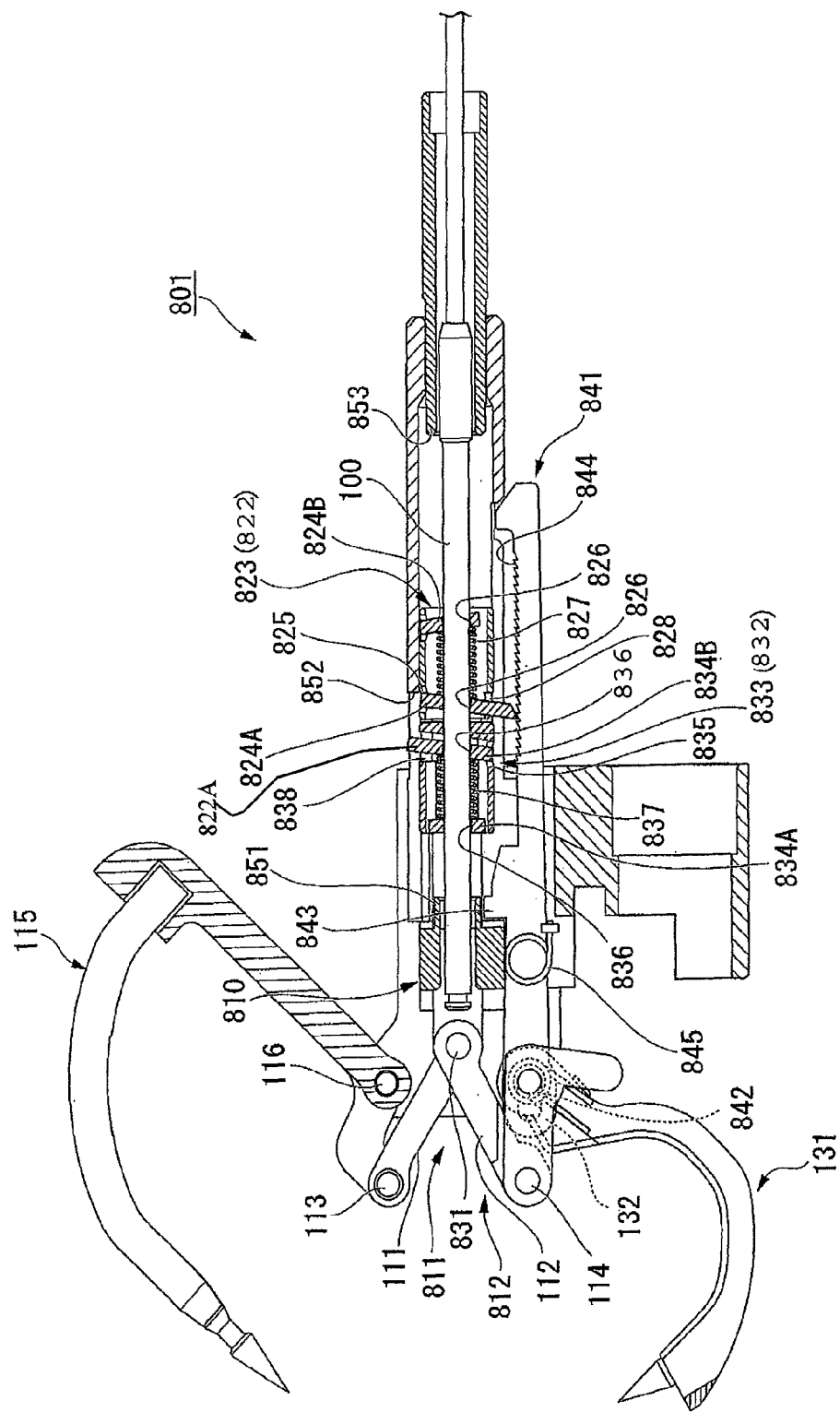
FIG. 65 illustrates a process for rotating the pair of forceps members in the closing directions.

When the opening state of a pair of forceps members 115 and 131 is closed, the rod 100 is retracted. The links 811 and 812 each are connected to the rod 100 by inclining the control plates 824B and 834B directed to the proximal end. The pair of forceps members 115 and 131 are therefore rotated in the closing direction in accordance with the retracting rod 100 as shown in FIG. 65. Retracting the connection rod 822 of the second finger-hook ring 812 disengages the protrusion 843 from the connection rod 822. The proximal end of the lock arm 841 directed to the proximal end of the suture instrument 801 is rotated toward the rod 100 urged by the pressure spring 845. However, the lock arm 841 rotated by the urging force of the lock arm 841 does not engage the control plate 824A moving in the direction corresponding to the clearance angle of the rack 844 of the lock arm 841.

Figure 66:
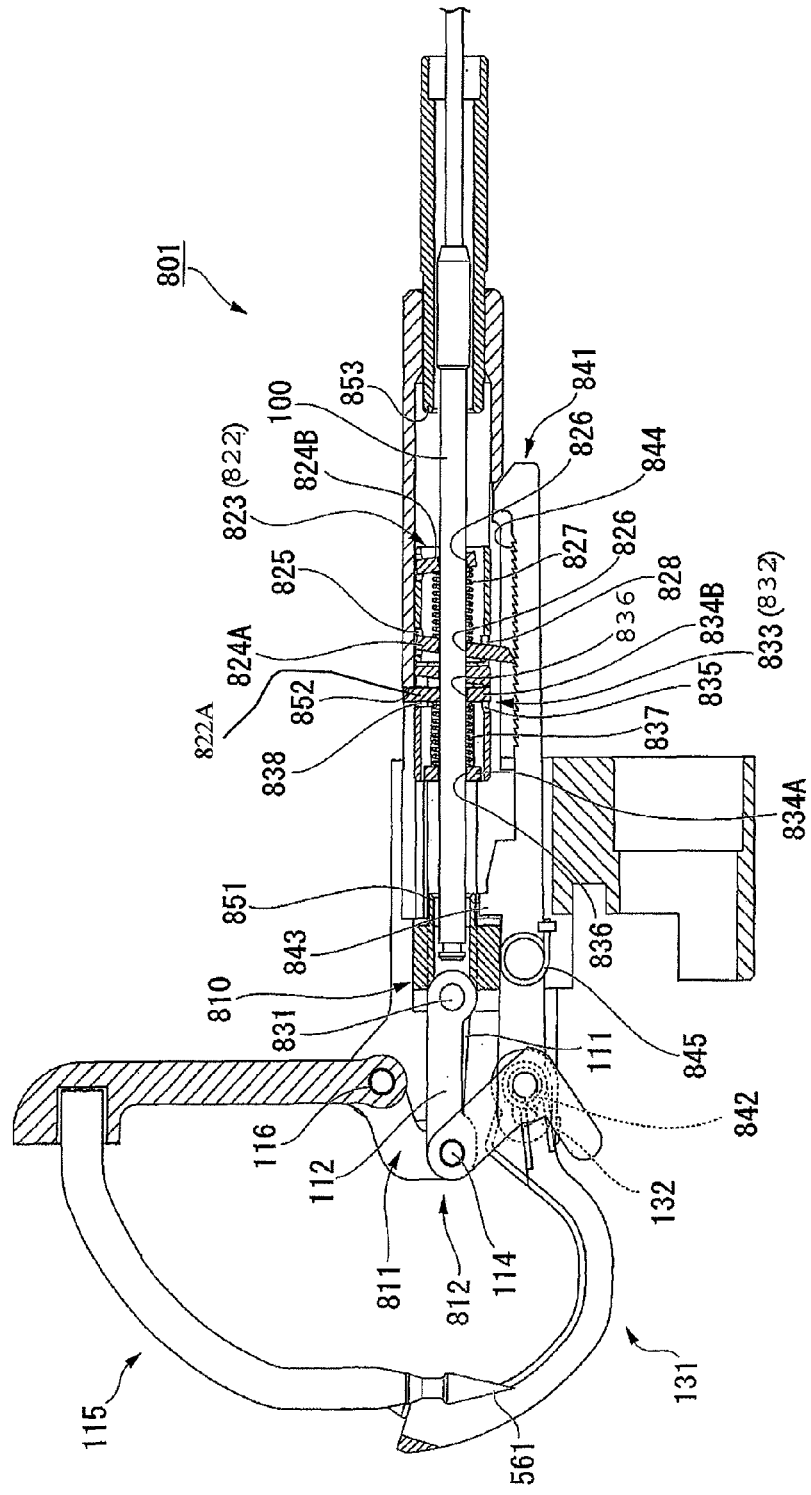
FIG. 66 illustrates the rotated state of both of the pair of forceps members by 90°.
Figure 67:
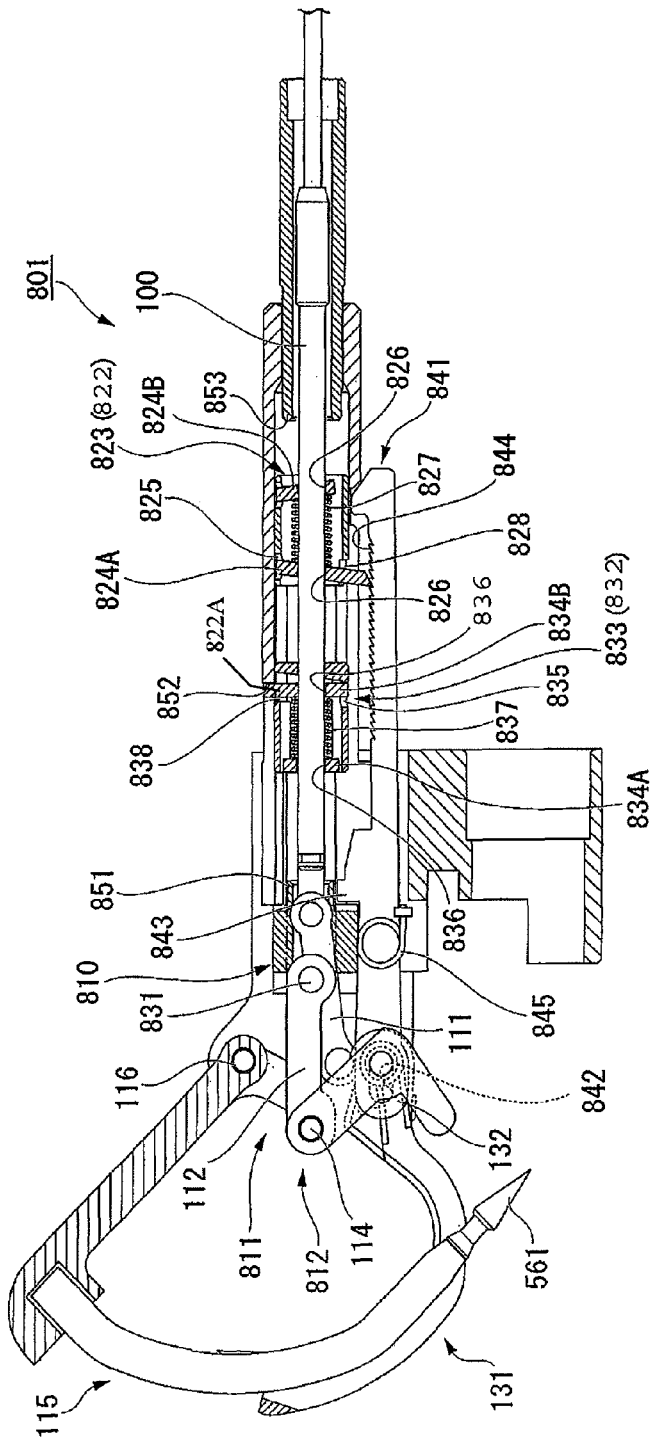
FIG. 67 illustrates the fully closed and stopped forceps member and a 135° rotated state of the not fully closed forceps member.

The rotation of the pair of forceps members 115 and 131 by a degree of 90° relative to the initial state shown in FIG. 66 allows the control plate 834B of the second finger-hook ring 812 to make contact with the abutment section 852 of the tip cover 810. The control plate 834B pushed by the abutment section 852 is returned to an approximately vertical direction while resisting the coiled spring 837. The connection between the second finger-hook ring 812 and the rod 100 is released. As shown in FIG. 67, pulling further the rod 100 rotates only the forceps member 115 while the forceps member 131 connected to the rod 100 does not rotate.

Figure 68:
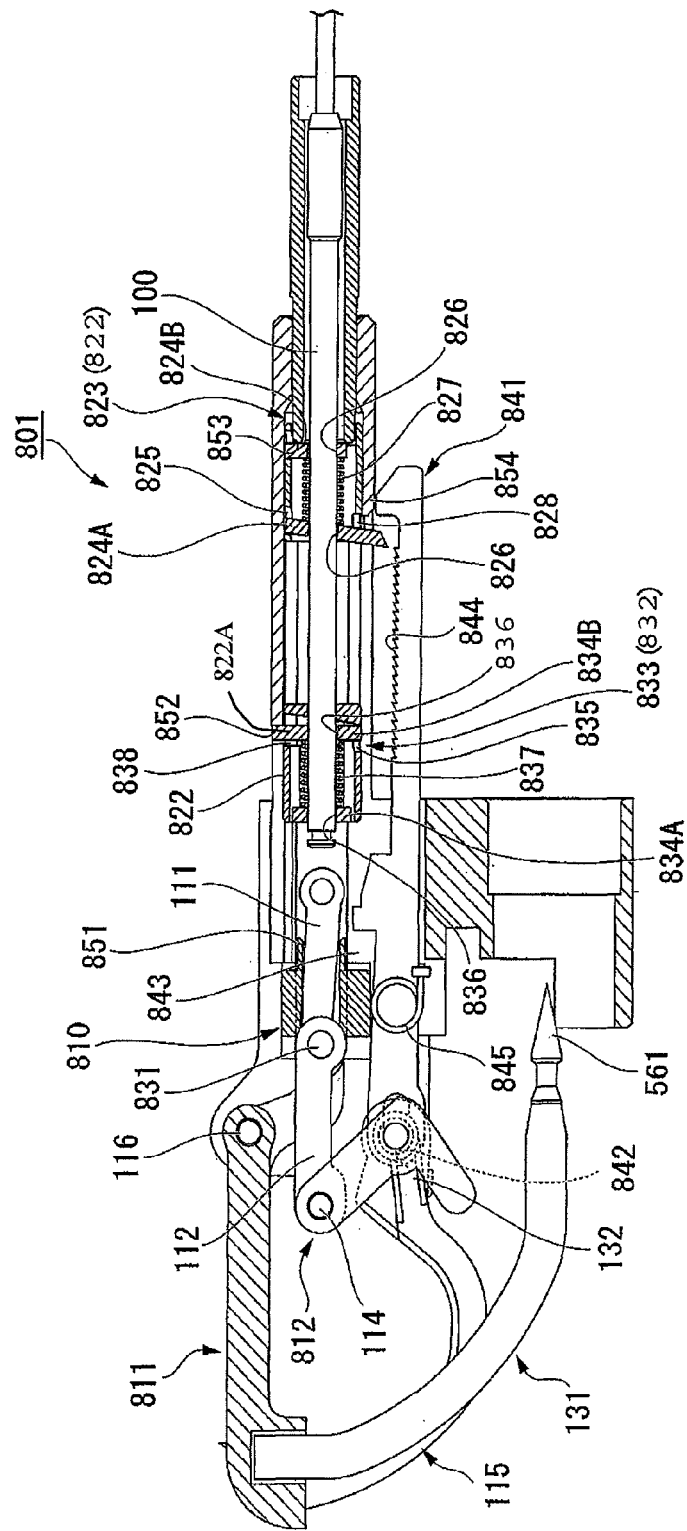
FIG. 68 illustrates a closed state of the pair of forceps members.

As shown in FIG. 68, closing the forceps members 115 and 131 allows the control plate 824B of the first finger-hook ring 811 to make contact with the abutment section 853. The control plate 824B pushed by the abutment section 853 is returned to an approximately vertical direction while resisting the coiled spring 827. That results in the disconnection between the second finger-hook ring 811 and the rod 100. This position is equivalent to the most withdrawn position of the rod 100. Even if the lock arm 841 is disposed on the ground portion 854 and the control plates 824A and 824B moves, uninterfered state with the ratchet claw 844 is maintained since the lock arm 841 hooked on the control plates 824A and 824B moves in the withdrawing direction of the rod 100.

Figure 69:
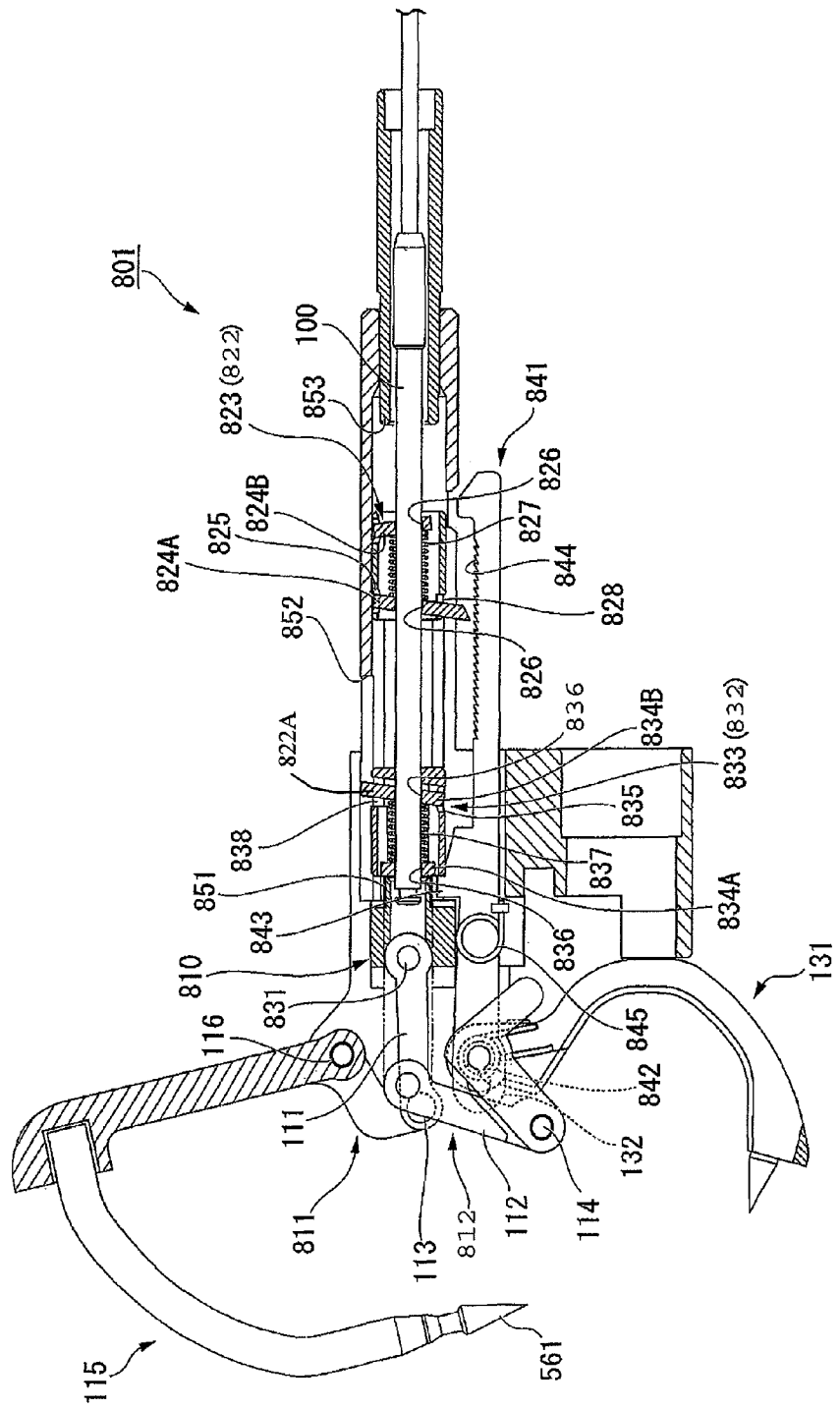
FIG. 69 illustrates the forceps members rotated from the closed state to the open state.
Figure 70:
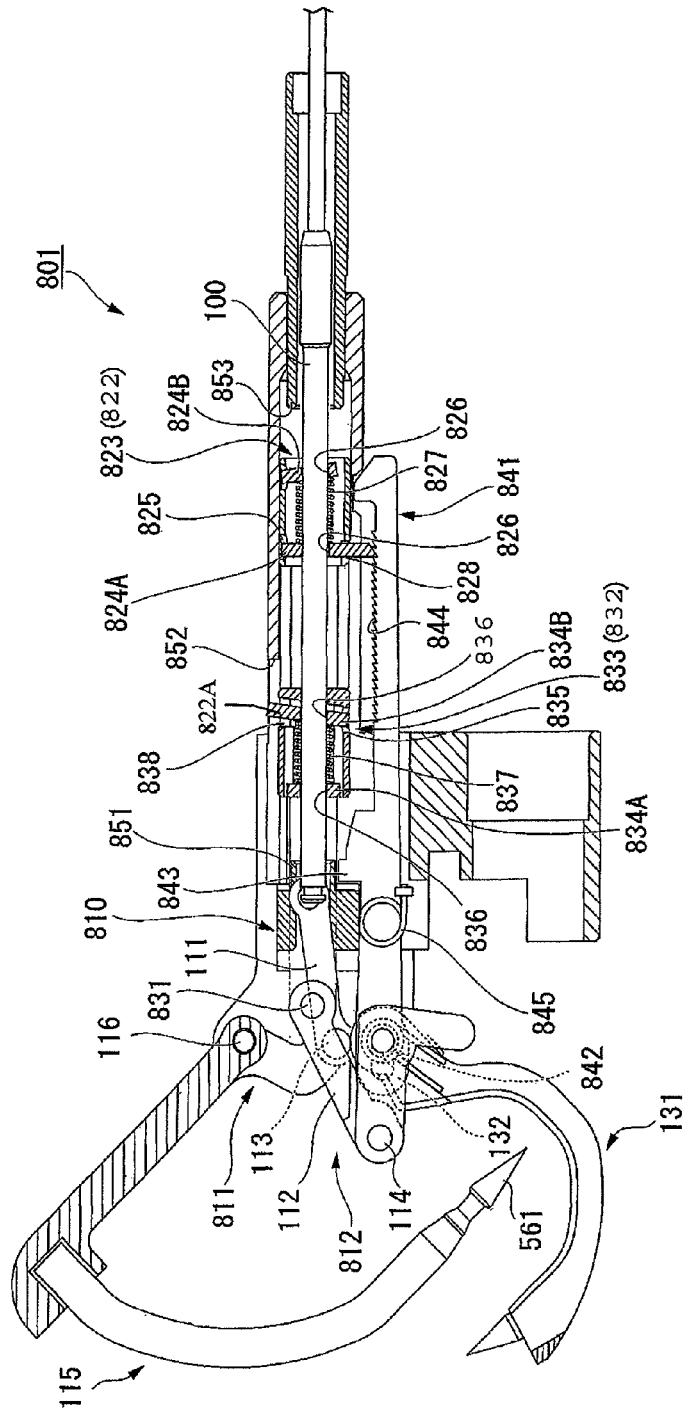
FIG. 70 illustrates the forceps members shown in FIG. 67 rotated in the opening direction.

Extending the rod 100 from the closed state of the pair of forceps members 115 and 131 connects the second finger-hook ring 812 to the rod 100 due to the connection between the distal end control plate 834A and the rod 100, thereby opening the forceps member 131. The lock arm 841, while riding on the connection rod 822 and pushed, moves toward the distal end immediately before the forceps member 131 fully opens. The forceps member 115 opens since the first finger-hook ring 811 is simultaneously in conjunction with the rod 100 due to the engagement between the rod 100 and the distal end control plate 824A inclined by the lock arm 841. As shown in FIG. 69, the control plate 834A making contact with the distal end abutment section 851 where the rotated forceps member 131 by an angle of 90° opens resists the coiled spring 837, and is pushed back approximately orthogonally. The forceps member 131 therefore does not move afterward if the rod 100 is extended. The forceps member 115 opens by approximately 180° beyond 90° due to the engaged state of the first finger-hook ring 811.

Figure 71:
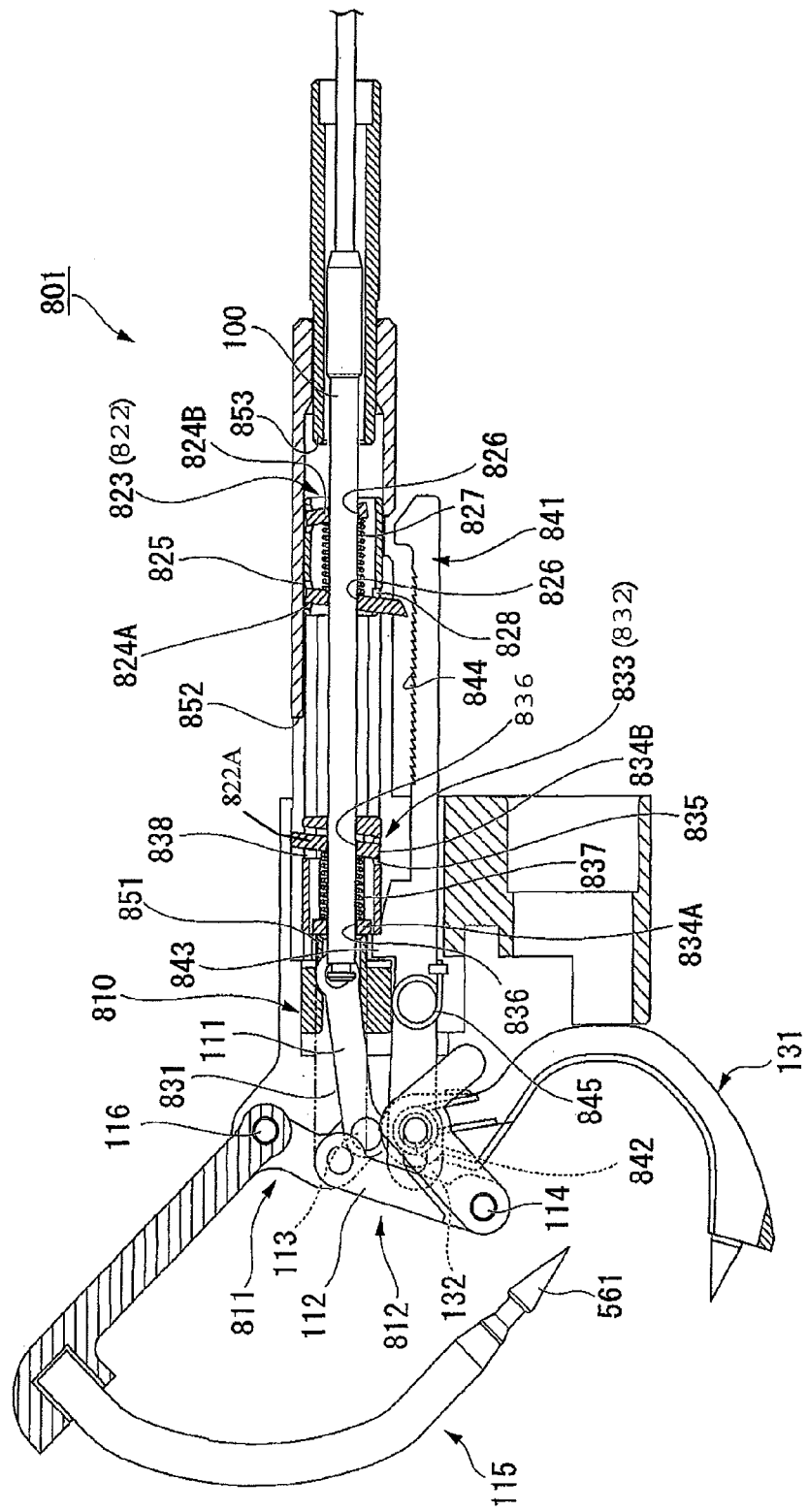
FIG. 71 illustrates an actuated state of the forceps members.

Pushing back the rod 100 halfway from the position shown in FIG. 67 permits the forceps members 115 and 131 to open in turn. As shown in FIG. 65, the rack 844 of the lock arm 841 engaging the control plate 824A of the first finger-hook ring 811 disposes the control plate 824A vertically. That results in the disconnection between the second finger-hook ring 811 and the rod 100. The forceps member 115 does not open while only the forceps member 131 opens. As shown in FIG. 71, the control plate 834A making contact with the abutment section 851 when the forceps member 131 opens by 90° disconnects the second finger-hook ring 812 from the rod 100.

In the present embodiment, two connecting portions 823 and 833 are detachably connected to one rod 100, and each connecting portions have points for connecting and disconnecting in the extending and retracting direction of the rod 100; thus, the forceps members 115 and 131 are rotatable independently. Therefore, it is possible to regrip the tissue, reinsert the needle, and grip an intended tissue reliably.

The variations of the opening and closing operation of the pair of forceps members 115 and 131 will be explained with reference to FIGS. 72 to 75. In the drawings, the abscissas indicate time, and the ordinates indicate a rotational angle of the forceps members 115 and 131 from the open state. Lines S1 indicate a trace of changing strokes of the rod 100, and the larger numbers indicate a more significant retraction. Lines S2 indicate the trace of rotational angle of the forceps member 115 based on the strokes of the rod 100. Lines S3 indicate the trace of rotational angle of the forceps member 131 based on the strokes of the rod 100. The rotational angle of 0° on the lines S2 and S3 indicates the fully open position of the forceps members 115 and 131.

Figure 72:
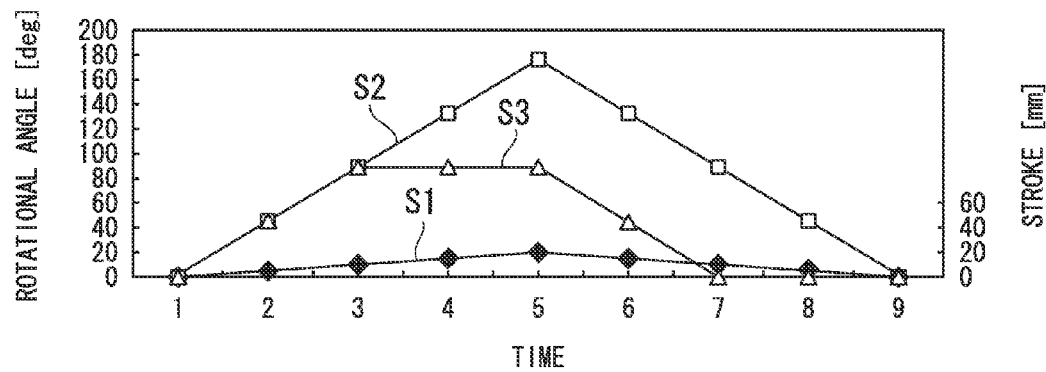
FIG. 72 describes in a graph the action of the pair of forceps members in accordance with a varied strode of a rod.

As described by the line S1 in FIG. 72, the rod 100 is moved from the most extended position to the most retracted position, and then extended again. As described by the line S2, the forceps member 115 is moved continuously in conjunction with the rod 100. As described by the line S3, the forceps member 131 does not rotate by rotational angles of 90° or greater.

Figure 73:
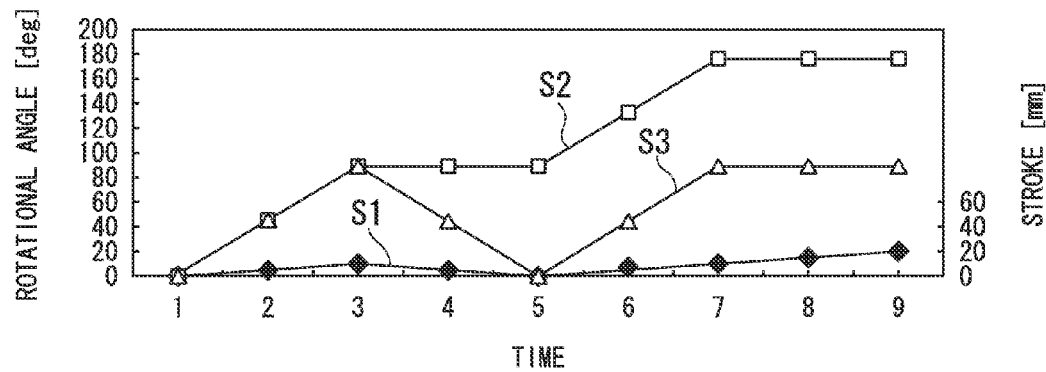
FIG. 73 describes in a graph the action of the pair of forceps members in accordance with a varied strode of the rod.

As shown in FIG. 73, the rod 100 is extended after the rod 100 is retracted from the most extended position and the pair of forceps members 115 and 131 closes. When the rod 100 is extended, the forceps member 115 stops and the forceps member 131 opens corresponding to the rod 100. Pulling the rod 100 afterward rotates the pair of forceps members 115 and 131 together in the closing direction, thereby each stopping at 180° and 90°.

Figure 74:
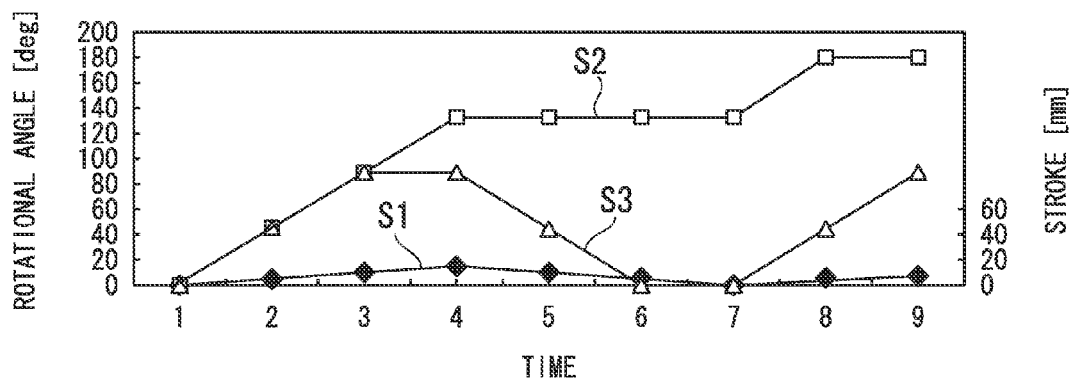
FIG. 74 describes in a graph the action of the pair of forceps members in accordance with a varied strode of the rod.

As shown in FIG. 74, the rod 100 is extended after the rod 100 is retracted from the most extended position and the forceps member 115 rotates beyond 90°, i.e., by 135°. Along with the movement of the rod 100, the forceps member 131 opens and the forceps member 115 stops. Retracting the rod 100 again closes the pair of forceps members 115 and 131.

Figure 75:
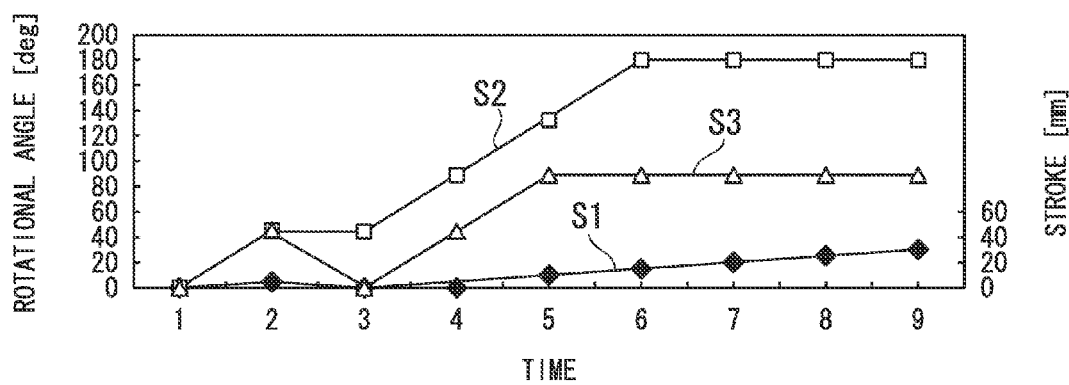
FIG. 75 describes in a graph the action of the pair of forceps members in accordance with a varied strode of the rod.

As shown in FIG. 75, the moving direction of the rod 100 is switched into extending direction before the rod 100 retracted from the most extended position reaches the angle of 90°. Along with the movement of the rod 100, the forceps member 131 opens and the forceps member 115 stops. Retracting the rod 100 again closes the pair of forceps members 115 and 131.

Figure 76:
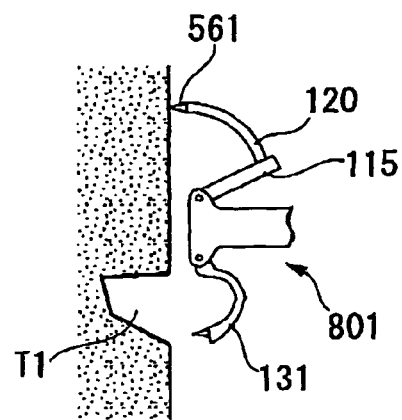
FIG. 76 illustrates the action corresponding to FIG. 72.
Figure 77:
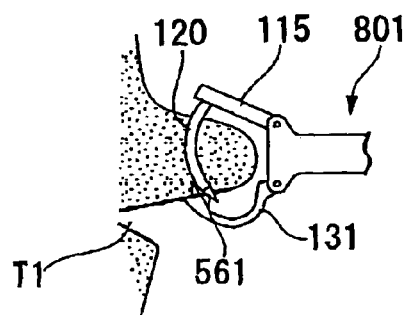
FIG. 77 illustrates the action corresponding to FIG. 72.
Figure 78:
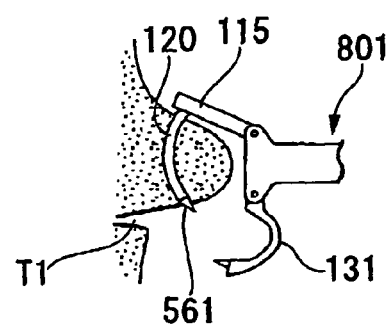
FIG. 78 illustrates the action corresponding to FIG. 72.
Figure 79:
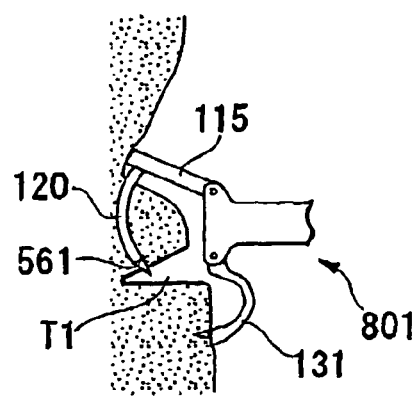
FIG. 79 illustrates the action corresponding to FIG. 72.
Figure 80:
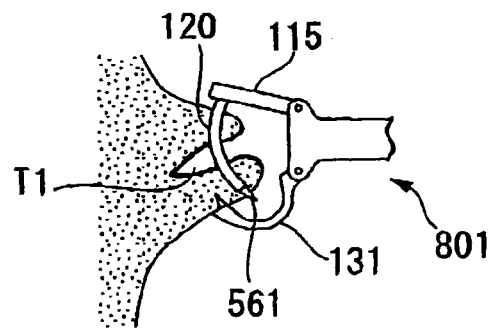
FIG. 80 illustrates the action corresponding to FIG. 72.
Figure 81:
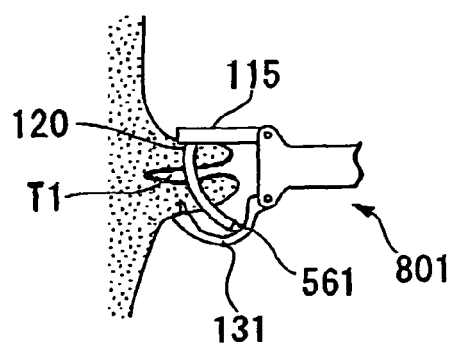
FIG. 81 illustrates the action corresponding to FIG. 72.

The operation corresponding to FIG. 73 describing the examples for the above operations will be more specifically shown in FIGS. As shown in FIG. 76, the curved needle 120 attached to one of the forceps members 115 begin to be inserted into the tissue directed to one side of an injury section T1. As illustrated in FIG. 77, one side of the tissue of an injury section T1 is retrieved and gripped by the pair of forceps members 115 and 131, and the curved needle 120 is inserted into the tissue. Moving this state of the rod 100 toward the distal end disengages the rod 100 from the link for rotating the forceps member 115, thereby opening only the forceps member 131. As illustrated in FIG. 78, although the forceps member 131 opens, the curved needle 120 remains being inserted through the tissue. Moving the suture instrument 801 as illustrated in FIG. 79 allows the forceps member 131 to bite the tissue opposite the injury section T1. Moving the rod 100 toward the proximal end closes the forceps member 131 while the forceps member 115 directed to the curved needle 120 remains stopped. As illustrated in FIG. 80, the curved needle 120 is penetrated into the tissue retrieved by the forceps member 131. The rod 100 further extending as illustrated in FIG. 81 is connected to a link of the forceps member 115; thus, the pair of forceps members 115 and 131 closes.

In the cases described in FIGS. 73 and 75, the forceps member 131 having the smaller rotational range can be rotated while the forceps member 115 having the greater rotational range is stopped at the rotated angle of 90°. This is effective for reinserting the curved needle 120. When the rod 100 is moved so as to open the pair of forceps members 115 and 131 as described with respect to timings 3 to 5 of FIG. 73 and timings 4 to 7 of FIG. 75, the forceps member 115 having the greater rotational range is stopped until the forceps member 131 having the smaller rotational range is fully opened.

In the cases described in FIGS. 73 and 75, the forceps member 131 having the smaller rotational range can be opened while the forceps member 115 having the greater rotational range is stopped at the rotated angle of 90°. Since the forceps member 131 grips the tissue with a force urged by the charging spring 577, the forceps member 115 may open prior to opening the forceps member 131 when the pair of forceps members 115 and 131 is opened; thus, the curved needle 120 may be removed. In such a case, the forceps member 131 can be opened while the forceps member 115 is penetrated in the tissue. Enabling the pair of forceps members 115 and 131 to operate independently by means of the rod 100 allows the forceps member 115 to once penetrate the tissue to open only by the forceps member 131 in the penetrated state, thereby allowing the pair of forceps members 115 and 131 to regrip and re-penetrate the previous tissue and another tissue. This configuration also allows the needle to be intentionally moved to a desired position.

Seventh Embodiment

Figure 82:
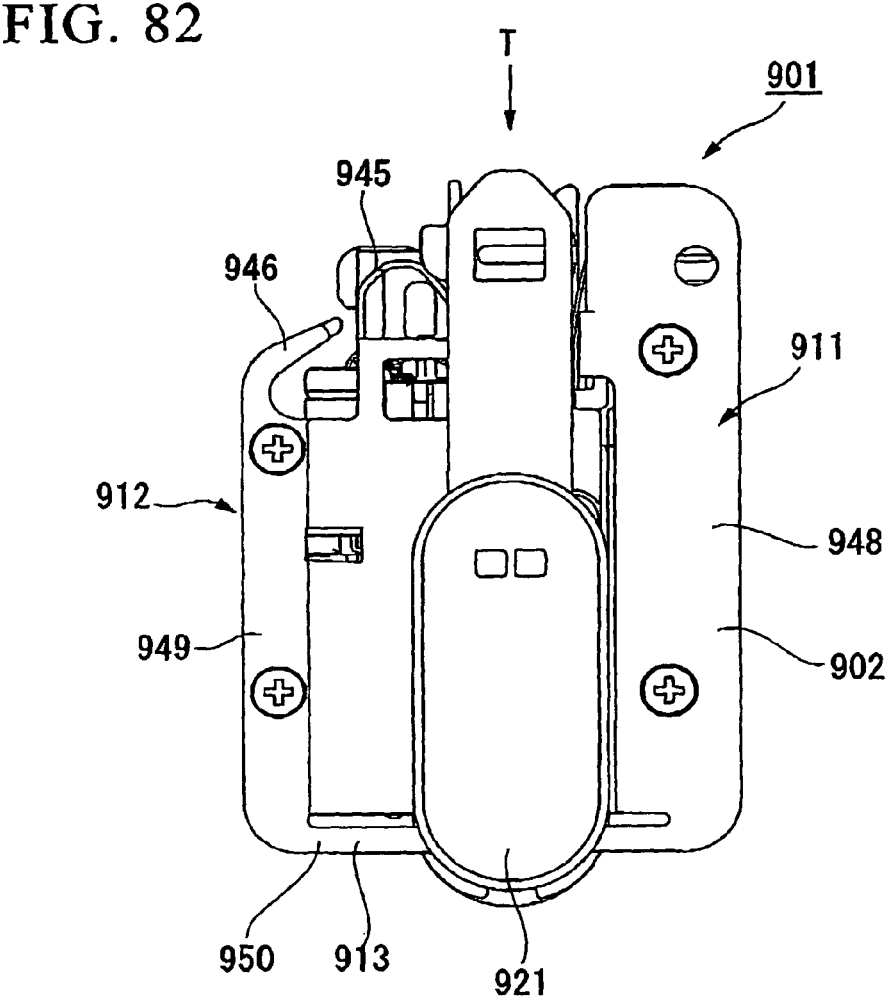
FIG. 82 is a view showing the outlook of an applicator.
Figure 83:
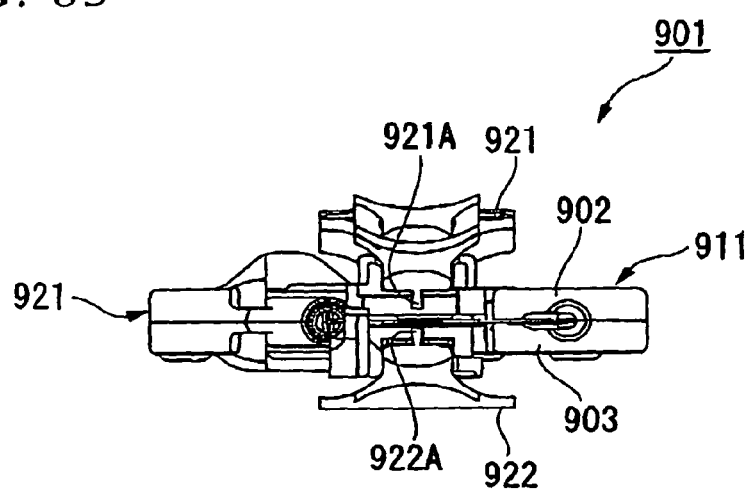
FIG. 83 is a view on arrow T in FIG. 82.

Provided in a attaching device 901 illustrated in FIGS. 82 and 83 are two base plates 902 and 903 that are pasted, and a cartridge 153 accommodated therebetween. The attaching device 901 has an elongated thread holding section 911 and a casing holding portion 912 so that the thread holding section 911 is connected to the casing holding portion 912 via an arm 913. A suture instrument is attached to the attaching device 901 in use in the direction indicated by an arrow shown in FIG. 82.

A pair of locking members 921 and 922 freely opening and closing is attached to the casing holding portion 912. Protrusions 921A and 922 A are formed on ends of the locking members 921 and 922. The protrusions 921A and 922A are inserted into the guide hole 80C on the tip cover 80 of the suture instrument. In a case where the guide hole 80C is formed on only one side, the protrusion is formed on only one of the locking members 921 and 922 correspondingly.

Figure 84:
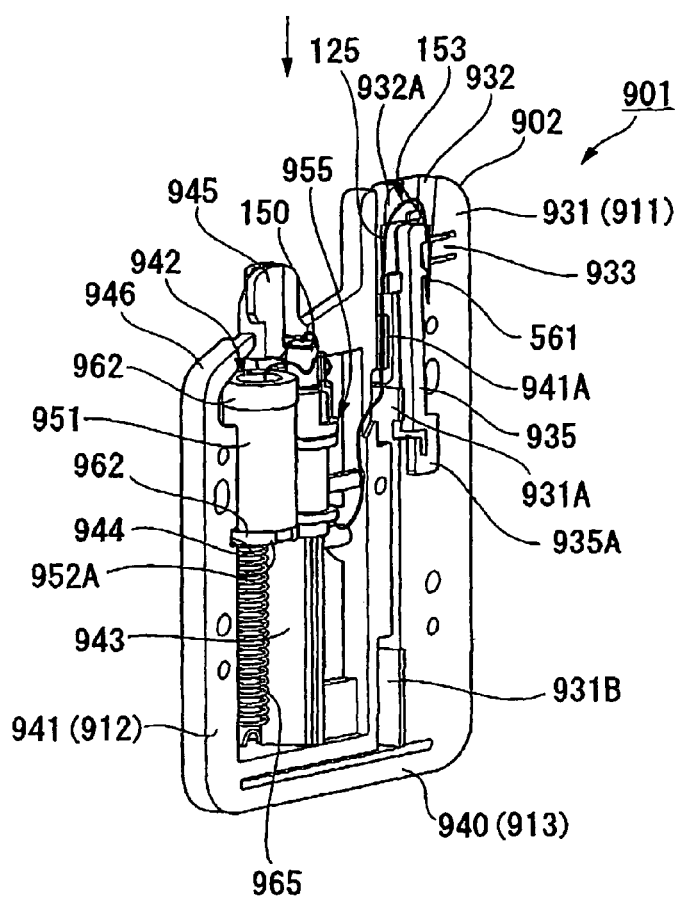
FIG. 84 illustrates an attaching portion with a base plate removed therefrom.
Figure 85:
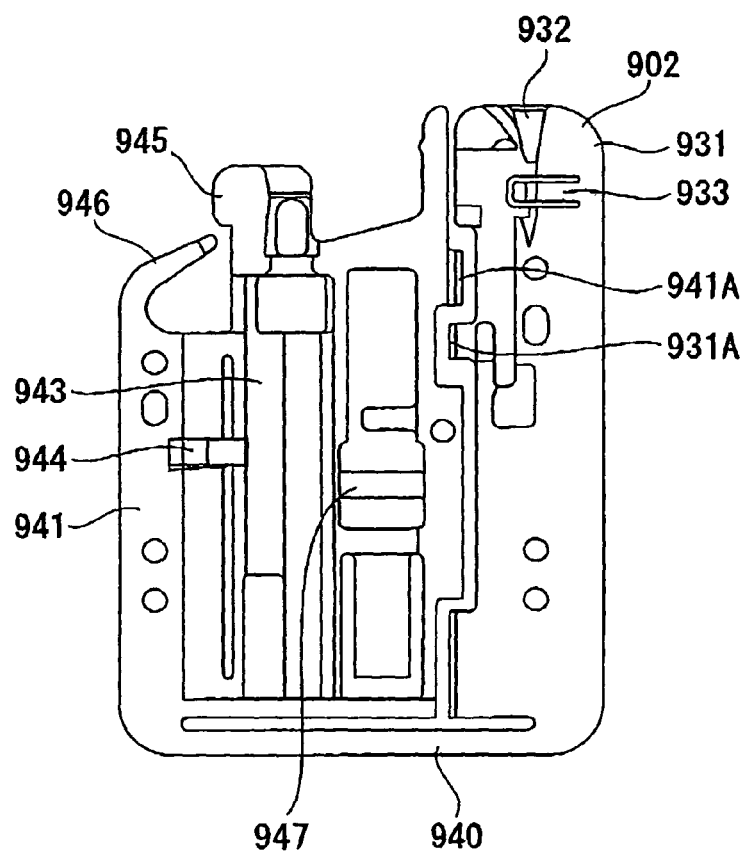
FIG. 85 is a plan view of the base plate.

As illustrated in FIGS. 84 and 85, the plate 931 forming the thread holding section 911 is expanded approximately along the direction of the insertion of the suture instrument indicated in the drawings. Disposed to project from the end portion is a enclosure section 932 capable of receiving the curved needle 120. In order to facilitate the reception of the curved needle 120, the opening width of the enclosure section 932 increases gradually. A detachable needle 561 is accommodated in the back of the enclosure section 932. Formed in the enclosure section 932 is a cut 932A for drawing the suture thread 125. A stay 933 for elastically supporting the detachable needle 561 is disposed on the plate 931 orthogonally to the detachable needle 561. The detachable needle 561 is further supported by a thread holder 935 attached to the plate 931. The thread holder 935 capable of accepting the curved needle 120 and cantilevered by a cantilever section 935A supports the curved needle 120 with the detachable needle 561 aligned.

The plate 940 for integrally forming the arm 913 extends in the direction orthogonal to the plate 931 at the end portion of the plate 931. Connected integrally to the end portion of the plate 940 is a plate 941 for forming the casing holding portion 912.

A sliding groove 943 is formed on the plate 941 in the direction of the arrow. Disposed in the sliding groove 943 is a holder 942 for accommodating the casing 150. An engagement groove 944 is disposed in the middle of the sliding groove 943 so as to project thereon in the direction approximately orthogonal to the longitudinal direction of the sliding groove 943. Extended from the plate 941 are a guide piece 945A for guiding the suture instrument 1 and an arm 946 for elastically pressing the forceps member 131. A freely rotative locking member 922 is supported by a shaft 947 disposed in the approximate center. Guide pieces 931A, 931B, and 941B are disposed upright in the end portions of the plates 931 and 941 that extend in parallel.

The base plate 902 has a plate 948 constituting the thread holding section 911, a plate 949 constituting the casing holding portion 912, and a plate 950 constituting the arm 913. The configuration of the inner surface of the base plate 902 is approximately the same as that of the base plate 903. However, the stay 933 is not disposed on the base plate 902. Also, a groove slidably accepting the guide pieces 931A and 931B is disposed on the base plate 903, and a groove slidably accepting the guide piece 941A is formed on the plate 948.

Figure 86:
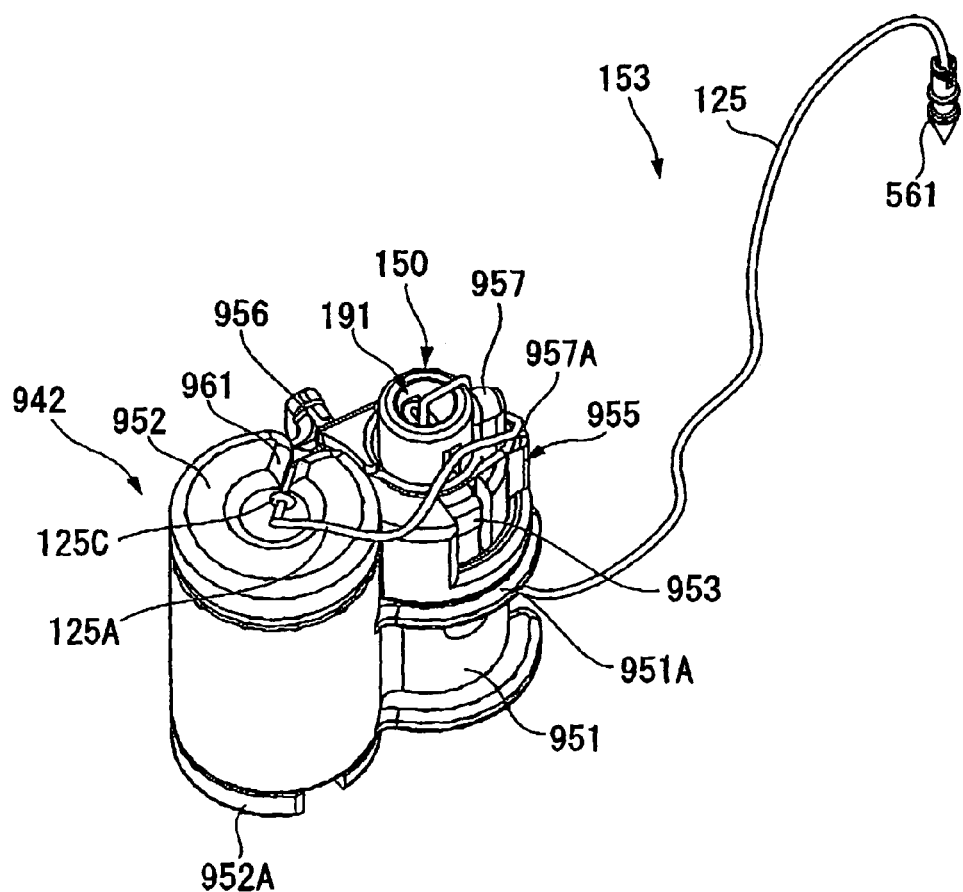
FIG. 86 is a perspective view showing the holder and the cartridge attached thereto.

As illustrated in FIG. 86, a cylinder 952 of the holder 942 is rotatably inserted into a main body section 951 capable of accommodating the casing 150.

The casing 150 is inserted into the main body section 951 of the holder 942. The casing 150 of the main body section 951 is locked by a pair of elastically deformable arms 953, and a part of the proximal end of the casing 150 is exposed to the outside of the holder 942. Provided around the outer periphery of the main body section 951 is a flange-like projecting section 951A to which the bumped projecting section 951A is attached.

Figure 87:
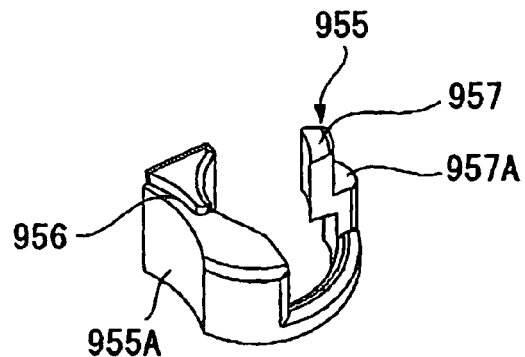
FIG. 87 is a perspective view showing a thread holder.

As illustrated in FIGS. 86 and 87, an arched part of the thread holder 955 having an approximate C-letter cross section is depressed corresponding to the cylinder 952. Formed from the arched curved surface 955*a* to the inner circumference surface is a groove 956 through which the suture thread 125 is passed. Also, a guide section 957 extending approximately along the casing 150 is disposed opposite to the curved surface 955*a* with respect to a central axis. The suture thread 125 is wound on a shoulder section 957A at an outer periphery of the guide section 957.

Figure 88:
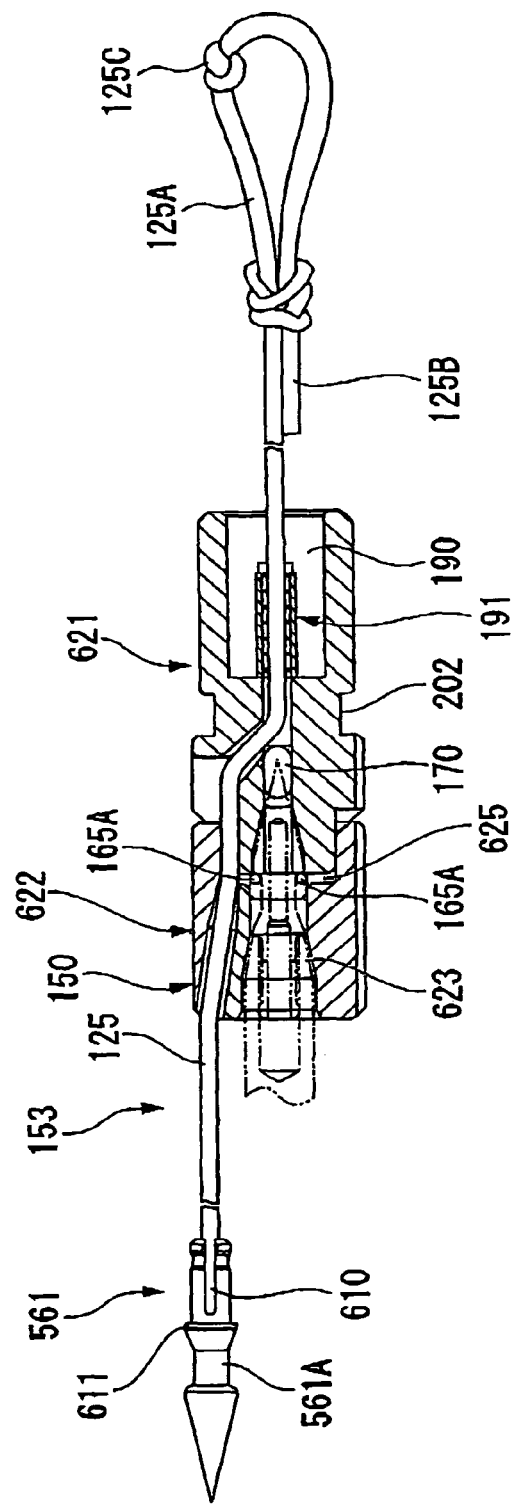
FIG. 88 is a cross sectional view showing the cartridge.
Figure 89:
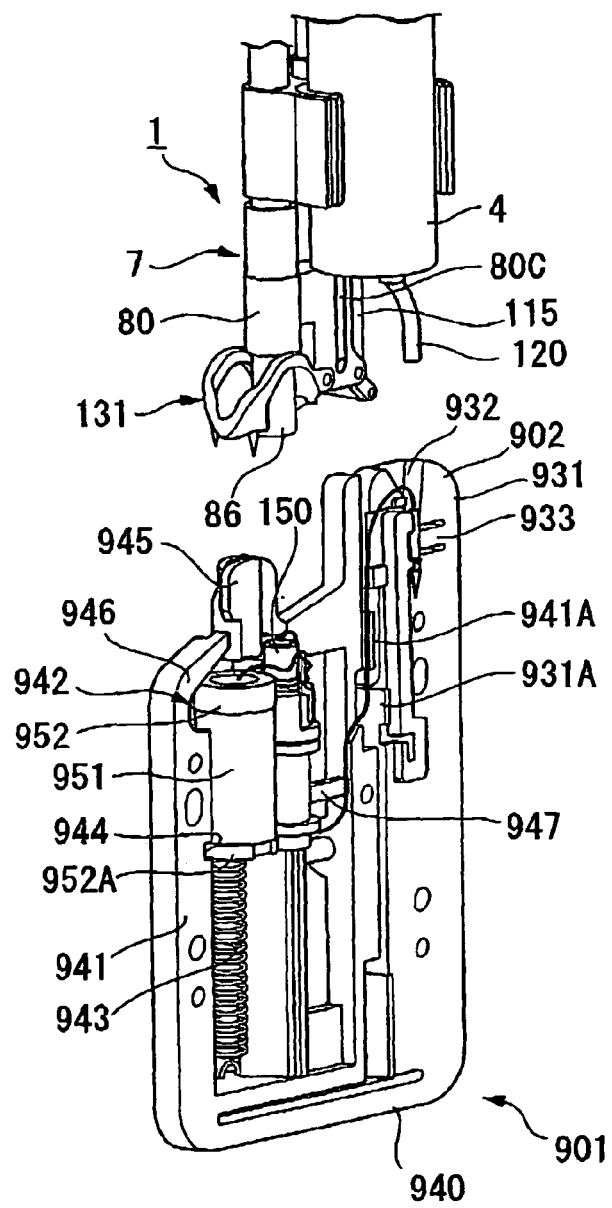
FIG. 89 illustrates an action for attaching the cartridge to the suture instrument.

As illustrated in FIGS. 86 and 88, the suture thread 125 drawn from the casing 150 is wound once on the outer periphery of the casing 150. The loop 125A having been wound around the shoulder section 957A of the guide section 957 of the thread holder 955 is passed through the groove 956 and wound around the cylinder 952. Formed halfway of the loop 125A is a knot 125C hooked on the cylinder 952.

A groove 961 is formed toward the center of the cylinder 952. Although the groove 961 permits one suture thread 125 to pass through, the width of the groove 961 does not allow the knot 125C to pass therethrough. The axially rotative cylinder 952 is urged by a torsion coil spring, not shown in the drawing, accommodated in the main body section 951. As illustrated in FIG. 86, a part of the cylinder 952 projects from an end portion of the main body section 951, and a stopper 962 bulging radially outward is disposed to the projecting portion 952A. The stopper 962 is inserted into a engagement groove 944 directed to a base plate 902.

The holder 942 is smaller in length than the sliding groove 943 of the base plate 902. Disposed across the end portion directed to the arm 913 and the holder 942 is a coiled spring 965, and the holder 942 is continuously urged toward the plate 940. However, the holder 942 cannot be pulled toward the plate 940 since the initial state of the through-hole 33 is locked by the engagement groove 944.

As illustrated in FIGS. 10, 38, 88, and 89, when the cartridge 153 is attached, the hook sheath 21 is extended while the open state of the pair of forceps members 115 and 131, a tip claw section 211 in the cartridge supporting member 86 is projected at the distal end.

Figure 90:
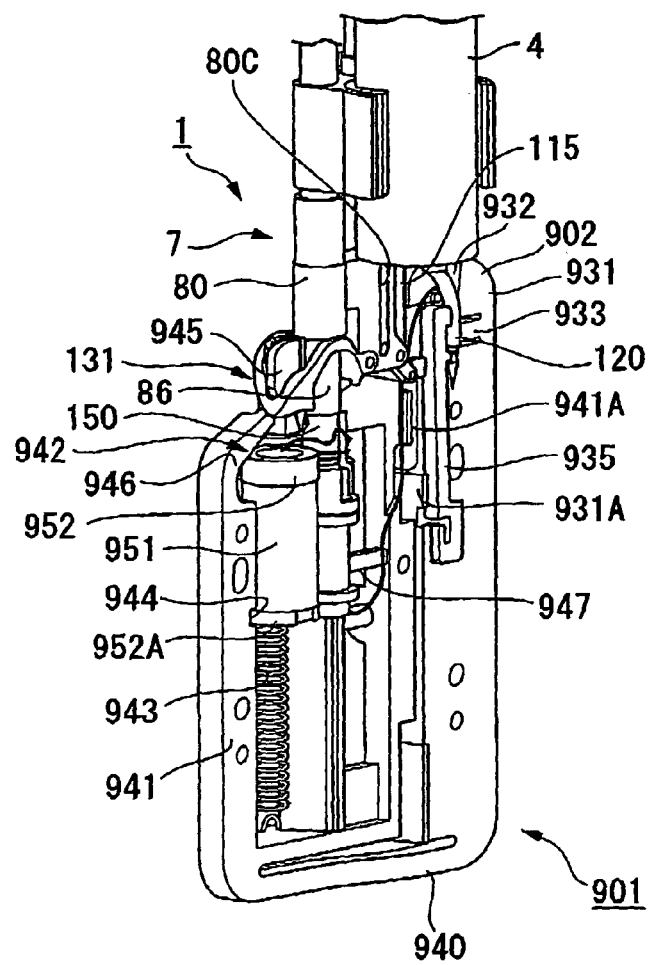
FIG. 90 illustrates the suture instrument engaging the attaching device.
Figure 91:
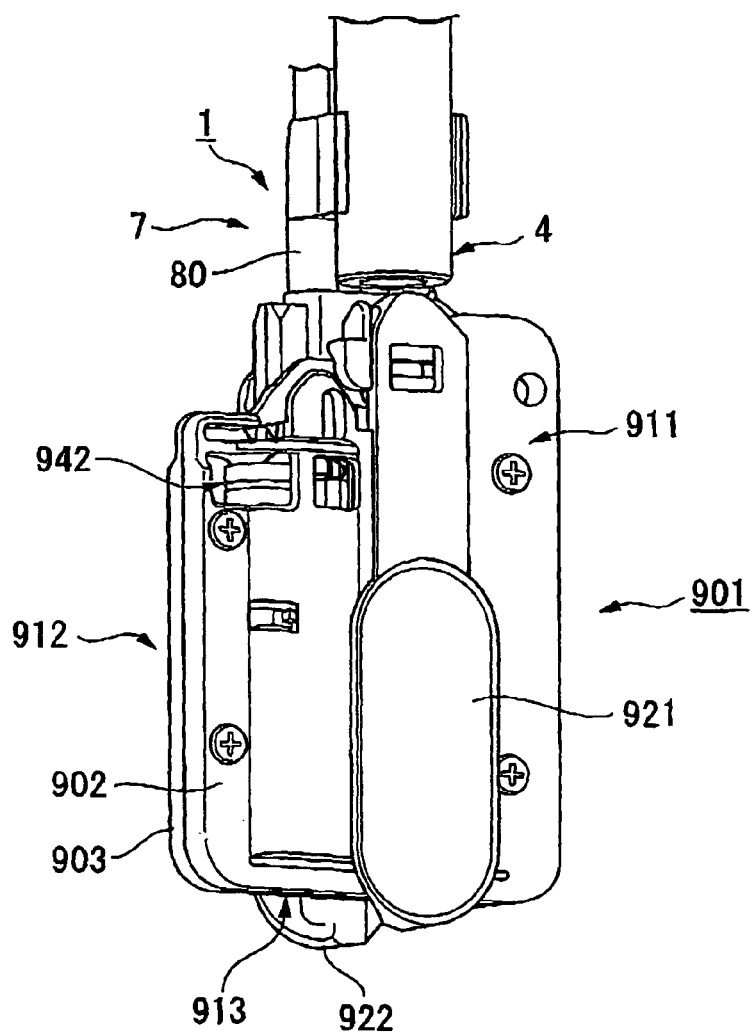
FIG. 91 illustrates the suture instrument engaging the attaching device.

As illustrated in FIGS. 90 and 91, pushing the treatment section 7 to the attaching device 901 allows the protrusions 921A and 922A of the locking members 921 and 922 to fit in the guide hole 80C of the tip cover 80 of the suture instrument 1.

In this state, the curved needle 120 of the forceps member 115 enters the enclosure section 932 of the thread holding section 911. The curved needle 120 following the taper of the enclosure section 932 is guided to the detachable needle 561 even if there is a positional deviation between the curved needle 120 and the enclosure section 932 since the enclosure section 932 is a circular truncated cone in a shape where the diameter of the opening decreases more significantly inward of the opening. The curved needle 120 begins to fit in the detachable needle 561 aligned by the thread holder 935 while wedging the thread holder 935 aside. The thread holder 935 wedged aside by the curved needle 120 moves beyond the stay 933 at a supporting point of the cantilever section 935A over the stay 933 and evacuates from the moving path of the curved needle 120. In this state, the distal end of the stay 933 making contact with the thread holder 935 retains the thread holder 935 so that the thread holder 935 does not return to the detachable needle 561.

Since the detachable needle 561 is supported in the vicinity of the opening of the enclosure section 932, the curved needle 120 is fit into there while pushing the detachable needle 561. Although the thread holding section 911 is freely movable relative to the casing holding portion 912 due to the elastic deformation of the arm 913, since the guide pieces 931A, 931B, and 941A are slidable only along the groove in the vicinity of the base plate 902, the moving direction of the thread holding section 911 is regulated in the insertion direction of the suture instrument 1. Therefore, the axial line of the distal end of the curved needle 120 does not deviate from the axial line of the detachable needle 561; thus, reliable placement can be obtained.

On the other hand, the forceps member 131 makes contact with the arm 946 of the casing holding portion 912. The forceps member 131 is urged into the opening direction by the arm 946. This enforces the pair of forceps members 115 and 131 to open in state suitable for attaching the cartridge 153 even if the forceps member 131 has a clearance or a manufacture error.

Figure 92:
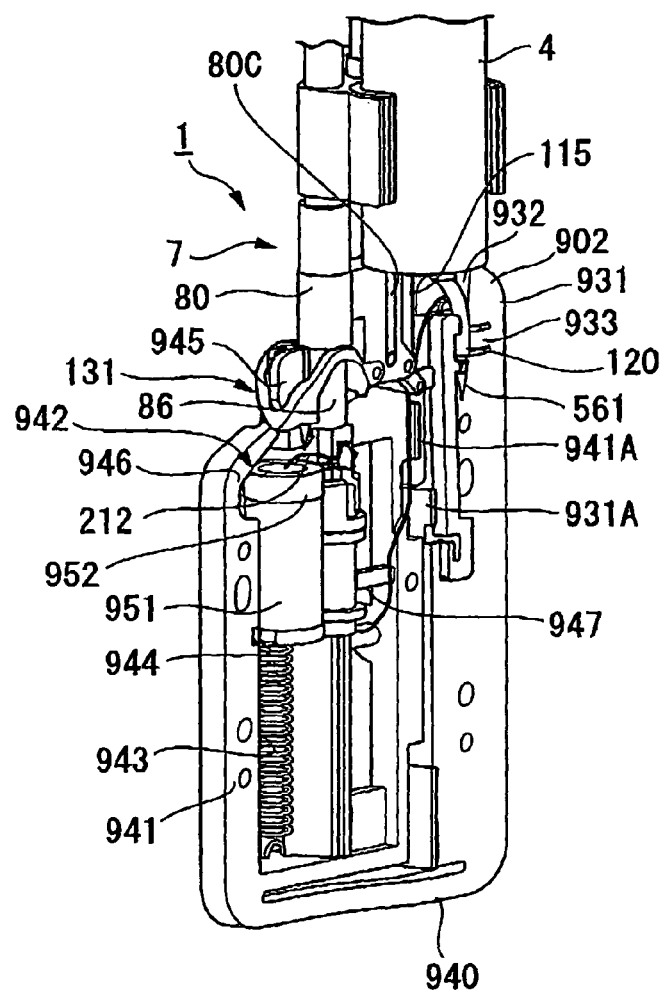
FIG. 92 illustrate the casing forced with the hook.

As illustrated in FIG. 92, extending the hook 212 thrusts the casing 150 into the holder 942. Since the fully thrusted casing 150 provides an excess of the loop 125A of the suture thread 125 wound around the outer periphery of the casing 150, the cylinder 952 is rotated by means of the torsion coil spring around the main body section 951. Winding the loop 125A around the cylinder 952 pulls the suture thread 125, thereby winding around the hook 212.

Figure 93:
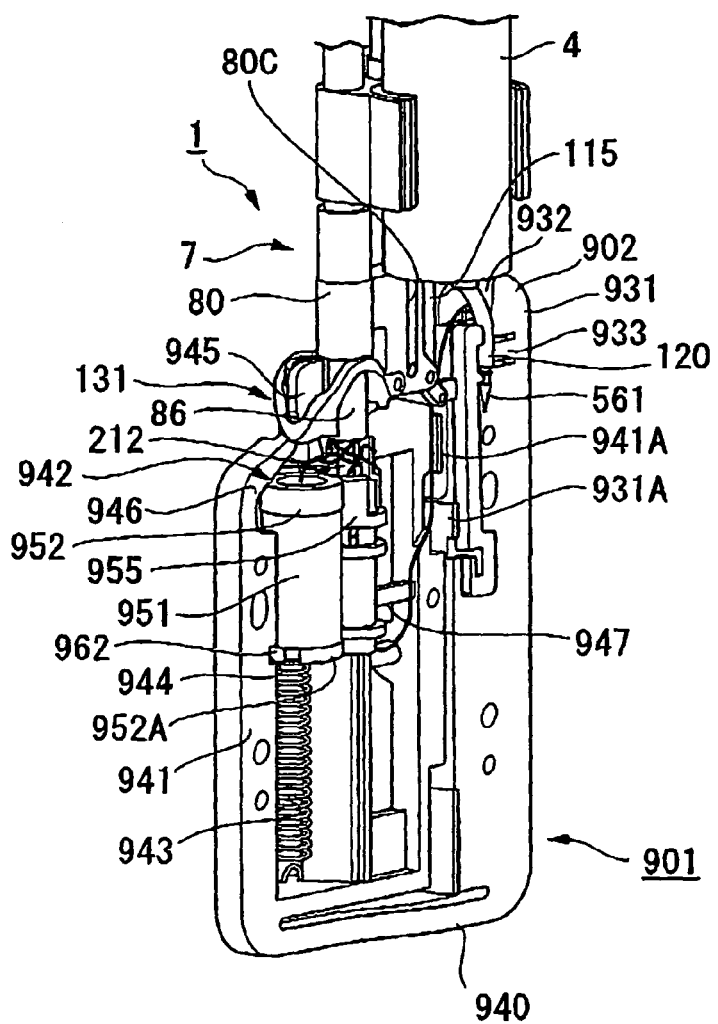
FIG. 93 illustrates the thread holder pulled with the suture thread by returning the hook.

Drawing back the hook 212 attracts the thread holder 955 to the suture instrument 1 because the suture thread 125 is hooked on the groove 961. A stopper 962 of the holder 942 is hooked on the engagement groove 944 and urged oppositely by the coiled spring 965. Therefore, as illustrated in FIG. 93, only the thread holder 955 moves. The suture thread 125 drawn by the thread holder 955 is removed from the cylinder 952.

Figure 94:
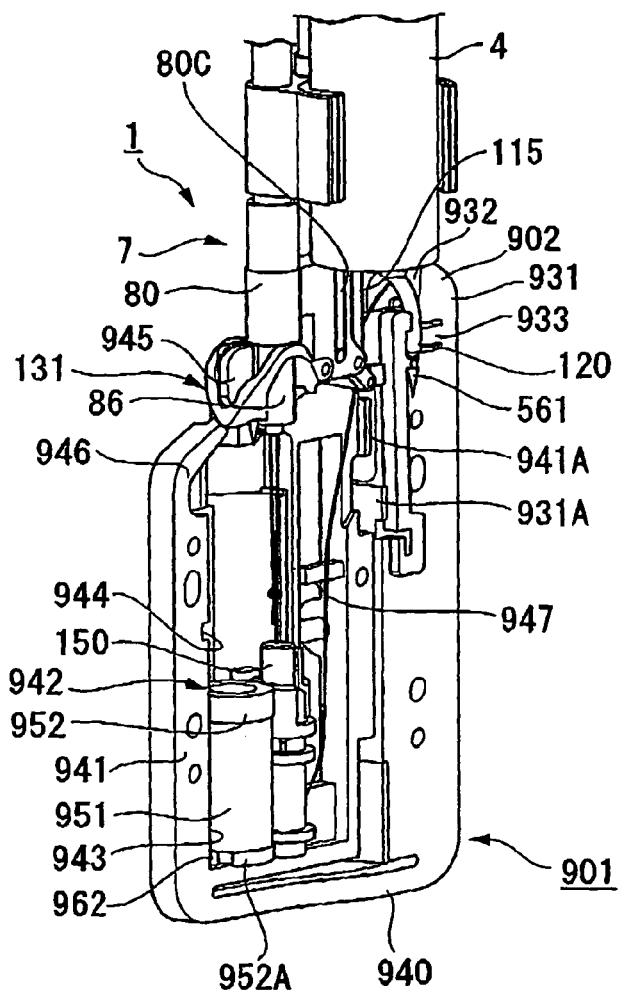
FIG. 94 illustrates the withdrawn state of a holder pulled by coiled spring.
Figure 95:
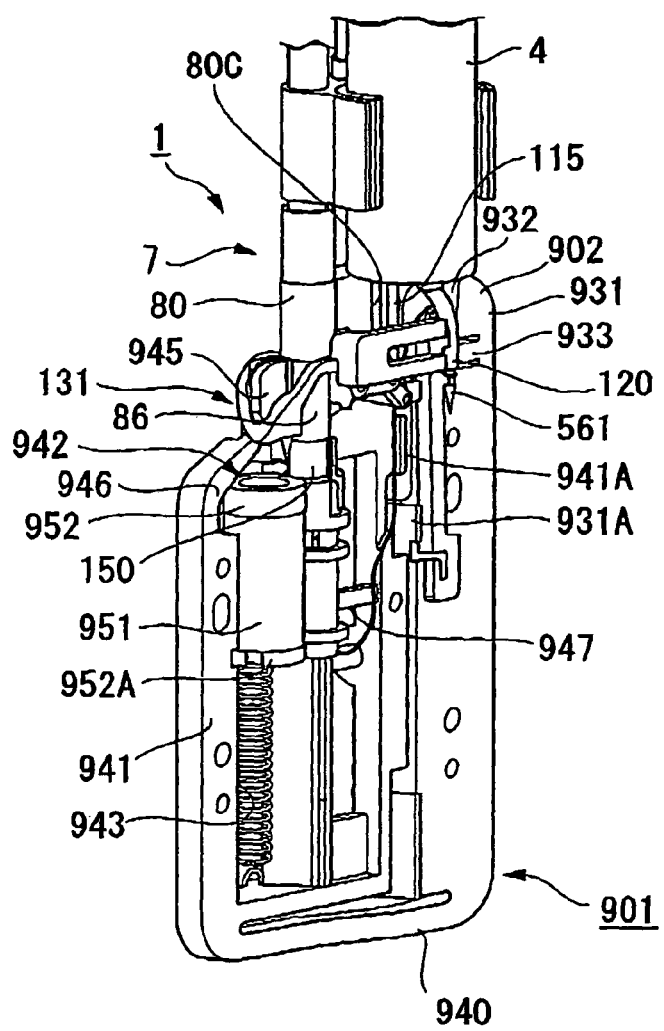
FIG. 95 illustrates the withdrawn state of the holder pulled by the hook via the suture thread.
Figure 96:
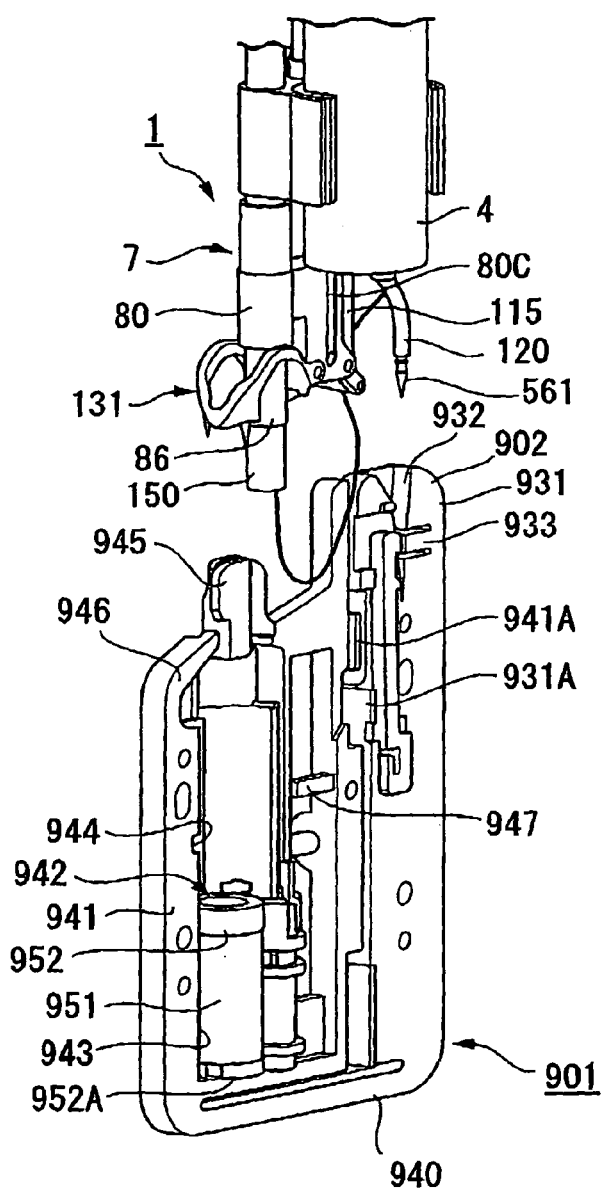
FIG. 96 illustrates the casing removed from the holder.

Disengagement of the suture thread 125 rotates the cylinder 952 further, and the stopper 962 disposed from the main body section 951 to the projecting section 952A is removed from the engagement groove 944. As illustrated in FIG. 94, a coiled spring 965 is contracted, and the holder 942 moves along the sliding groove 943. Since the hook 212 is unmovable, tension is provided to the suture thread 125 wound around the hook 212. As illustrated in FIG. 95, drawing back the hook 212 attracts the thread holder 942 via the suture thread 125. Force drawing the hook 212 and drawing force of the coiled spring 965 act on the arm 953 (see FIG. 86) of the holder 942. Drawing the hook 212 by a predetermined length attracts the casing 150 into the cartridge supporting member 86, thereby moving the holder 942 together with the casing 150 toward the suture instrument 1. Since this position has a space for evacuation of the arm 953, the arm 953 is disengaged from the casing 150 separating from the holder 942 and accommodated in the cartridge supporting member 86. Placement of the cartridge 153 is completed by opening the locking members 921 and 922 to retract the suture instrument 1 as illustrated in FIG. 96 separate from the attaching device 901.

The attaching device 901 in use in the present embodiment facilitates the placement of the cartridge 153. Also, the attaching device 901 can draw back the tensioned suture thread 125 wound around the hook 212 into the suture instrument 1 since the holder 942 is drawn back by the force urged by the coiled spring 965 after winding the suture thread 125 around the hook 212. The reliable placement of the cartridge 153 can be therefore obtained since the suture thread 125 will not be disengaged from the hook 212. In addition, the attaching device 901 can be used in the suture instrument 501.

Eighth Embodiment

Figure 97:
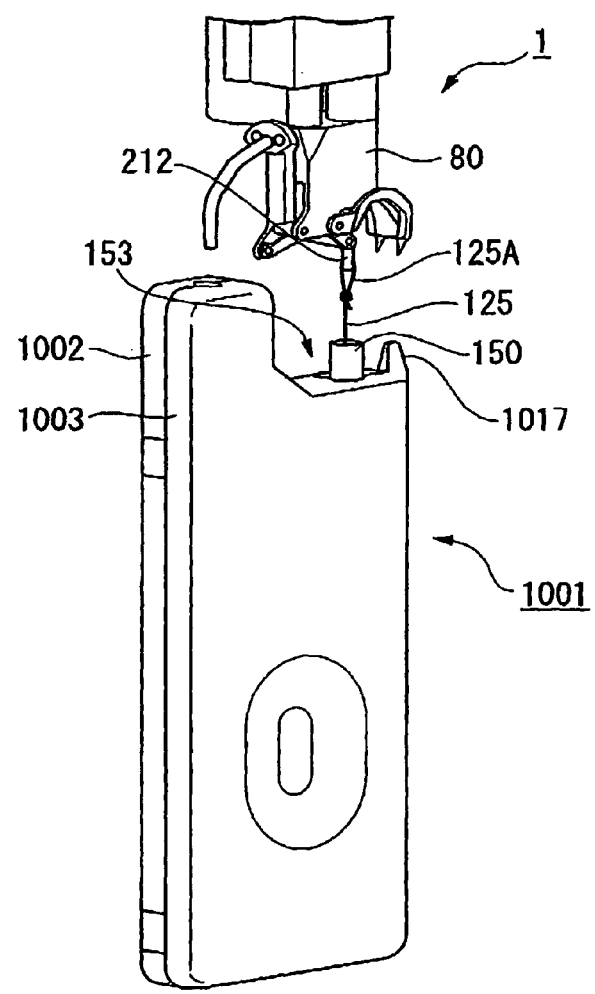
FIG. 97 illustrates another embodiment of the air supply device.
Figure 98:
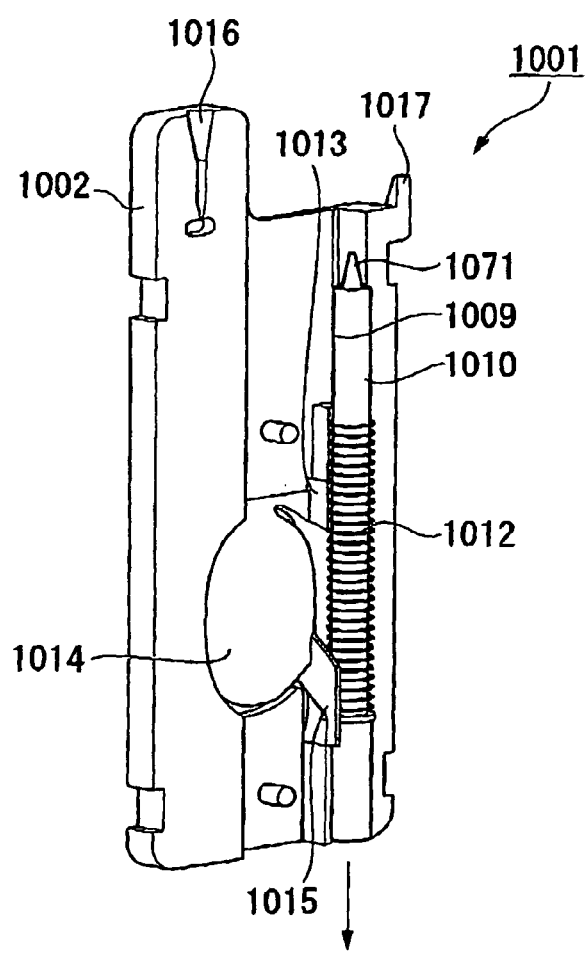
FIG. 98 illustrates an attaching device with a base plate removed therefrom.

Provided in an attaching device 1001 illustrated in FIG. 97 are two base plates 1002 and 1003 that are pasted, and a cartridge 153 accommodated therebetween. As illustrated in FIG. 98, formed in the attaching device 1001 is a groove 1009 in which a freely extending and retractable rod 1010 is accommodated in the longitudinal direction. A locking member 1071 is fixed on the distal end of the rod 1010, and the locking member 1071 is inserted into the casing 150 to be fixed thereon. A rubber shaft allowing the casing 150 to be moderately press-fit renders the locking member 1071 easy-to-remove. A coiled spring 1012 is wound around the outer periphery of the rod 1010. One end of the coiled spring 1012 is locked to an end of the groove 1009. The other end of the coiled spring 1012 is fixed to the rod 1010. The rod 1010 is locked by a protrusion 1015 at a position where the coiled spring 1012 is pressed by a predetermined length. The rod 1010 is therefore urged in a direction indicated by an arrow shown in FIG. 98 in accordance with the pressure provided to the coiled spring 1012. The protrusion 1015 is disposed to project from a button 1014 integrally formed with the base plate 1002. The button 1014 can be pressed in a direction orthogonal to the surface of the base plate 1002, and if the button 1014 is pressed, the protrusion 1015 moves in the same direction.

A receiving portion 1016 is further provided to the base plate 1002. The width of the opening end of the receiving portion 1016 is enlarged so as to be able to align and support the detachable needle 561 and accommodate the curved needle 120. An arm 1017 is disposed to project from the edge section of the base plate 1002 opposite the receiving portion 1016.

In addition, the base plate 1003 has approximately the same configuration as that of the base plate 1002 except that the base plate 1003 does not have the protrusion 1013 and the button 1014.

Figure 99:
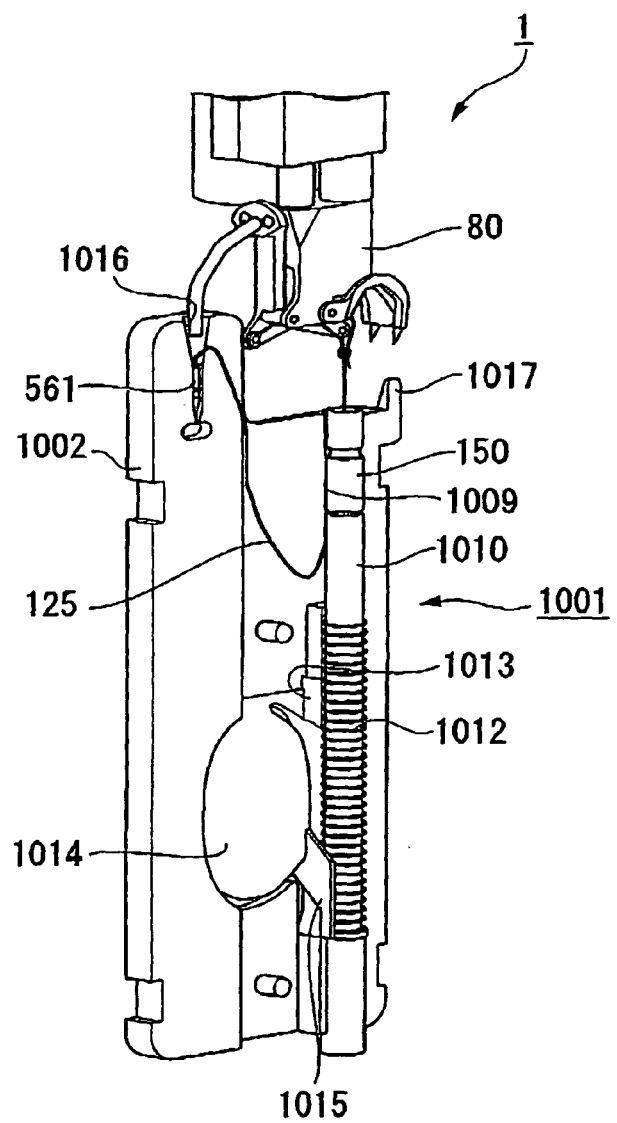
FIG. 99 illustrates procedures for attaching the cartridge having the suture thread hooked on the hook.

As illustrated in FIG. 99, fitting the casing 150 of the cartridge 153 to the locking member 1071 allows the rod 1010 to support the casing 150. The detachable needle 561 is attached to the receiving portion 1016. The suture thread 125 is routed through a space between the base plates 1002 and 1003.

Figure 100:
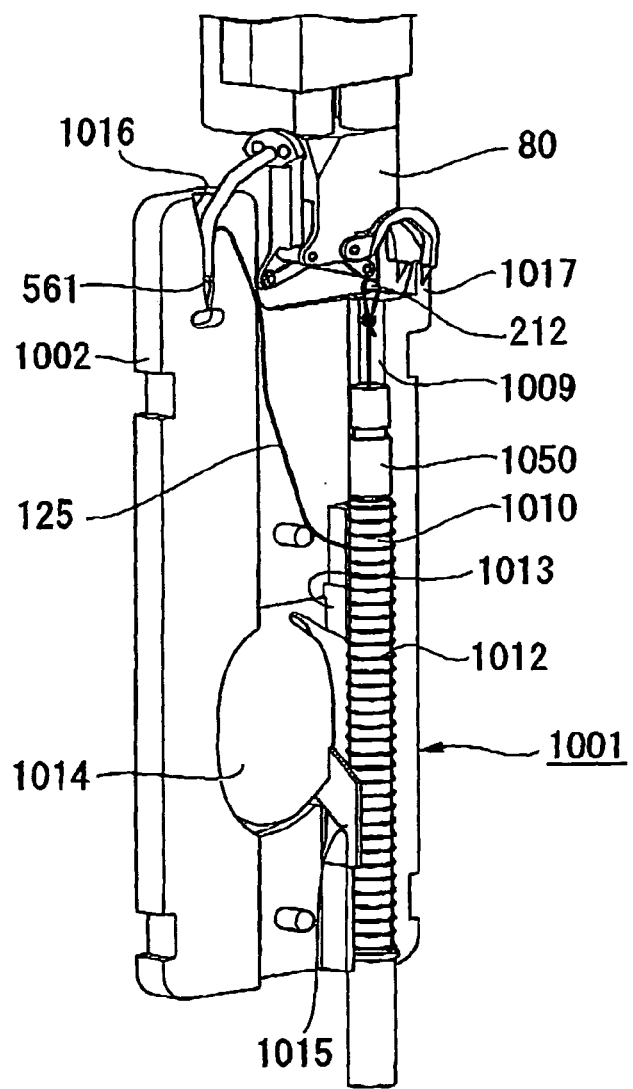
FIG. 100 illustrates the withdrawn state of the rod having the suture thread tensioned by pushing a button.

When the cartridge 153 is attached to the suture instrument 1, a loop 125A is hooked on a hook 212, and then a button 1014 is pressed. As illustrated in FIG. 100, the protrusion 1015 is disengaged from the rod 1010, and the rod 1010 moves in a direction separating from the suture instrument 1. The withdrawn state of the suture thread 125 provides tension between the hook 212 and the loop 125A. The force exerted by the coiled spring 1012 does not disengage the loop 125A from the hook 212. The curved needle 120 entering the receiving portion 1016 fits the detachable needle 561. The forceps member 131 making contact with the pressing arm 1017 allows the pair of forceps members 115 and 131 to fully open.

Figure 101:
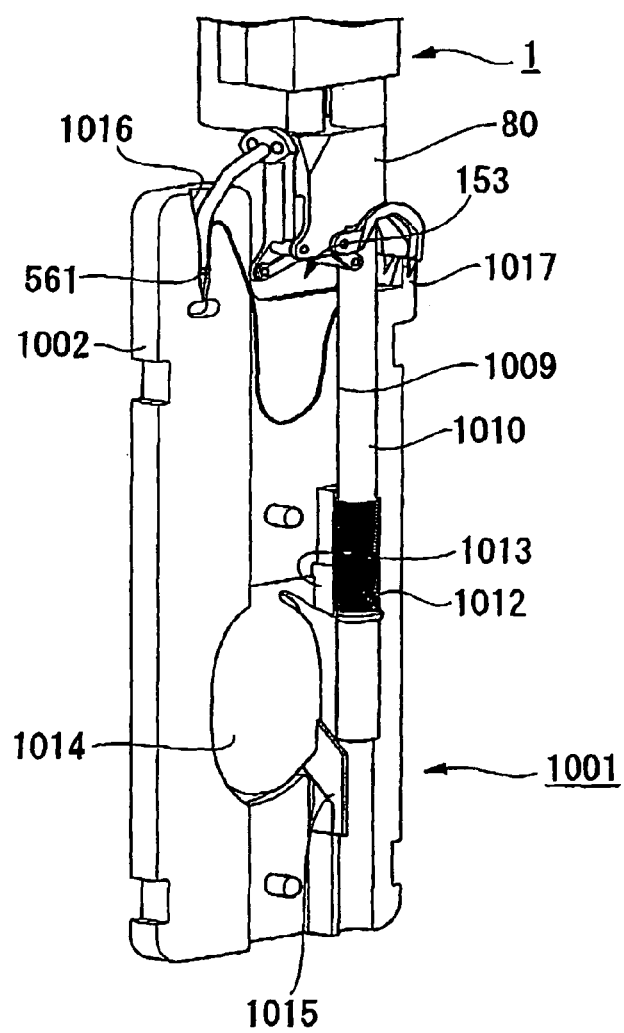
FIG. 101 illustrates the withdrawn state of the rod pulled by the hook via the suture thread.

Depressing the hook 212 attracts the rod 1010 via the suture thread 125 and the casing 150. As illustrated in FIG. 101, pressing the coiled spring 1012 projects the rod 1010, thereby withdrawing the casing 150 into the casing holding portion in the tip cover 80. Afterward, separating the suture instrument 1 disengages the casing 150 from the locking member 1011, thereby passing the cartridge 153 to the suture instrument 1.

Figure 102:
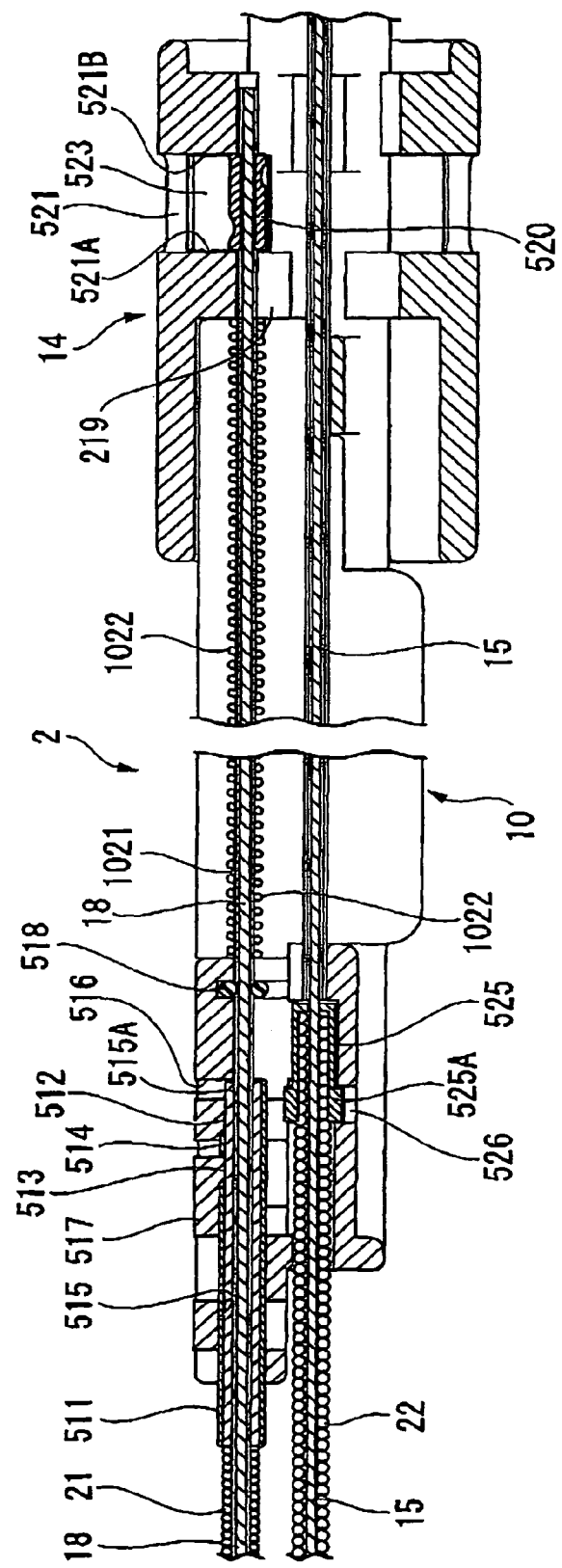
FIG. 102 illustrates an example of a control portion.

The use of the flexible member, e.g., a spring that spontaneously retracts the hook 212 eliminates the need for withdrawing the finger-hook ring 17 in the vicinity of the proximal end of the control portion 2. As illustrated in FIG. 102, the spring 1022 is disposed on an outer periphery of the reinforcement pipe 1021 covering the hook operating wire 18 with the control portion 2, and the hook operating portion 14 is urged in a direction toward the proximal end. The configuration of control portion 2 facilitates operation in the case where the cartridge 153 is attached without using the attaching device 1001 described in the embodiments.

In the present embodiment, since tension utilizing the force exerted by the coiled spring 1012 is provided to the loop 125A first hooked on the hook 212, the cartridge 153 can be reliably attached to the suture instrument 1 without disengaging the loop 125A from the hook 212. Operation with a rubber grove is still easy since the tension can be provided by button operation.

Figure 103:
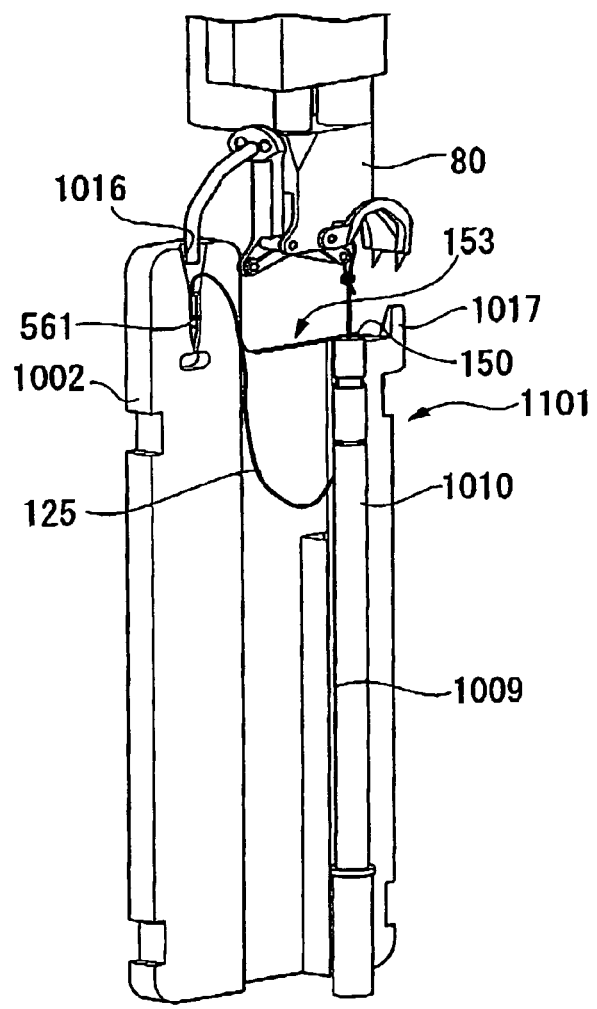
FIG. 103 is a view showing a modified example of the attaching device.

FIG. 103 illustrates a modified example. The freely extending and retractable rod 1010 is disposed in the attaching device 1101. When the cartridge 153 is attached to the suture instrument 1, a loop 125A is hooked on a hook 212, and then a button 212 is brought back. The sliding resistance of the rod 1010 provides tension to the suture thread 125. The attaching device 1101 having a simple configuration allows the cartridge 153 to be attached to the suture instrument 1.

Although the preferred embodiments have been described as above, the present invention is not limited to these. For example, the present invention can be applied to a rigid endoscope having a rigid insertion portion although a description has been given of a use for the flexible endoscope having the flexible insertion portion in the above embodiments. An arbitrary combination of the components described in each embodiment is also effective in use. Also, methods that can be used for attaching the previously described components are laser-welding, brazing, soldering, adhesion, press-fitting, crimping, and any combination of these methods. Also a two-component part may be manufactured integrally by methods, e.g., pressure-welding or molding. The configuration of the present invention allows for addition, omission, substitution and further replacement without departing from the spirit and scope of the present invention. The present invention is not limited to the above descriptions but is limited only by the appended claims.

What is claimed is:

1. An endoscopic treatment instrument comprising:
   an insertion portion comprising a distal end and a proximal end, the distal end being adapted to be inserted into a human body;
   a treatment portion disposed to the distal end; and
   a control portion disposed to the proximal end, wherein the treatment portion comprises:
      an extendable and retractable input member operated by the control portion;
      a first link disconnectably connected to the input member through a first connecting portion;
      a first control plate disposed in the first connecting portion, the input member inserted through the first control plate, and the first control plate being configured to engage the input member by inclination of the first control plate;
      a first forceps member capable of opening and closing according to advancing and retracting motions of the first link;
      a second link disconnectably connected to the input member through a second connecting portion;
      a second control plate disposed in the second connecting portion, the input member inserted through the second control plate, and the second control plate being configured to engage the input member by inclination of the second control plate; and
      a second forceps member capable of opening and closing according to advancing and retracting motions of the second link, and having an opening-and-closing angle which is lower than an opening and closing angle of the first forceps member, wherein
      the second connecting portion makes the connection between the input member and the second link according to an inclination motion of the second control plate until the second forceps member is opened by a predetermined degree of opening.

2. The endoscopic treatment instrument according to claim 1, further comprising:
   an abutment section provided with the treatment instrument and adapted to contact a distal end of the second control plate when the input member is extended, and
   the second connecting portion that has the second control plate having one hole through which the input member is inserted, wherein
   when the second control plate contacts the abutment section, the second control plate stands vertically, and the second connecting portion connects the input member to the second link, by the hole providing engagement between the second control plate and the input member when the second control plate is disposed diagonally with respect to the moving direction of the input member, until the input member is retracted a predetermined length.

3. The endoscopic treatment instrument according to claim 1, further comprising:
   an abutment section provided with the treatment instrument and adapted to contact a distal end of the second control plate when the input member is extended, and
   the second connecting portion that has the second control plate having one hole through which the input member is inserted, wherein
   when a distal end of the second control plate contacts the abutment section, the second control plate stands vertically, and the second connection portion makes the connection between the input member and the second link due to the input member connecting the second link by the hole providing engagement between the second control plate and the input member when the second control plate is disposed diagonally with respect to the moving direction of the input member.

4. An endoscopic treatment instrument comprising:
   an insertion portion comprising a distal end and a proximal end, the distal end being adapted to be inserted into a human body;
   a treatment portion disposed to the distal end; and
   a control portion disposed to the proximal end, wherein the treatment portion comprises:
      an extendable and retractable input member operated by the control portion;
      a first link disconnectably connected to the input member through a first connecting portion;
      a first control plate disposed in the first connecting portion, the input member inserted through the first control plate, and the first control plate being configured to engage the input member by inclination of the first control plate;
      a first forceps member capable of opening and closing according to advancing and retracting motions of the first link;
      a second link disconnectably connected to the input member through a second connecting portion;
      a second control plate disposed in the second connecting portion, the input member inserted through the second control plate, and the second control plate being configured to engage the input member by inclination of the second control plate; and
      a second forceps member capable of opening and closing according to advancing and retracting motions of the second link, and having an opening-and-closing angle which is lower than an opening and closing angle of the first forceps member, and
      the second connection portion releases the connection between the input member and the second link after the input member is retracted by a predetermined length in the direction of closing a fully open second forceps member.

5. An endoscopic treatment instrument comprising:
   an insertion portion comprising a distal end and a proximal end, the distal end being adapted to be inserted into a human body;

a treatment portion disposed to the distal end; and
a control portion disposed to the proximal end, wherein
the treatment portion comprises:
- an extendable and retractable input member operated by the control portion;
- a first link disconnectably connected to the input member through a first connecting portion;
- a first control plate disposed in the first connecting portion, the input member inserted through the first control plate, and the first control plate being configured to engage the input member by inclination of the first control plate;
- a first forceps member capable of opening and closing according to advancing and retracting motions of the first link;
- a second link disconnectably connected to the input member through a second connecting portion; and
- a second control plate disposed in the second connecting portion, the input member inserted through the second control plate, and the second control plate being configured to engage the input member by inclination of the second control plate;
- a second forceps member capable of opening and closing according to advancing and retracting motions of the second link, and having an opening-and-closing angle which is lower than an opening and closing angle of the first forceps member, wherein the second connection portion releases the connection between the input member and the second link when the second forceps member is fully open.

6. The endoscopic treatment instrument according to one of claims 4 and 5, wherein
   the first and second connection portions each has a plurality of control plates each having one hole through which the input member is inserted,
   the hole provides engagement between the control plate and the input member when the control plate is disposed diagonally with respect to the moving direction of the input member, and
   the connection between the first and second connection portions and the input member is intermittently maintained by controlling the inclination of the control plates.

7. The endoscopic treatment instrument according to claim 6, wherein the plurality of control plates are urged in different diagonal directions.

* * * * *